United States Patent
Ise et al.

(10) Patent No.: US 11,700,769 B2
(45) Date of Patent: *Jul. 11, 2023

(54) ORGANIC ELECTROLUMINESCENT ELEMENT, COMPOUND, AND LIGHT EMITTING DEVICE, DISPLAY DEVICE AND LIGHTING SYSTEM, USING SAID ELEMENT

(71) Applicant: UDC IRELAND LIMITED, Dublin (IE)

(72) Inventors: Toshihiro Ise, Kanagawa (JP); Saki Takada, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 238 days.

This patent is subject to a terminal disclaimer.

(21) Appl. No.: 16/423,251

(22) Filed: May 28, 2019

(65) Prior Publication Data

US 2019/0355916 A1 Nov. 21, 2019

Related U.S. Application Data

(63) Continuation of application No. 14/239,704, filed as application No. PCT/JP2012/070976 on Aug. 20, 2012, now Pat. No. 10,326,084.

(30) Foreign Application Priority Data

Aug. 22, 2011 (JP) .................................. 2011-180905

(51) Int. Cl.
*H10K 85/60* (2023.01)
*C09B 57/00* (2006.01)
(Continued)

(52) U.S. Cl.
CPC ......... *H10K 85/6576* (2023.02); *C07C 13/62* (2013.01); *C07D 209/94* (2013.01);
(Continued)

(58) Field of Classification Search
CPC ... C07C 13/62; C07C 2603/54; C07D 209/94; C07D 307/77; C07D 307/93;
(Continued)

(56) References Cited

U.S. PATENT DOCUMENTS 8,628,863 B2 1/2014 Sekiguchi
8,748,010 B2 * 6/2014 Heil .................. C07C 13/72
252/301.16
(Continued)

FOREIGN PATENT DOCUMENTS

JP 05179237 7/1993
JP 2000077186 3/2000
(Continued)

OTHER PUBLICATIONS

J. of Materials Chemistry, (2002), vol. 12, pp. 1307-1310 (Year: 2002).*
(Continued)

*Primary Examiner* — Dawn L Garrett
(74) *Attorney, Agent, or Firm* — Riverside Law LLP

(57) ABSTRACT

An organic electroluminescent element including a substrate, a pair of electrodes including an anode and a cathode, disposed on the substrate, and at least one organic layer including a light emitting layer, disposed between the electrodes, in which at least one kind of compound represented by the following general formula is contained in any layer of the at least one organic layer, is an organic electroluminescent element, in which the generation of dark spots during driving is inhibited:

(Continued)

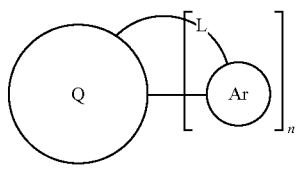

17 Claims, 1 Drawing Sheet

(51) Int. Cl.

| | |
|---|---|
| *C07D 495/06* | (2006.01) |
| *C07D 209/94* | (2006.01) |
| *C07C 13/62* | (2006.01) |
| *C09K 11/06* | (2006.01) |
| *H05B 33/10* | (2006.01) |
| *C07D 307/93* | (2006.01) |
| *C07D 487/06* | (2006.01) |
| *C07D 493/06* | (2006.01) |
| *C07D 493/16* | (2006.01) |
| *C07D 493/22* | (2006.01) |
| *C07D 495/16* | (2006.01) |
| *C07D 495/22* | (2006.01) |
| *C07D 307/77* | (2006.01) |
| *C07F 7/08* | (2006.01) |
| *H10K 50/11* | (2023.01) |

(52) U.S. Cl.
CPC ......... *C07D 307/77* (2013.01); *C07D 307/93* (2013.01); *C07D 487/06* (2013.01); *C07D 493/06* (2013.01); *C07D 493/16* (2013.01); *C07D 493/22* (2013.01); *C07D 495/06* (2013.01); *C07D 495/16* (2013.01); *C07D 495/22* (2013.01); *C07F 7/0812* (2013.01); *C09B 57/001* (2013.01); *C09K 11/06* (2013.01); *H05B 33/10* (2013.01); *H10K 50/11* (2023.02); *H10K 85/624* (2023.02); *H10K 85/657* (2023.02); *H10K 85/6572* (2023.02); *C07C 2603/54* (2017.05); *C09K 2211/1011* (2013.01); *C09K 2211/1088* (2013.01); *C09K 2211/1092* (2013.01); *C09K 2211/1096* (2013.01)

(58) Field of Classification Search
CPC .. C07D 487/06; C07D 493/06; C07D 493/16; C07D 493/22; C07D 495/06; C07D 495/16; C07D 495/22; C07F 7/0812; C09B 57/001; C09K 11/06; C09K 2211/1011; C09K 2211/1088; C09K 2211/1092; C09K 2211/1096; H01L 51/0056; H01L 51/0071; H01L 51/0072; H01L 51/0074; H01L 51/5012; H10K 85/6576; H10K 50/11; H10K 85/624; H10K 85/657; H10K 85/6572; H05B 33/10
See application file for complete search history.

(56) References Cited

U.S. PATENT DOCUMENTS

| | | |
|---|---|---|
| 9,000,420 B2 | 4/2015 | Kim |
| 9,051,233 B2 | 6/2015 | Buesing |
| 9,397,303 B2 | 7/2016 | Takada |
| 10,326,084 B2* | 6/2019 | Ise ..................... H01L 51/0071 |
| 2004/0076853 A1 | 4/2004 | Jarikov |
| 2006/0172147 A1* | 8/2006 | Matsuura ............ H01L 51/5036 428/917 |
| 2008/0100208 A1 | 5/2008 | Shin |
| 2009/0326150 A1 | 12/2009 | Kang |
| 2011/0084256 A1 | 4/2011 | Kim |
| 2011/0114889 A1* | 5/2011 | Buesing .............. H01L 51/0072 252/301.16 |
| 2012/0012826 A1 | 1/2012 | Kim |
| 2014/0246659 A1 | 9/2014 | Takaku |
| 2014/0291652 A1 | 10/2014 | Takada |
| 2014/0339519 A1 | 11/2014 | Takada |
| 2015/0053936 A1 | 2/2015 | Takaku |

FOREIGN PATENT DOCUMENTS

| | | | |
|---|---|---|---|
| JP | 2002359081 A | | 12/2002 |
| JP | 2009302466 | | 12/2009 |
| JP | 2009544743 | | 12/2009 |
| JP | 2011520784 | | 12/2009 |
| JP | 2010-087408 A | * | 4/2010 |
| JP | 2010-2015986 A | * | 9/2010 |
| JP | 2011079822 A | | 4/2011 |
| JP | 2012231134 | | 11/2012 |
| JP | 2013523847 | | 6/2013 |
| WO | 02060910 A1 | | 8/2002 |
| WO | 2010012328 A1 | | 2/2010 |
| WO | 2010013520 A1 | | 2/2010 |
| WO | 2010049050 | | 5/2010 |
| WO | 2010074520 A2 | | 7/2010 |
| WO | 2011128017 | | 10/2011 |

OTHER PUBLICATIONS

Fischer, E., Larsen, J., Christensen, J. B., Fourmigué, M., Madsen, H. G., & Harrit, N. (1996). Synthesis of new sulfur heteroaromatics isoelectronic with dibenzo [g, p] chrysene by photocyclization of thienyl-and phenyl-substituted ethenes. The Journal of Organic Chemistry, 61(20), 6997-7005. (Year: 1996).*
Chai, W. Y., Yang, E. Q., Zhang, Y. L., Xie, A. L., & Cao, X. P. (2012). Expeditious Synthesis of Papilionaceous Molecules Containing Oligobenzofurans. Synthesis, 44(03), 439-445. (Year: 2012).*
RN 1202746-94-8, Registry, Database Registry, Retrieved from STN , Jan. 26, 2010 (1 page).
RN 1203550-69-9, Registry, Database Registry, Retrieved from STN, Jan. 26, 2010 (1 page).
RN 1203550-70-2, Registry, Database Registry, Retrieved from STN, Jan. 27, 2010 (1 page).
RN 1203646-28-9, Registry, Database Registry, Retrieved from STN, Jan. 27, 2010 (1 page).
RN 1203646-29-0, Registry, Database Registry, Retrieved from STN, Jan. 27, 2010 (1 page).
RN 1203646-30-3, Registry, Database Registry, Retrieved from STN, Jan. 27, 2010 (1 page).
RN 1203646-31-4 Registry, Database Registry, Retrieved from STN, Jan. 27, 2010 (1 page).
RN 1203646-32-5 Registry, Database Registry, Retrieved from STN, Jan. 27, 2010 (1 page).

* cited by examiner

ORGANIC ELECTROLUMINESCENT ELEMENT, COMPOUND, AND LIGHT EMITTING DEVICE, DISPLAY DEVICE AND LIGHTING SYSTEM, USING SAID ELEMENT

CROSS-REFERENCE TO RELATED APPLICATIONS

The present application is a continuation of U.S. patent application Ser. No. 14/239,704, filed May 13, 2014, now allowed, which is the U.S. National Stage Application filed under 35 U.S.C. § 371 of International Patent Application No. PCT/JP2012/070976, filed Aug. 20, 2012, which claims priority to Japanese Patent Application No. 2011-180905, filed Aug. 22, 2011, all of which are hereby incorporated by reference in their entireties.

TECHNICAL FIELD

The present invention relates to an organic electroluminescent element and a compound used therefor (material for an organic electroluminescent element). The present invention further relates to a light emitting device, a display device, or an illumination device, using the organic electroluminescent element.

BACKGROUND ART organic electroluminescent elements (which may hereinafter also be referred to as "elements" or "organic EL elements") are light emitting elements which have organic layers between a pair of electrodes, and utilize, for light emitting, energy of the exciton generated as a result of recombination of electrons injected from a cathode and holes injected from an anode in the organic layer. Since the organic electroluminescent elements are capable of high-luminance light emitting at a low voltage, have a high response speed, and are relatively thin and light-weight, it is expected that the element can be employed in a wide range of applications, and the elements have been actively researched and developed.

As a material for an organic layer of an organic electroluminescent element, there have been known several compounds in a structure having an aromatic fused hydrocarbon ring having 10 to 30 carbon atoms, an aromatic fused heterocycle having 8 to 30 carbon atoms, or the like as a core skeleton, in which an aromatic group is used as a substituent, and the aromatic group and the core are linked via a linking group to form a non-aromatic fused ring structure.

For example, PTL 1 describes that a material in which a ring is formed with a single bond and a methylene chain with respect to a fused ring structure such as pyrene can be used as a light emitting material, a host material, or the like of an organic electroluminescent element. This literature exemplifies several compounds in which aryl pyrene is fused with a pyrene skeleton via a methylene chain, but describes only an aspect in which 1 or 2 fused rings are formed with the pyrene skeleton and the aryl substituent per pyrene skeleton.

PTL 2 describes that a compound having an aromatic fused hydrocarbon ring having 5 to 60 carbon atoms or an aromatic fused heterocycle having 2 to 60 carbon atoms as a core, in which there are 1 or 2 phenyl groups per core skeleton, can be used as a light emitting material for an organic electroluminescent element.

CITATION LIST

Patent Literature

[PTL 1] WO2010/012328 A1
[PTL 2] US2008/0100208 A1

SUMMARY OF INVENTION

Technical Problem

However, the present inventors have investigated, and as a result of the investigation on the performance of an organic electroluminescent element prepared by using such a compound as a material of the organic electroluminescent element, they have found that there is a problem of generation of dark spots during driving.

The present invention aims to solve the foregoing problems. It is an object of the present invention to provide an organic electroluminescent element, in which the generation of dark spots during driving is inhibited.

Solution to Problem

Therefore, the present inventors have conducted extensive investigations for the purpose of providing an organic electroluminescent element, in which the generation of dark spots during driving is inhibited. As a result, they have found that the aforementioned problems are solved by using a compound having a specific structure, thereby providing the present invention as described below.

[1] An organic electroluminescent element including a substrate, a pair of electrodes including an anode and a cathode, disposed on the substrate, and at least one organic layer including a light emitting layer, disposed between the electrodes, in which at least one kind of compound represented by the following general formula (I) is contained in any layer of the at least one organic layer.

[Chem. 1]

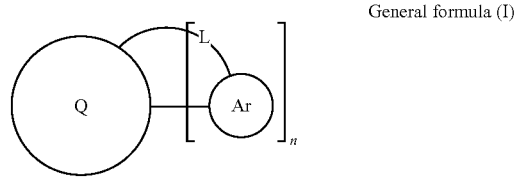

General formula (I)

(In the general formula (I), Q represents an aromatic fused hydrocarbon ring having 10 to 30 carbon atoms or an aromatic fused heterocycle having 8 to 30 carbon atoms. Ar's each independently represent an arylene group having 6 to 30 carbon atoms or a heteroarylene group having 3 to 30 carbon atoms. L's each independently represent a divalent linking group. n represents an integer of 3 to 5.)

[2] In the organic electroluminescent element as described in [1], in the general formula (I), L is preferably $CR^{12}R^{13}$, $NR^{14}$, $SiR^{15}SR^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom.

[3] In the organic electroluminescent element as described in [1] or [2], in the general formula (I), Q preferably represents any one of naphthalene, anthracene, phenanthrene, pyrene, chrysene, perylene, and triphenylene.

[4] In the organic electroluminescent element as described in any one of [1] to [3], in the general formula (I), Ar's preferably each independently represent a substituted or unsubstituted phenylene group.

[5] In the organic electroluminescent element as described in any one of [1] to [4], in the general formula (I), Q preferably represents pyrene.

[6] In the organic electroluminescent element as described in any one of [1] to [5], the compound represented by the general formula (I) is preferably a compound represented by the following general formula (II).

[Chem. 2]

General formula (II)

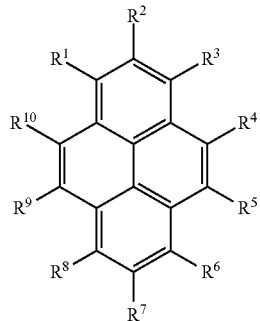

(In the general formula (II), $R^1$ to $R^{10}$ represent a hydrogen atom or a substituent, three out of the combinations of $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^8$ and $R^9$, $R^9$ and $R^{10}$ and $R^{10}$ and $R^1$ are substituted with each independent group represented by the following general formula B.)

[Chem. 3]

General formula B

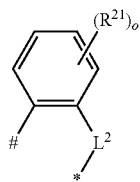

(In the general formula B, $L^2$ represents $CR^{12}R^{13}$, $NR^{14}$, $SiR^{15}R^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom. * and # represent sites for substitution with any one of the combinations of $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^8$ and $R^9$, $R^9$ and $R^{10}$, or $R^{10}$ and $R^1$ in the general formula (II), one of two groups in the combinations may be substituted at * or the other may be substituted at #. $R^{21}$'s each independently represent a substituent. o represents an integer of 0 to 4. In the case where o is 2 to 4, the respective $R^{21}$'s may be the same as or different from each other, and $R^{21}$'s may be bonded to each other to form a ring.)

[7] In the organic electroluminescent element as described in [6], the compound represented by the general formula (II) is preferably a compound represented by the following general formula (III).

[Chem. 4]

General formula (III)

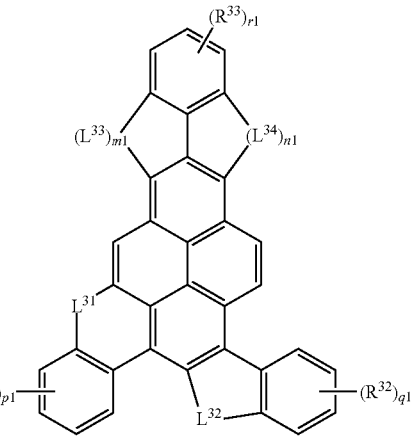

(In the general formula (III), $L^{31}$, $L^{32}$, $L^{33}$ and $L^{34}$ each independently represent $CR^{12}R^{13}$, $NR^{14}$, $SiR^{15}R^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom. m1 and n1 are each 0 or 1, satisfying m1+n1=1. $R^{31}$, $R^{32}$ and $R^{33}$ each independently represent a substituent. p1, q1 and r1 each independently represent an integer of 0 to 4. In the case where p1, q1 and r1 are each 2 to 4, $R^{31}$, $R^{32}$ and $R^{33}$ may be the same as or different from each other, and $R^{31}$'s, $R^{32}$'s, or $R^{33}$'s may be bonded to each other to form a ring.)

[8] In the organic electroluminescent element as described in [6], the compound represented by the general formula (II) is preferably a compound represented by the following general formula (IV).

[Chem. 5]

General formula (IV)

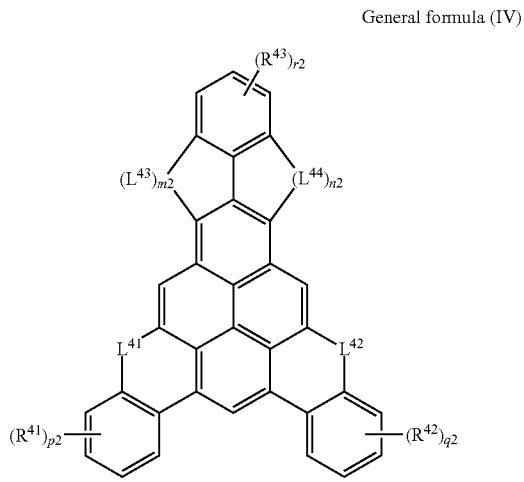

(In the general formula (IV), $L^{41}$, $L^{42}$, $L^{43}$ and $L^{44}$ each independently represent $CR^{12}R^{13}$, $NR^{14}$, $SiR^{15}R^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom. m2 and n2 are each 0 or 1, satisfying m2+n2=1. $R^{41}$, $R^{42}$ and $R^{43}$ each independently represent a substituent. p2, q2 and r2 each independently represent an integer of 0 to 4. In the case where p2, q2 and r2 are each 2 to 4, $R^{41}$, $R^{42}$, $R^{43}$ may be the same as or different from each other, and $R^{41}$'s, $R^{42}$'s, or $R^{43}$'s may be bonded to each other to form a ring.)

[9] In the organic electroluminescent element as described in [6], the compound represented by the general formula (II) is preferably a compound represented by the following general formula (V).

[Chem. 6]

General formula (V)

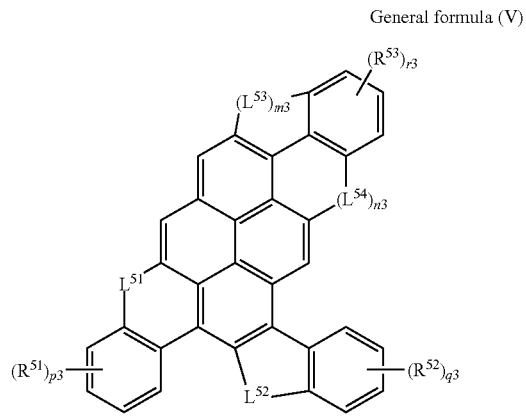

(In the general formula (V), $L^{b1}$, $L^{b2}$, $L^{b3}$ and $L^{b4}$ each independently represent $CR^{12}R^{13}$, $NR^{14}$, $SiR^{15}R^{16}$ ($R^{12}$, $R^{13}$, $R^{14}$, $R^{15}$ and $R^6$ each independently represent a fluorine atom, an alkyl group, an aryl group, or a heteroaryl group), an O atom, or an S atom. m3 and n3 are each 0 or 1, satisfying m3+n3=1. $R^{51}$, $R^{52}$ and $R^{53}$ each independently represent a substituent. p3, q3 and r3 each independently represent an integer of 0 to 4. In the case where p3, q3 and r3 are each 2 to 4, $R^{51}$, $R^{52}$, $R^{53}$ may be the same as or different from each other, and $R^{51}$'s, $R^{52}$'s, or $R^{53}$'s may be bonded to each other to form a ring.)

[10] In the organic electroluminescent element as described in [6], the compound represented by the general formula (II) is preferably a compound represented by the following general formula (VI).

[Chem. 7]

General formula (VI)

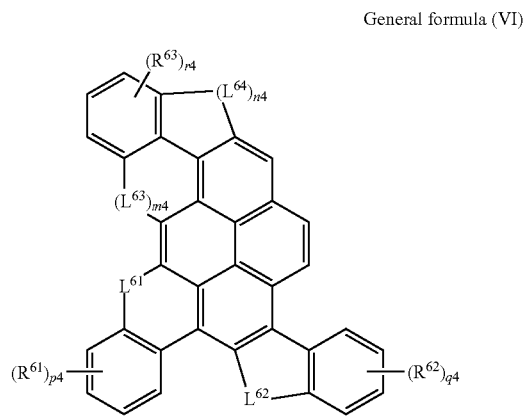

(In the general formula (VI), $L^{61}$, $L^{62}$, $L^{63}$ and $L^{64}$ each independently represent $CR^{12}R^{13}$, $NR^{14}$, $SiR^{15}$, $R^{16}$ ($R^{12}$, $R^{13}$, $R^{14}$, $R^{15}$ and $R^{16}$ each independently represent a fluo-rine atom, an alkyl group, an aryl group, or a heteroaryl group), an O atom, or an S atom. m4 and n4 are each 0 or 1, satisfying m4+n4=1. $R^{61}$, $R^{62}$ and $R^{63}$ each independently represent a substituent. p4, q4 and r4 each independently represent an integer of 0 to 4. In the case where p4, q4 and r4 are each 2 to 4, $R^{61}$, $R^{62}$, $R^{63}$ may be the same as or different from each other, and $R^{61}$'s, $R^{62}$'s, or $R^{63}$'s may be bonded to each other to form a ring.)

[11] In the organic electroluminescent element as described in any one of [1] to [10], the compound represented by the general formula (I) is preferably contained in the light emitting layer.

[12] In the organic electroluminescent element as described in any one of [1] to [11], the compound represented by the general formula (I) is preferably a light emitting material contained in the light emitting layer.

[13] In the organic electroluminescent element as described in [12], further including a host material in the light emitting layer.

[14] In the organic electroluminescent element as described in [13], the host material preferably has an anthracene skeleton.

[15] A light emitting device using the organic electroluminescent element as described in any one of [1] to [14].

[16] A display device using the organic electroluminescent element as described in any one of [1] to [14].

[17] An illumination device using the organic electroluminescent element as described in any one of [1] to [14].

[18] A compound represented by the following general formula (III).

[Chem. 8]

General formula (III)

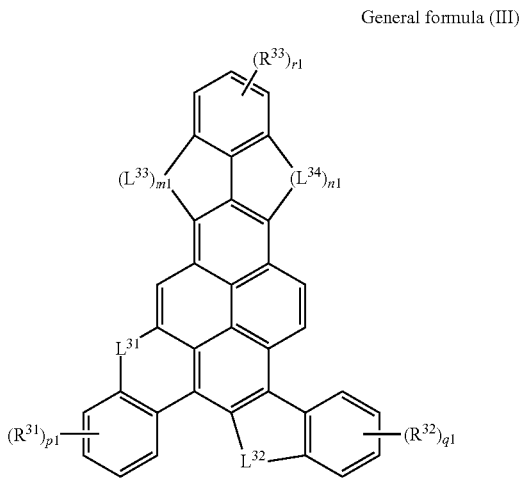

(In the general formula (III), $L^{31}$, $L^{32}$, $L^{33}$ and $L^{34}$ each independently represent $CR^{12}R^{13}$, $NR^{14}$, $SiR^{15}R^{16}$ ($R^{12}$, $R^{13}$, $R^{14}$, $R^{15}$ and $R^{16}$ each independently represent a fluo-rine atom, an alkyl group, an aryl group, or a heteroaryl group), an O atom, or an S atom. m1 and n1 are each 0 or 1, satisfying m1+n1=1. $R^{31}$, $R^{32}$ and $R^{33}$ each independently represent a substituent. p1, q1 and r1 each independently represent an integer of 0 to 4. In the case where p1, q1 and r1 are each 2 to 4, $R^{21}$, $R^{32}$ and $R^{33}$ may be the same as or different from each other, and $R^{31}$'s, $R^{32}$'s, or $R^{33}$'s may be bonded to each other to form a ring.)

Advantageous Effects of Invention

The organic electroluminescent element of the present invention has advantageous effects in that generation of dark spots during driving is inhibited. Further, when the compound of the present invention is used, such an excellent organic electroluminescent element can be easily prepared. Further, the light emitting device, the display device, and the illumination device of the present invention has advantageous effects in that the generation of dark spots is reduced.

DESCRIPTION OF EMBODIMENTS

Figure 1:
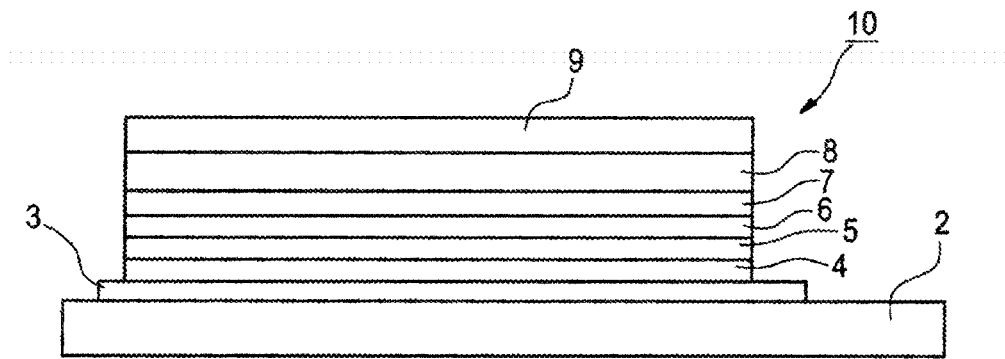
FIG. 1 is a schematic view showing one example of a configuration of an organic electroluminescent element according to the present invention.

Hereinafter, the details of the present invention will be described. The description of the configuration requirements as described below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Compound Represented by General Formula (I)]

The compound represented by the general formula (I) of the present invention can be preferably used as a material for an organic electroluminescent element. In the organic electroluminescent element of the present invention as described later, the organic layer constituting the organic electroluminescent element contains the compound represented by the general formula (I).

[Chem. 9]

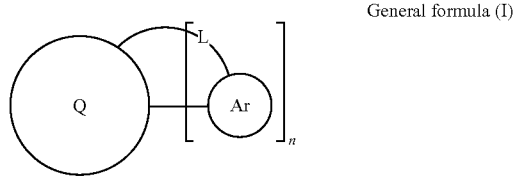

General formula (I)

(In the general formula (I), Q represents an aromatic fused hydrocarbon ring having 10 to 30 carbon atoms or an aromatic fused heterocycle having 8 to 30 carbon atoms. Ar's each independently represent an arylene group having 6 to 30 carbon atoms or a heteroarylene group having 3 to 30 carbon atoms. L's each independently represent a divalent linking group. n represents an integer of 3 to 5.)

In the compound represented by the general formula (I) of the present invention, n is 3 to 5 and the number of the fused ring structures of —Ar-L- is 3 to 5 per core skeleton. Compounds having such a structure have not been known in the related art. Not wishing to be restricted to any theory, when the compound represented by the general formula (I) is used as a material for an organic electroluminescent element, generation of dark spots during driving is inhibited. The effects exhibited by the compound having the structure represented by the general formula (I) have not been known in the related art and the organic electroluminescent element exhibiting such effects is advantageous for a case where the element is mounted on a display.

Further, even in a case where an organic electroluminescent element is prepared at a high dew point temperature (for example, −20° C.), the organic electroluminescent element exhibiting the performance as described above can be obtained with the compound of the present invention. As used in the specification, the dew point temperature refers to "a temperature at which condensation begins when air including water vapor is cooled". Even in a case of preparing an organic electroluminescent element in the range of dew point temperatures (for example, lower than −20° C.), an organic electroluminescent element exhibiting the performance as described above can be obtained using the compound of the present invention, and therefore, it is possible to prepare an organic electroluminescent element at a wide range of dew point temperatures. Since the compound of the present invention can be preferably used for the preparation of an element even in a range of high dew point temperatures, the logical reason why the structure of the compound of the present invention becomes advantageous for film formation under an atmosphere with a high content of moisture was unknown and unpredictable.

The dew point temperature in the present specification was measured with a hygrometer (NS-100D, manufactured by Nippon Yakin Kogyo Co., Ltd.) in a type for detecting moisture by an electrostatic capacitance method.

Hereinbelow, the compound represented by the general formula (I) will be described in detail.

In the present invention, in the description of the general formula (I), the hydrogen atom includes isotopes thereof (deuterium atom and the like), and the atom additionally constituting the substituent includes isotopes thereof.

In the present invention, when referring to a "substituent", the substituent may be further substituted. For example, when the "alkyl group" is referred to in the present invention, it includes an alkyl group substituted with a fluorine atom (for example, a trifluoromethyl group) and an alkyl group substituted with an aryl group (for example, a triphenylmethyl group), but when "an alkyl group having 1 to 6 carbon atoms" is referred to herein, it represents any of alkyl groups having 1 to 6 carbon atoms, including the alkyl groups which are substituted.

In the general formula (I), Q represents an aromatic fused hydrocarbon ring having 10 to 30 carbon atoms or an aromatic fused heterocycle having 8 to 30 carbon atoms. Q is preferably a fused aromatic ring structure having 3 or more constituent rings. Further, the respectively constituent rings are more preferably all hydrocarbon rings.

The fused aromatic ring structure having 3 or more constituent ring is not particularly limited, but the Q is preferably any one of naphthalene, anthracene, phenanthrene, pyrene, chrysene, perylene, and triphenylene, and more preferably pyrene.

The Q may have a substituent other than Ar and L. The substituent is not particularly limited, but it is preferable that the substituent does not form a ring fused with the Q.

In the general formula (I), Ar's each independently represent an arylene group having 6 to 30 carbon atoms or a heteroarylene group having 3 to 30 carbon atoms.

Ar may have an additional substituent.

The Ar more preferably represents an arylene group having 6 to 30 carbon atoms or a heteroarylene group having 3 to 30 carbon atoms, particularly preferably an arylene group having 6 to 30 carbon atoms, and more particularly preferably any of phenylene groups which are each independently substituted or unsubstituted.

In the general formula (I), n represents an integer of 3 to 5, preferably 3 or 4, and particularly preferably 3.

In the general formula (I), L's each independently represent a divalent linking group. The linking group represented by L is not particularly limited, but in the present invention, L preferably $CR^{12}R^{13}$, $NR^{14}$, $SiR^{15}R^{16}$ ($R^{12}$, $R^{13}$, $R^{14}$, $R^{15}$ and $R^{16}$ each independently represent a substituent, fluorine atom, an alkyl group, an aryl group, or a heteroaryl group), an O atom, or an S atom, and more particularly preferably $CR^{12}R^{13}$, $NR^{14}$, or and S atom.

$R^{12}$, $R^{13}$, $R^{15}$ and $R^{16}$ (substituents at carbon atoms and substituents at silicon atoms) include the following Substituent Group A.

<<Substituent Group A>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, anthranyl), amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), and aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 1 to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), phosphoramide group (preferably having 1 to 30 carbon atoms, more preferably having 1 to 20 carbon atoms, and particularly preferably having 1 to 12 carbon atoms; for example, diethylphosphoramide and phenylphosphoramide), a hydroxy group, a mercapto group, a halogen atom (for example, a fluorine atom, a chlorine atom, a bromine atom, and an iodine atom), a cyano group, a sulfo group, a carboxyl group, a nitro group, ahydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the additional substituent include the groups selected from the Substituent Group A as described above. Further, the substituent substituted with a substituent may be further substituted, and examples of the additional substituent include the groups selected from the Substituent Group A as described above. In addition, the substituent substituted with the substituent substituted with a substituent may be further substituted, and examples of the additional substituent include the groups selected from the Substituent Group A as described above.

It is more preferable that $R^{12}$, $R^{13}$, $R^{15}$ and $R^{16}$ each independently represent a fluorine atom, an alkyl group, an aryl group, or a heteroaryl group.

It is still more preferable that $R^2$, $R^{13}$, $R^{15}$ and $R^{16}$ each independently represent any one of a fluorine atom, a linear, branched, or cyclic alkyl group having 1 to 10 carbon atoms; an aryl group having 6 to 14 carbon atoms; and a heteroaryl group having 3 to 20 carbon atoms and containing any one of N, O, and S as a hetero atom; and it is particularly preferable that $R^{12}$, $R^{13}$, $R^{15}$ and $R^{16}$ each independently represent a linear or branched alkyl group having 1 to 6 carbon atoms. Further, from the viewpoint of easiness of synthesis, it is preferable that $R^{12}$ and $R^{13}$ be the same substituent. Further, from the same viewpoint, it is also preferable that $R^{15}$ and $R^{16}$ be the same substituent.

$R^{12}$, $R^{13}$, $R^{15}$ and $R^{16}$ may be combined with each other to form a 5- or 6-membered ring. The 5- or 6-membered ring thus formed may be any one of a cycloalkyl ring, a cycloalkenyl ring, and a heterocycle. Examples of the heterocycle include those containing 1 to 3 hetero atoms selected from a group consisting of a nitrogen atom, an oxygen atom, and a sulfur atom as a ring-constituting atom. The 5- or 6-membered ring thus formed may have a substituent, examples of the substituent at carbon atoms include the Substituent Group A as described above, and examples of the substituent at nitrogen atoms include the Substituent Group B as described above.

Examples of the $R^{14}$ (substituent at nitrogen atoms) include the following Substituent Group B.

<<Substituent Group B>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, and anthranyl), a cyano group, and a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group). These substituents may be further substituted, and examples of the additional substituent include the groups selected from the Substituent Group A as described above. Further, the substituent substituted with a substituent may be further substituted, and examples of the additional substituent include the groups selected from the Substituent Group A as described above. In addition, the substituent substituted with the substituent substituted with a substituent may be further substituted, and examples of the additional substituent include the groups selected from the Substituent Group A as described above.

$R^{14}$ is preferably an alkyl group, a perfluoroalkyl group, or an aryl group. $R^c$ is more preferably any one of a linear, branched, or cyclic alkyl group having 1 to 10 carbon atoms; an aryl group having 6 to 50 carbon atoms; and a heteroaryl group having 5 to 20 carbon atoms and at least one of N, O, and S as a hetero atom. $R^{14}$ is more preferably an aryl group having 6 to 14 carbon atoms; or a heteroaryl group having 5 to 20 carbon atoms and at least one of N, O, and S as a hetero atom.

$R^{14}$ may have an additional substituent, and the substituent is not particularly limited, but is preferably an alkyl group or an aryl group. The alkyl group as used herein is preferably an unsubstituted linear alkyl group, an unsubstituted branched alkyl group, an unsubstituted cycloalkyl group, or a perfluoroalkyl group; more preferably a linear alkyl group having 1 to 6 carbon atoms, a branched alkyl group having 1 to 6 carbon atoms, or a perfluoroalkyl group having 1 to 6 carbon atoms; particularly preferably a methyl group, an ethyl group, an isopropyl group, a t-butyl group, a t-amyl group, a neopentyl group, or a trifluoromethyl group; and more particularly preferably a methyl group, an ethyl group, an isopropyl group, or a t-butyl group. On the other hand, the aryl group as used herein is preferably an aryl group having 6 to 14 carbon atoms, more preferably an aryl group having 6 to 10 carbon atoms, and particularly preferably a phenyl group.

The compound represented by the general formula (I) is preferably a compound represented by the following general formula (II).

[Chem. 10]

General formula (II)

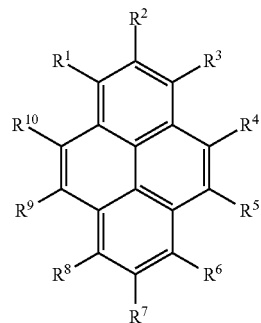

(In the general formula (II), $R^1$ to $R^{10}$ represent a hydrogen atom or a substituent, and three out of the combinations of $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^8$ and $R^9$, $R^9$ and $R^{10}$ and $R^{10}$ and $R^1$ are substituted with each independent groups represented by the following general formula B.)

[Chem. 11]

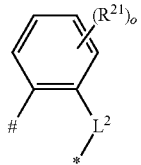

General formula B (In the general formula B, $L^2$ represents $CR^{12}R^{13}$, $NR^{14}$, $SiR^{15}R^{16}$, an O atom, or an S atom. * and # represent sites for substitution with any one of the combinations of $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^8$ and $R^9$, $R^9$ and $R^{10}$ or $R^{10}$ and $R^1$ in the general formula (II), one of two groups in the combinations may be substituted at * or the other may be substituted at #. $R^{21}$'s each independently represent a substituent. o represents an integer of 0 to 4. In the case where o is 2 to 4, the respective $R^{21}$'s may be the same as or different from each other and $R^{21}$'s may be bonded to each other to form a ring.)

In the general formula (II), $R^1$ to $R^{10}$ represent a hydrogen atom or a substituent, and three out the combinations of $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^8$ and $R^9$, $R^9$ and $R^{10}$ and $R^{10}$ and $R^1$ is substituted with a group represented by the general formula B. The combinations substituted with the general formula B are preferably combinations of $R^1$ and $R^2$, $R^2$ and $R^3$, $R^3$ and $R^4$, $R^6$ and $R^7$, $R^8$ and $R^9$ and $R^{10}$ and $R^1$.

For $R^1$ to $R^{10}$ in the general formula (II), the site which is not substituted with the general formula B is a hydrogen atom or a substituent, and preferred examples of the substituent include the Substituent Group A. In $R^1$ to $R^{10}$, it is preferable that the sites which be not substituted with the general formula B be all hydrogen atoms.

in the group represented by the general formula B is substituted at any one position of $R^1$, $R^2$ and $R^3$ in the general formula (II), preferably substituted at 3 positions in total of $R^6$ and $R^8$, and more preferably substituted at any one position of $R^1$ and $R^2$ and 3 positions in total of $R^6$ and $R^8$.

The description and the preferred range of $L^2$ in the group represented by the general formula B are the same as the description and the preferred range of L in the group represented by the general formula (I).

$R^{21}$'s in the group represented by the general formula B each independently represent a substituent, and examples of the substituent include the Substituent Group A as described above. Above all, $R^{21}$ is preferably a substituent having any one of a fluorine atom, an alkyl group, a silyl group, an aryl group, an aryloxy group, a cyano group, and an amino group, and specific examples thereof include a fluorine atom, an alkyl group, a perfluoroalkyl group, a trialkylsilyl group, a phenyl group, a phenoxy group, and a di-substituted amino group. $R^{21}$ more preferably represents an alkyl group, a silyl group, an aryl group, an aryloxy group, or a di-substituted amino group.

The alkyl group represented by $R^{21}$ is preferably an unsubstituted linear alkyl group, an unsubstituted branched alkyl group, an unsubstituted cycloalkyl group, or a perfluoroalkyl group, and more preferably a linear alkyl group having 1 to 6 carbon atoms, a branched alkyl group having 1 to 6 carbon atoms, or a perfluoroalkyl group having 1 to 6 carbon atoms. The silyl group represented by $R^{21}$ is preferably an alkylsilyl group, and the substituted or unsubstituted aryl group, and the di-substituted amino group, each represented by $R^{21}$, is preferably an aryl group substituted with an N,N-diarylamino group or an alkyl group, or a substituent having an N,N-diarylamino group.

In the group represented by the general formula B, o represents 0 to 4, and o is preferably 0 or 1, and more preferably 0.

In the case where o is 2 to 4, the respective $R^{21}$'s may be the same as or different from each other. $R^{21}$'s may be bonded to each other to form a ring, but it is preferably that they do not form a ring.

In the organic electroluminescent element of the present invention, the compound represented by the general formula (II) is preferably a compound represented by any one of the following general formulae (III) to (VI). Hereinafter, the general formulae (III) to (VI) will be described in order.

In the organic electroluminescent element of the present invention, the compound represented by the general formula (II) is preferably a compound represented by the following general formula (III).

[Chem. 12]

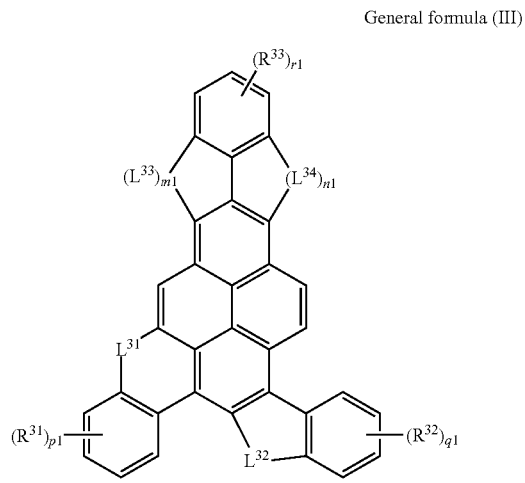

General formula (III)

(In the general formula (III), $L^{31}$, $L^{32}$, $L^{33}$ and $L^{34}$ each independently represent $CR^{12}R^{13}$, $NR^{14}$, $SiR^{15}R^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom. m1 and n1 are each 0 or 1, satisfying m1+n1=1. $R^{31}$, $R^{32}$ and $R^{33}$ each independently represent a substituent. p1, q1 and r1 each independently represent an integer of 0 to 4. In the case where p1, q1 and r1 are each 2 to 4, $R^{31}$, $R^{32}$ and $R^{33}$ may be the same as or different from each other, and $R^{31}$'s, $R^{32}$'s, or $R^{33}$'s may be bonded to each other to form a ring.)

In the general formula (III), $L^{31}$, $L^{32}$, $L^{33}$ and $L^{34}$ each independently represent $CR^{12}R^{13}$, $NR^{14}$, $SiR^{15}R^{16}$, an O atom, or an S atom. The descriptions and the preferred ranges of $L^{31}$, $L^{32}$, $L^{33}$ and $L^{34}$ are the same as the description and the preferred range of L in the group represented by the general formula (I).

In the general formula (III), m1 and n1 are each 0 or 1, satisfying m1+n1=1. Above all, it is preferable that m1 be 0 and n1 be 1 from the viewpoint of inhibition of generation of dark spots during driving.

In the general formula (III), $R^{31}$, $R^{32}$ and $R^{33}$ each independently represent a substituent. The descriptions and the preferred ranges of $R^{31}$, $R^{32}$ and $R^{33}$ are the same as the description and the preferred range of $R^{21}$ in the general formula (II).

In the general formula (III), p1, q1 and r1 each independently represent an integer of 0 to 4. In the case where p1, q1 and r1 are each 2 to 4, $R^{31}$, $R^{32}$ and $R^{33}$ may be the same as or different from each other, and $R^{31}$'s, $R^{32}$'s, or $R^{33}$'s may be bonded to each other to form a ring. The descriptions and the preferred ranges of p1, q1 and r1 are the same as the description and the preferred range of o in the general formula (II).

In the organic electroluminescent element of the present invention, the compound represented by the general formula (II) is preferably a compound represented by the following general formula (IV).

[Chem. 13]

General formula (IV)

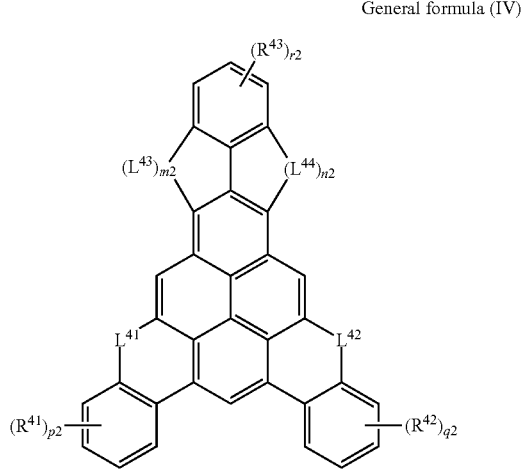

(In the general formula (IV), $L^{41}$, $L^{42}$, $L^{43}$ and $L^{44}$ each independently represent $CR^{12}R^{13}$, $NR^{14}$, $SiR^{15}R^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom. m2 and n2 are each 0 or 1, satisfying m2+n2=1. $R^{41}$, $R^{42}$ and $R^{43}$ each independently represent a substituent. p2, q2 and r2 each independently represent an integer of 0 to 4. In the case where p2, q2 and r2 are each 2 to 4, $R^{41}$, $R^{42}$ and $R^{43}$ may be the same as or different from each other, and $R^{41}$'s, $R^{42}$'s, or $R^{43}$'s may be bonded to each other to form a ring.)

In the general formula (IV), $L^{41}$, $L^{42}$, $L^{43}$ and $L^{44}$ each independently represent $CR^{12}R^{13}$, $NR^{14}$, $SiR^{15}R^{16}$, an O atom, or an S atom. The descriptions and the preferred ranges of $L^{41}$, $L^{42}$, $L^{43}$ and $L^{44}$ are the same as the description and the preferred range of L in the general formula (I).

In the general formula (IV), m2 and n2 are each 0 or 1, satisfying m2+n2=1. Above all, it is preferable that m2 be 0 and n2 be 1 from the viewpoint of inhibition of generation of dark spots during driving.

In the general formula (IV), $R^{41}$, $R^{42}$ and $R^{43}$ each independently represent a substituent. The descriptions and the preferred ranges of $R^{41}$, $R^{42}$ and $R^{43}$ are the same as the description and the preferred range of $R^{21}$ in the general formula (II).

In the general formula (IV), p2, q2 and r2 each independently represent an integer of 0 to 4. In the case where p2, q2 and r2 are each 2 to 4, $R^{41}$, $R^{42}$ and $R^{43}$ may be the same as or different from each other, and $R^{41}$'s, $R^{42}$'s, or $R^{43}$'s may be bonded to each other to form a ring. The descriptions and the preferred ranges of p2, q2 and r2 are the same as the description and the preferred range of o in the general formula (II).

In the organic electroluminescent element of the present invention, the compound represented by the general formula (II) is preferably a compound represented by the following general formula (V).

[Chem. 14]

General formula (V)

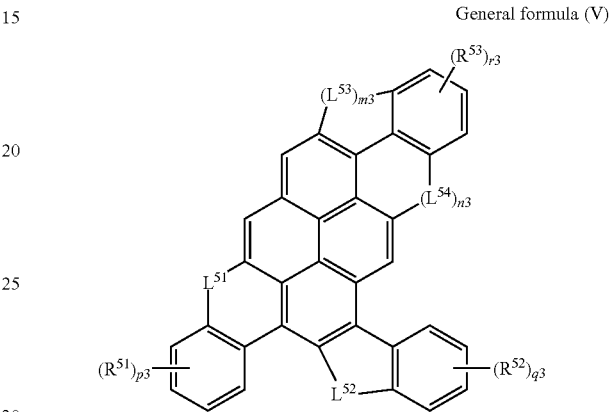

(In the general formula (V), $L^{51}$, $L^{52}$, $L^{53}$ and $L^{54}$ each independently represent $CR^{12}R^{13}$, $NR^{14}$, $SiR^{15}R^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom. m3 and n3 are each 0 or 1, satisfying m3+n3=1. $R^{51}$, $R^{52}$ and $R^{53}$ each independently represent a substituent. p3, q3 and r3 each independently represent an integer of 0 to 4. In the case where p3, q3 and r3 are each 2 to 4, $R^{51}$, $R^{52}$ and $R^{53}$ may be the same as or different from each other, and $R^{51}$'s, $R^{52}$'s, or $R^{53}$'s may be bonded to each other to form a ring.)

In the general formula (V), $L^{51}$, $L^{52}$, $L^{53}$ and $L^{54}$ each independently represent $CR^{12}R^{13}$, $NR^{14}$, $SiR^{15}R^{16}$, an O atom, or an S atom. The descriptions and the preferred ranges of $L^{51}$, $L^{52}$, $L^{53}$ and $L^{54}$ are the same as the description and the preferred range of L in the general formula (I).

In the general formula (V), m3 and n3 are each 0 or 1, satisfying m3+n3=1. Above all, it is preferable that m3 be 1 and n3 be 0.

In the general formula (V), $R^{51}$, $R^{52}$ and $R^{53}$ each independently represent a substituent. The descriptions and the preferred ranges of $R^{51}$, $R^{52}$ and $R^{53}$ are the same as the description and the preferred range of $R^{21}$ in the general formula (II).

In the general formula (V), p3, q3 and r3 each independently represent an integer of 0 to 4. In the case where p3, q3 and r3 are each 2 to 4, $R^{51}$, $R^{52}$ and $R^{53}$ may be the same as or different from each other, and $R^{51}$'s, $R^{52}$'s, or $R^{53}$'s may be bonded to each other to form a ring. The descriptions and the preferred ranges of p3, q3 and r3 are the same as the description and the preferred range of o in the general formula (II).

In the organic electroluminescent element of the present invention, the compound represented by the general formula (II) is preferably a compound represented by the following general formula (VI).

[Chem. 15]

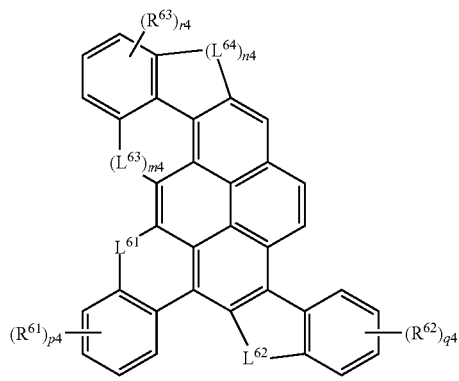

General formula (VI)

(In the general formula (VI), $L^{61}$, $L^{62}$, $L^{63}$ and $L^{64}$ each independently represent $CR^{12}R^{13}$, $NR^{14}$, $SiR^{15}SR^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom. m4 and n4 are each 0 or 1, satisfying m4+n4=1. $R^{61}$, $R^{62}$ and $R^{63}$ each independently represent a substituent. p4, q4 and r4 each independently represent an integer of 0 to 4. In the case where p4, q4 and r4 are each 2 to 4, $R^{61}$, $R^{62}$ and $R^{63}$ may be the same as or different from each other, and $R^{61}$'s, $R^{62}$'s, or $R^{63}$'s may be bonded to each other to form a ring.)

In the general formula (VI), $L^{61}$, $L^{62}$, $L^{63}$ and $L^{64}$ each independently represent $CR^{12}R^{13}$, $NR^{14}$, $SiR^{15}R^{16}$, an O atom, or an S atom. The descriptions and the preferred ranges of $L^{61}$, $L^{62}$, $L^{63}$ and $L^{64}$ are the same as the description and the preferred range of L in the general formula (I).

In the general formula (VI), m3 and n3 are each 0 or 1, satisfying m3+n3=1. Above all, it is preferable that m3 be 1 and n3 be 0.

In the general formula (VI), $R^{61}$, $R^{62}$ and $R^{63}$ each independently represent a substituent. The descriptions and the preferred ranges of $R^{61}$, $R^{62}$ and $R^{63}$ are the same as the description and the preferred range of $R^{21}$ in the general formula (II).

In the general formula (VI), p4, q4 and r4 each independently represent an integer of 0 to 4. In the case where p4, q4 and r4 are each 2 to 4, $R^{61}$, $R^{62}$ and $R^{63}$ may be the same as or different from each other, and $R^{61}$'s, $R^{62}$'s, or $R^{63}$'s may be bonded to each other to form a ring. The descriptions and the preferred ranges of p4, q4 and r4 are the same as the description and the preferred range of o in the general formula (II).

The compound represented by the general formula (II) is more preferably a compound represented by the general formula (III), (IV), or (VI).

The molecular weight of the compound represented by the general formula (I) is preferably 1000 or less, more preferably 900 or less, particularly preferably 850 or less, and still more preferably 800 or less. By reducing the molecular weight, the sublimation temperature can be lowered, and thus, it is possible to prevent the thermal decomposition of the compound during deposition. Further, the energy required for deposition can be suppressed by decreasing the deposition time. Here, since a material having a high sublimation temperature can undergo thermal decomposition during long-term deposition, it is favorable that the sublimation temperature be not too high from the viewpoint of deposition suitability. The sublimation temperature (which means a temperature which leads to reduction in 10% by mass in the present specification) of the compound represented by the general formula (I) is preferably 300° C., more preferably 285° C. or lower, and still more preferably 270° C. or lower.

Specific examples of the compound represented by the general formula (I) are shown below, but it should not be construed that the compound represented by the general formula (I) which can be used in the present invention is limited to the specific examples.

[Chem. 16]

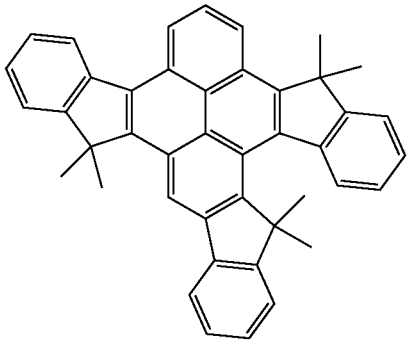

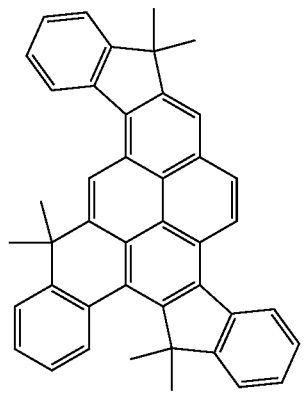

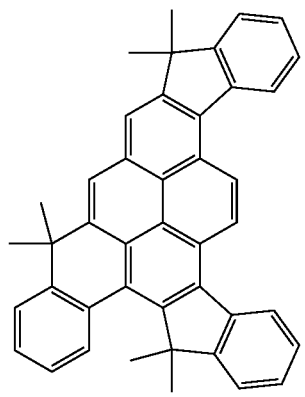

-continued
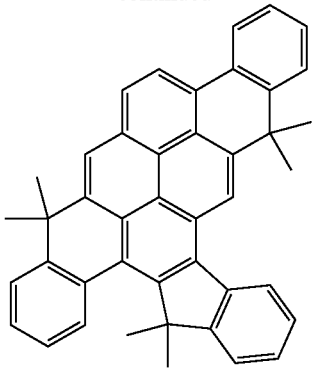
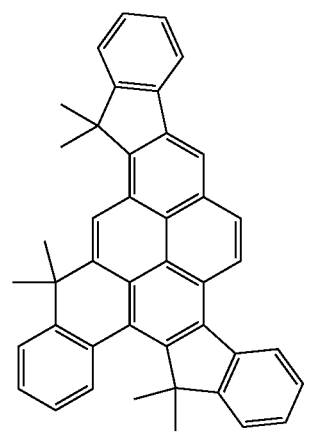
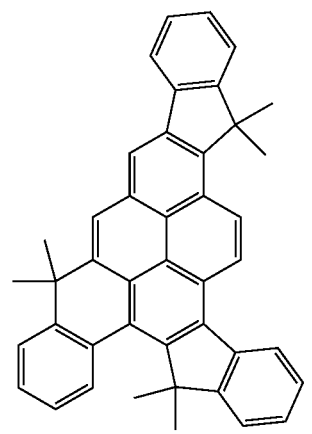
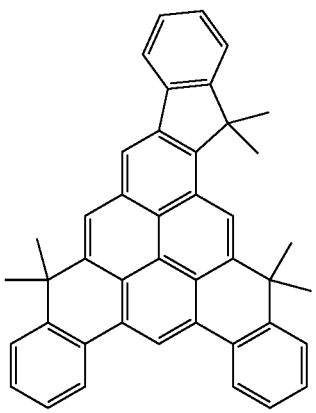
-continued
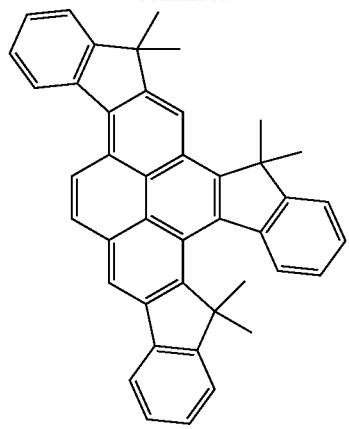
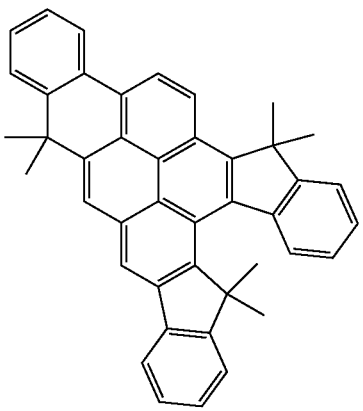
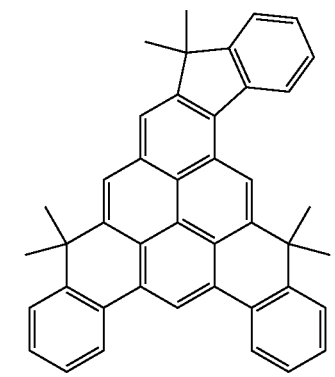
[Chem. 17-1]
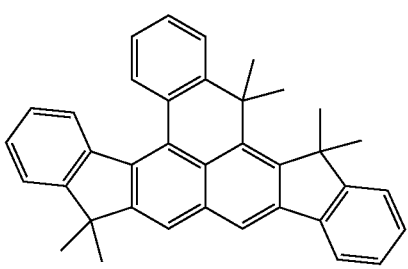

-continued
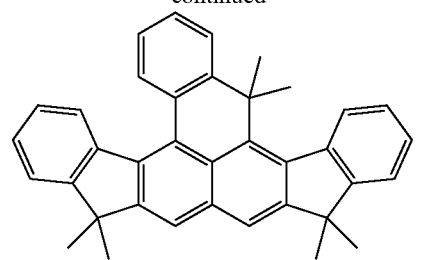
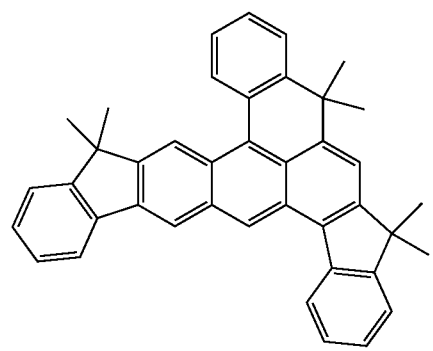
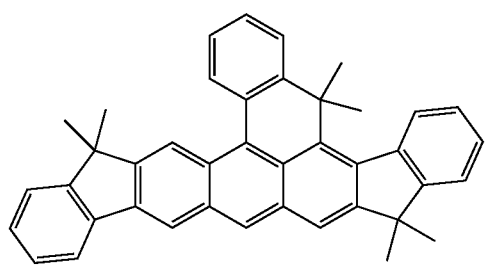
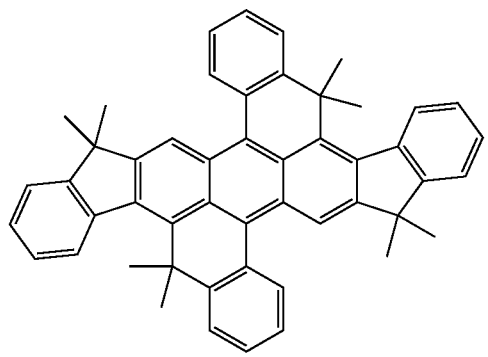
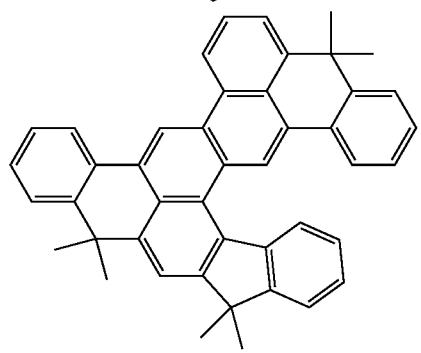
-continued
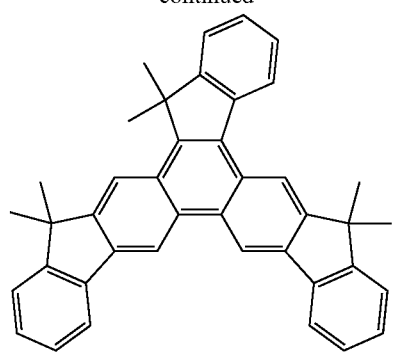
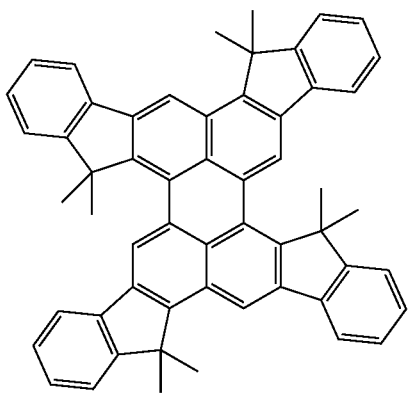
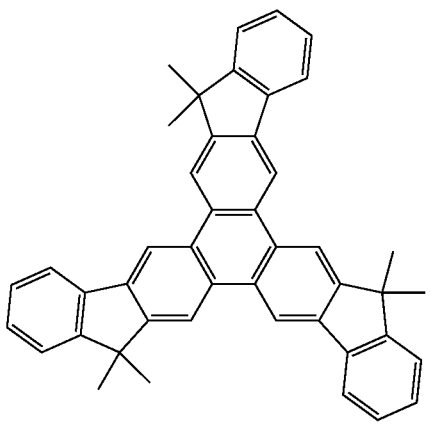
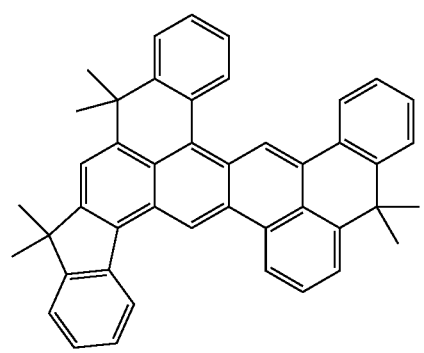

23
-continued
[Chem. 17-2]
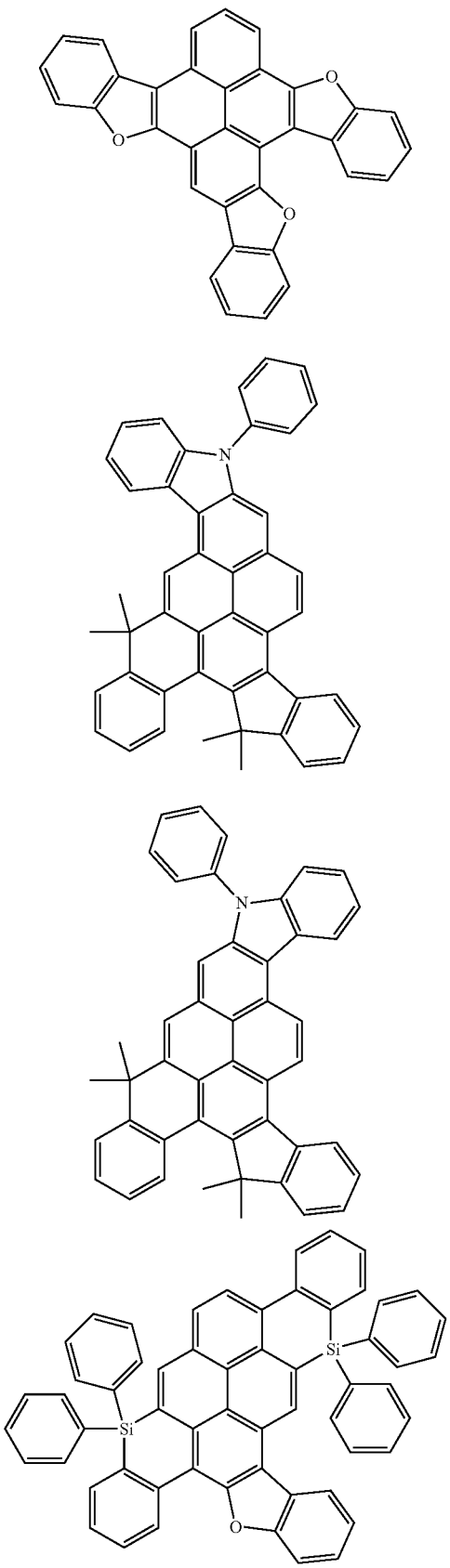
24
-continued
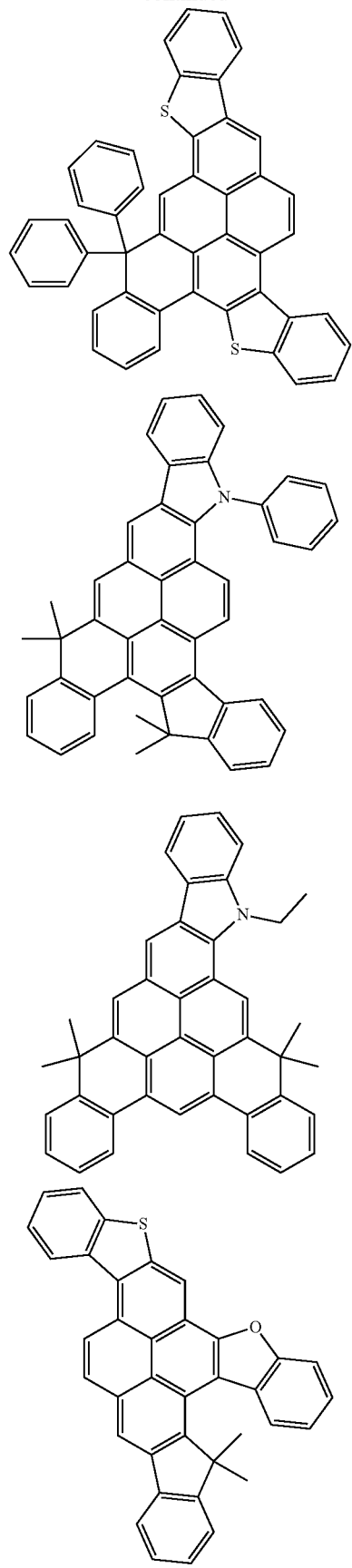

25
-continued
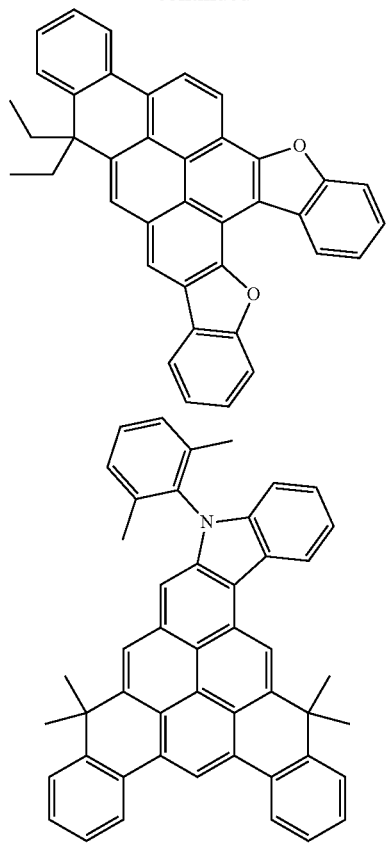
[Chem. 17-3]
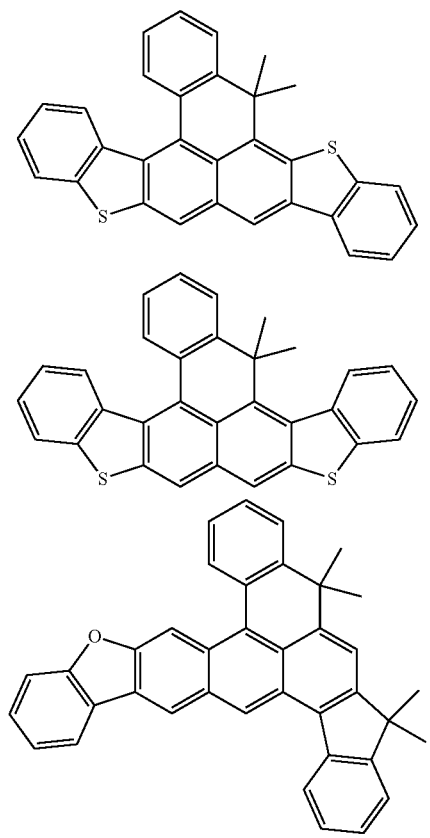
26
-continued
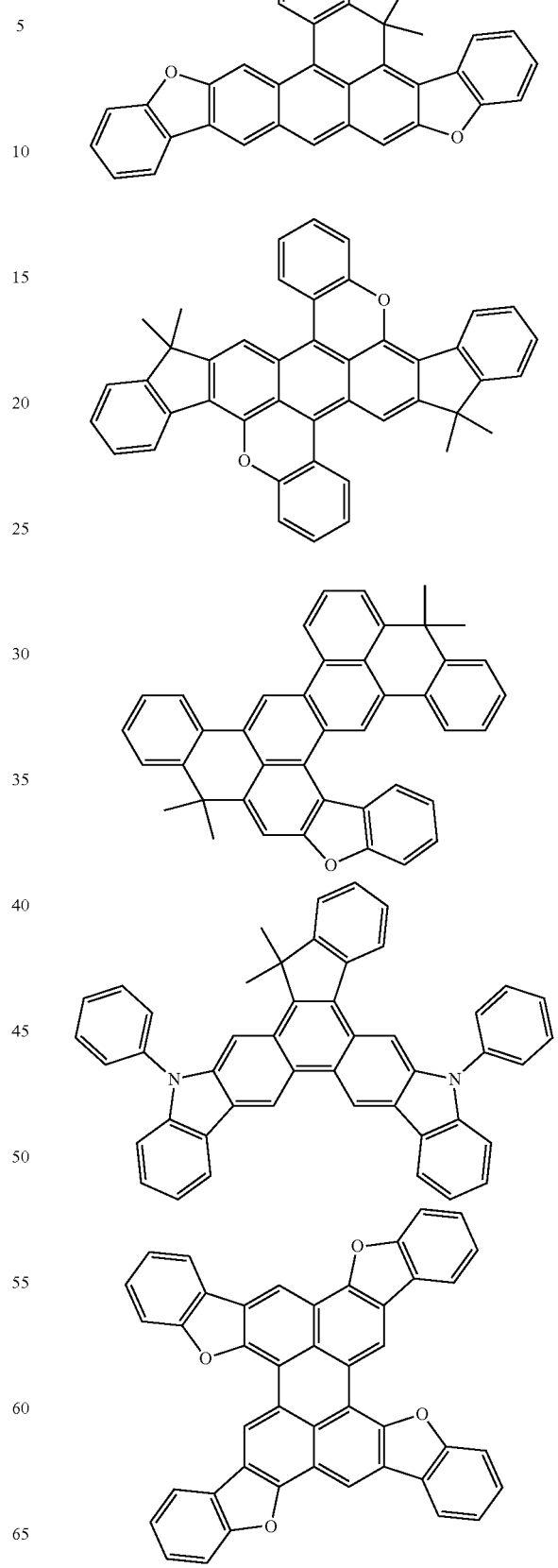

-continued

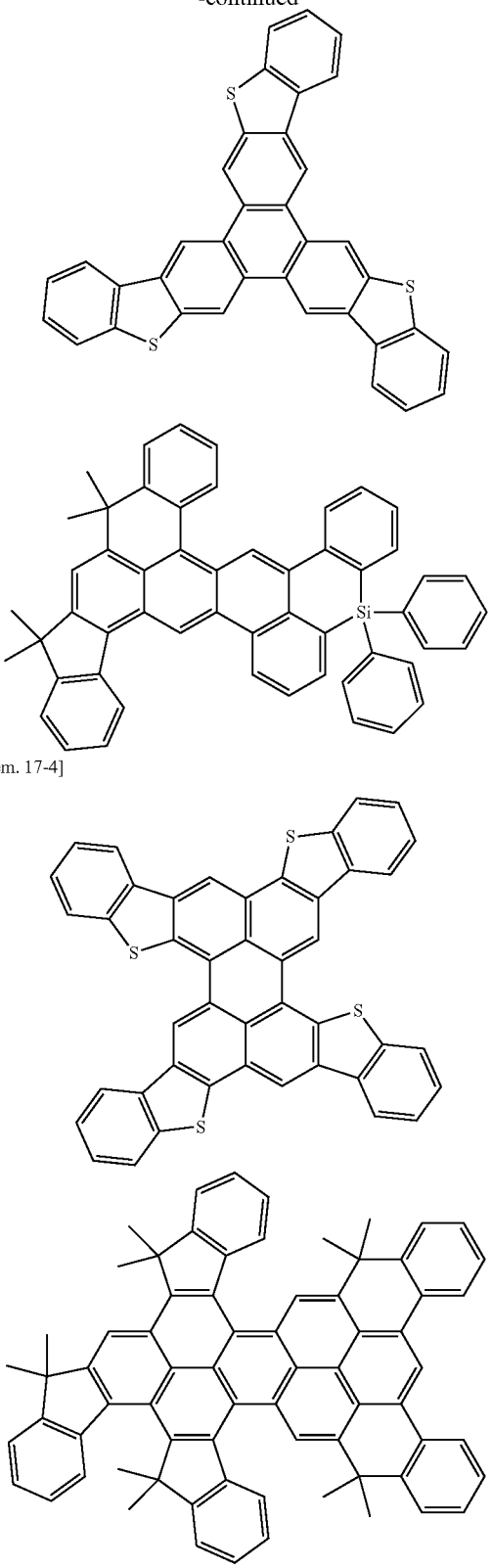

[Chem. 17-4]

The compound represented by the general formula (I) can be synthesized by the method described in US2008/0100208 or a combination of other known reactions. Further, for example, it can also be synthesized by the following scheme.

Scheme

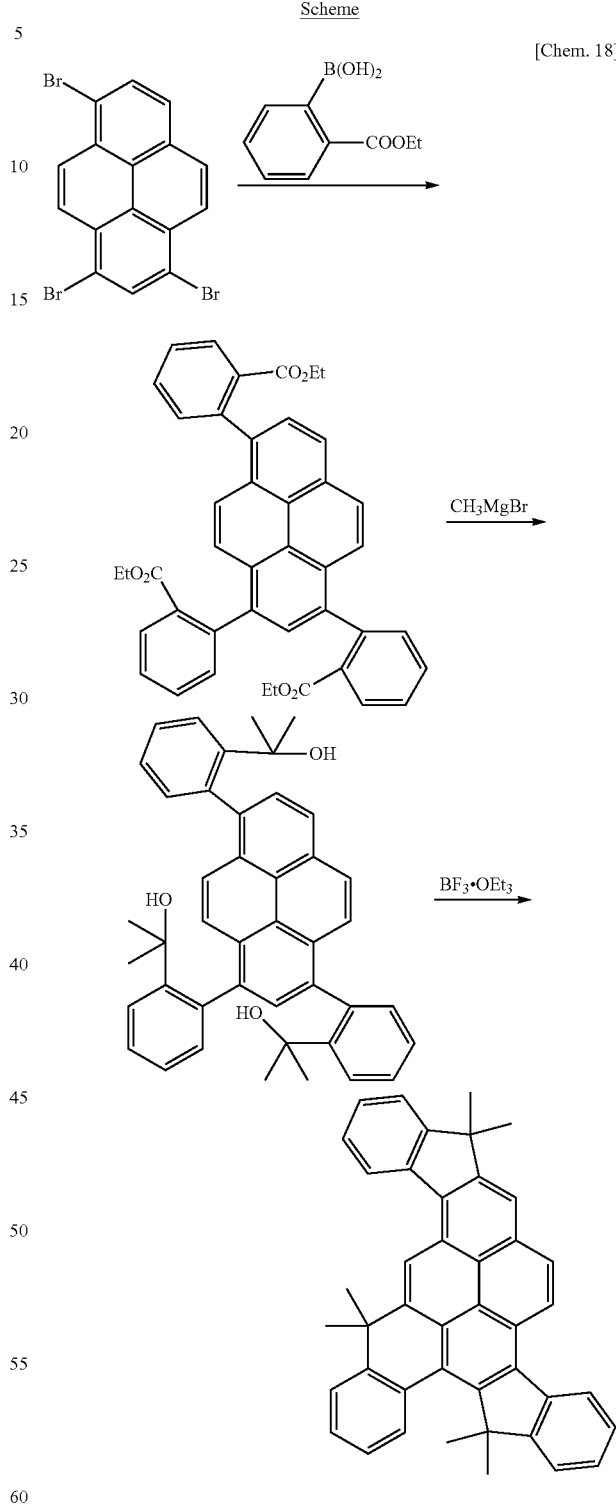

[Chem. 18]

After the synthesis, purification is preferably carried out by column chromatography, recrystallization, or the like, and then by sublimation purification. By the sublimation purification, organic impurities can be separated and inorganic salts, residual solvents, or the like can be removed effectively.

[Organic Electroluminescent Element]

The organic electroluminescent element of the present invention includes a substrate, a pair of electrodes including an anode and a cathode, disposed on the substrate, and at least one organic layer including a light emitting layer, disposed between the electrodes, in which at least one kind of compound represented by the general formula (I) is contained in any layer of the at least one organic layer.

The configuration of the organic electroluminescent element of the present invention is not particularly limited. FIG. 1 shows one example of the configuration of the organic electroluminescent element of the present invention. The organic electroluminescent element 10 in FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed descriptions described in this publication can be applied to the present invention.

Hereinafter, preferred aspects of the organic electroluminescent element of the present invention will be described in detail in the order of the substrate, the electrodes, the organic layer, a protective layer, a sealing enclosure, a driving method, a light emitting wavelength, and applications.

<Substrate>

The organic electroluminescent element of the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic electroluminescent element of the present invention has at least one organic layer including a light emitting layer, disposed between the electrodes, in which the compound represented by the general formula (I) is contained in at least one layer of the organic layers. For the organic electroluminescent element of the present invention, at least one organic layer including the compound represented by the general formula (I) is preferably a light emitting layer.

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in detail in order.

(Configuration of Organic Layer)

In the organic electroluminescent element of the present invention, the organic layer includes a light emitting layer. The organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element can be prepared with low cost and high efficiency.

The compound represented by the general formula (I) is contained in at least one of the organic layers disposed between the electrodes of the organic electroluminescent element, and preferably contained in the light emitting layer in the organic layer disposed between the electrodes.

However, so far as the gist of the present invention is not deviated, the compound represented by the general formula (I) may be contained in an organic layer other than the light emitting layer of the organic electroluminescent element of the present invention. Examples of the organic layer other than the light emitting layer, which may contain the compound represented by the general formula (I), include a hole injecting layer, a hole transporting layer, an electron transporting layer, an electron injecting layer, an exciton blocking layer, and a charge blocking layer (a hole blocking layer, an electron blocking layer, and the like), preferably any one of an exciton blocking layer, a charge blocking layer, an electron transporting layer, and an electron injecting layer, and more preferably an exciton blocking layer, a charge blocking layer, or an electron transporting layer.

In the case where the compound represented by the general formula (I) is contained in the light emitting layer, the compound represented by the general formula (I) is contained, preferably in the amount of 0.1% by mass to 100% by mass, more preferably 1% by mass to 50% by mass, and still more preferably 2% by mass to 20% by mass, with respect to the total mass of the light emitting layer.

In the case where the compound represented by the general formula (I) is contained in an organic layer other than the light emitting layer, the compound represented by the general formula (I) is contained in the organic layer, preferably in the amount of 70% by mass to 100% by mass, more preferably 80% by mass to 100% by mass, and still more preferably 90% by mass to 100% by mass, with respect to the total mass of the organic layers.

(Method for Forming Organic Layer)

The respective organic layers in the organic electroluminescent element of the present invention can be suitably formed by any of dry film forming methods such as a deposition method and a sputtering method, and wet type film forming methods (solution coating methods) such as a transfer method, a printing method, a spin coating method, and a bar coating method.

In the organic electroluminescent element of the present invention, it is preferable that the organic layer disposed between the pair of electrodes be formed by a vacuum deposition process or a wet process using a composition including the compound represented by the general formula (I) on at least one layer; it is more preferable that the light emitting layer be formed by a vacuum deposition process or a wet process; and it is particularly preferable that the light emitting layer be formed by deposition of a composition including the compound represented by the general formula (I).

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention may be constituted of only the light emitting material, or may be constituted as a mixed layer of a host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. The respective layers may include the same light emitting material or host material, and may also include a different material in every layer. In the case where a plurality of light emitting layers are present, the respective light emitting layers may emit light in a different luminous color from each other.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

In the organic electroluminescent element of the present invention, in a more preferred aspect, the light emitting layer contains the compound represented by the general formula (I), and the compound represented by the general formula (I) is used as the light emitting material of the light emitting layer. Here, the host material as referred to in the present specification is a compound which chiefly plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less, with respect to the total amount of light emission in the entirety of the element.

The compound represented by the general formula (I) may be used as a host material of the light emitting layer.

(Light Emitting Material)

In the organic electroluminescent element of the present invention, the compound represented by the general formula (I) is preferably used as the light emitting material, but in this case, a combination of the compound with light emitting materials different from the compound represented by the general formula (I) can be used. Further, in the organic electroluminescent element of the present invention, in the case where the compound represented by the general formula (I) is used as a host material of the light emitting layer or in the case where the compound represented by the general formula (I) is used in an organic layer other than the light emitting layer, the light emitting materials different from the compound represented by the general formula (I) are used in the light emitting layer.

The light emitting material which can be used in the present invention is a fluorescent light emitting material. Further, the light emitting layer in the present invention may contain two or more kinds of light emitting materials in order to improve the color purity or widen the light emitting wavelength region.

The fluorescent light emitting material and the phosphorescent material which can be used in the organic electroluminescent element of the present invention are described in detail in, for example, paragraph Nos. [0100] to [0164] of JP-A-2008-270736 and paragraph Nos. [0088] to [0090] of JP-A-2007-266458, the detailed descriptions thereon in these publications can be applied to the present invention.

Examples of the phosphorescent light emitting material which can be used in the present invention include phosphorescent light emitting materials described in patent documents, for example, U.S. Pat. Nos. 6,303,238, 6,097,147, WO00/57676, WO00/70655, WO01/08230, WO01/39234, WO01/41512, WO02/02714, WO02/15645, WO02/44189, WO05/19373, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Above all, examples of the light emitting material which is more preferred include phosphorescent light emitting metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, with Ir complexes, Pt complexes, and Re complexes being particularly preferred. Above all, Ir complexes, Pt complexes, and Re complexes each including at least one coordination mode of a metal-carbon bond, a metal-nitrogen bond, a metal-oxygen bond, and a metal-sulfur bond are preferred. Furthermore, from the viewpoints of luminous efficiency, driving durability, and chromaticity, Ir complexes and Pt complexes are particularly preferred, and Ir complexes are the most preferred.

The kind of the fluorescent light emitting material which can be used in the present invention is not particularly limited, but examples thereof include those other than the compound represented by the general formula (I), for example, benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bisstyrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in [0082] of JP-A-2010-111620 can also be used as a light emitting material.

The light emitting layer in the organic electroluminescent element of the present invention may be constituted with only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which does not have charge transporting properties and which does not emit light.

In addition, the light emitting layer may be made of a single layer or two or more layers. The respective layers may include the same light emitting materials or host materials, and may also include different materials from each other over layers. In the case where a plurality of light emitting layers are present, the respective light emitting layers may emit light in different luminous colors from each other.

(Host Material)

The host material is a compound that usually plays a role in injecting or transporting charges in the light emitting layer and is also a compound which does not substantially emit light in itself. As used herein, the statement "which does not substantially emit light" means that the amount of light emitting from the compound which does not substantially emit light is preferably 5% or less, more preferably 3% or less, and still more preferably 1% or less of the total amount of light emitting in the whole of the element.

Examples of the host material which can be used in the organic electroluminescent element of the present invention include the following compounds, other than compound represented by the general formula (I):

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin-based compounds, fused ring aromatic hydrocarbon compounds (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition, the compounds described in [0081] or [0083] of JP-A-2010-111620 can also be used.

Above all, carbazole, dibenzothiophene, dibenzofuran, arylamine, aromatic hydrocarbon compounds with fused rings, and metal complexes are preferred, and aromatic hydrocarbon compounds with fused rings are particularly preferred since they are stable. As the aromatic hydrocarbon compounds with fused rings, naphthalene-based compounds, anthracene-based compounds, phenanthrene-based compounds, triphenylene-based compounds, and pyrene-based compounds are preferred; anthracene-based compounds and pyrene-based compounds are more preferred; and anthracene-based compounds are particularly preferred. As the anthracene-based compounds, those described in [0033] to [0064] of WO 2010/134350 are particularly preferred, and examples thereof include Compounds H-1 and H-2 as described later.

The host material that can be used in the light emitting layer in the organic electroluminescent element of the present invention may be a host material having hole transporting properties or a host material having electron transporting properties.

In the light emitting layer, the singlet lowest excited energy ($S_1$ energy) in the film state of the host material is preferably higher than the $S_1$ energy of the light emitting material from the viewpoints of color purity, luminous efficiency, and driving durability. The $S_1$ of the host material is preferably higher than the $S_1$ of the light emitting material by 0.1 eV or more, more preferably by 0.2 eV or more, and still more preferably by 0.3 eV or more.

When $S_1$ in the film state of the host material is lower than $S_1$ of the light emitting material, the light emitting is lost, and thus, the host material is required to have higher $S_1$ than the light emitting material. Further, even in the case where the $S_1$ of the host material is higher than the $S_1$ of the light emitting material, a small difference in the $S_1$ of the both leads to partial reverse energy movement from the light emitting material to the host material, which causes reduction in efficiency, color purity, or durability. Therefore, there is a demand for a host material having a sufficiently high $S_1$, and high chemical stability and carrier injecting/transporting properties.

Furthermore, the content of the host compound in the light emitting layer in the organic electroluminescent element of the present invention is not particularly limited, but from the viewpoint of luminous efficiency and driving voltage, it is preferably from 15% by mass to 95% by mass, with respect to the total mass of the compounds forming the light emitting layer. When the light emitting layer includes a plurality of kinds of host compounds containing the compound represented by the general formula (I), the content of the compound represented by the general formula (I) is preferably from 50% by mass to 99% by mass, with respect to the total host compounds.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injecting layer/cathode, Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, Anode/hole injecting layer/hole transporting layer/blocking layer/light emitting layer/blocking layer/electron transporting layer/electron injecting layer/cathode.

The organic electroluminescent element of the present invention preferably includes at least one organic layer which is preferably disposed between the (A) anode and the light emitting layer. Examples of the organic layer which is preferably disposed between the (A) anode and the light emitting layer include an hole injecting layer, a hole transporting layer, and an electron blocking layer from the anode side.

The organic electroluminescent element of the present invention preferably includes at least one organic layer which is preferably disposed between the (B) cathode and the light emitting layer. Examples of the organic layer which is preferably disposed between the (B) cathode and the light emitting layer include an electron injecting layer, an electron transporting layer, and a hole blocking layer from the cathode side.

Specifically, an example of the preferred aspects of the organic electroluminescent element of the present invention is the aspect shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed Between Anode and Light Emitting Layer:

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one organic layer between the light emitting layer and the anode, and the organic layer preferably includes at least one compound of the compounds represented by the following general formulae (Sa-1), (Sb-1), and (Sc-1).

[Chem. 19]

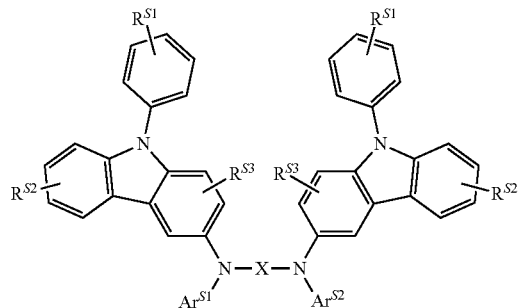

General formula (Sa-1)

(in which X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms.)

[Chem. 20]

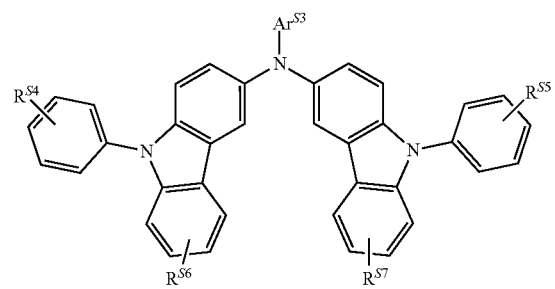

General formula (Sb-1)

(in which $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having 6 to 30 carbon atoms, or a substituted or unsubstituted heteroaryl group having 2 to 30 carbon atoms.)

[Chem. 21]

General formula (Sc-1)

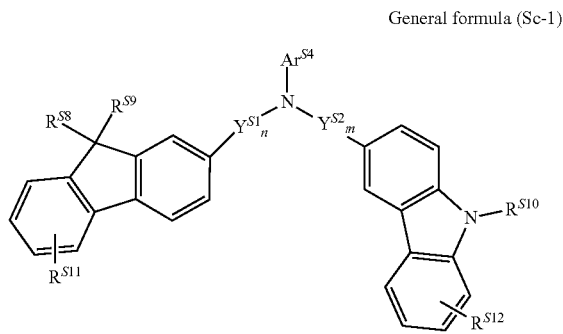

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted arylene group having 6 to 30 carbon atoms. n and m each independently represent an integer of 0 to 5.)

The general formula (Sa-1) will be described.

In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. X is preferably a substituted or unsubstituted arylene group having 6 to 30 carbon atoms, more preferably having a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$ and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably a substituted or unsubstituted phenyl group.

Next, the general formula (Sc-1) will be described.

In the general formula (Sc-1), $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S8}$ and $R^{S9}$ are preferably a substituted or unsubstituted alkyl group having 1 to 30 carbon atoms, or a substituted or unsubstituted aryl group having 6 to 30 carbon atoms, and more preferably a methyl group or a phenyl group. $R^{S10}$ is a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ represent a substituted or unsubstituted alkylene having 1 to 30 carbon atoms, or substituted or unsubstituted arylene having 6 to 30 carbon atoms. $Y^{S1}$ and $Y^{S2}$ are preferably a substituted or unsubstituted arylene having 6 to 30 carbon atoms, and more preferably a substituted or unsubstituted phenylene. n is an integer of 0 to 5, preferably 0 to 3, more preferably 0 to 2, and still more preferably 0. m is an integer of 0 to 5, preferably 0 to 3, more preferably 0 to 2, and still more preferably 1.

The general formula (Sa-1) is preferably a compound represented by the following general formula (Sa-2).

(in which $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Q^{Sa}$ each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sa-2) will be described. $R^{S1}$, $R^{S2}$, and $R^{S3}$ have the same definitions as those in the general formula (Sa-1), and their preferred ranges are also the same. Each $Q^{Sa}$ independently represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom or a substituted or unsubstituted alkyl group having 1 to 30 carbon atoms, and still more preferably a hydrogen atom.

[Chem. 22]

General formula (Sa-2)

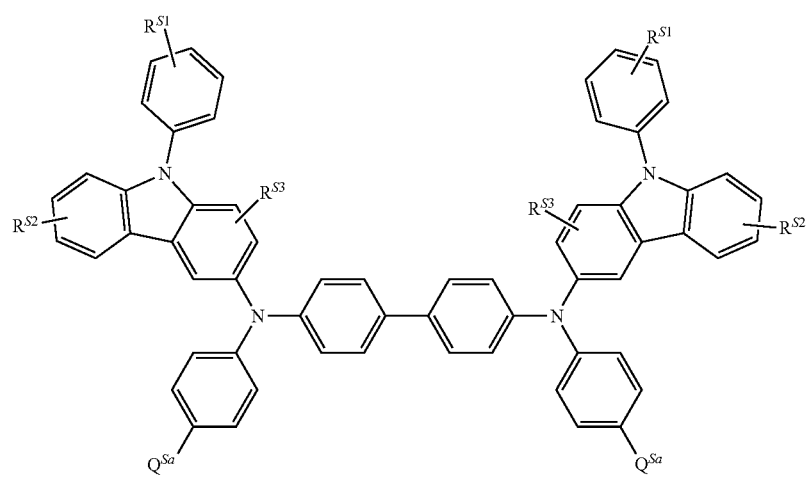

The general formula (Sb-1) is preferably a compound represented by the following general formula (Sb-2).

[Chem. 23]

General formula (Sb-2)

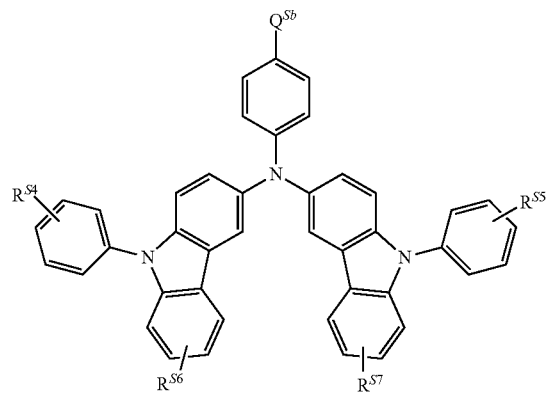

(in which $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. $Q^{S6}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sb-2) will be described. $R^{S4}$, $R^{S5}$, $R^{S6}$ and $R^{S7}$ have the same definitions as those in the general formula (Sb-1), and their preferred ranges are also the same. $Q^{Sa}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted alkyl group having 1 to 30 carbon atoms, and still more preferably a hydrogen atom.

The general formula (Sc-1) is preferably a compound represented by the following general formula (Sc-2).

[Chem. 24]

General formula (Sc-2)

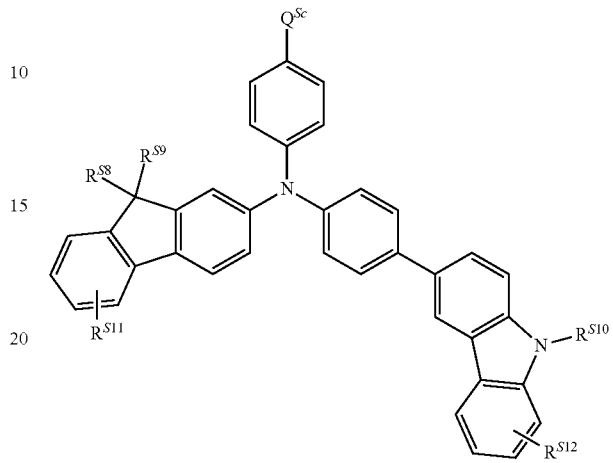

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sc-2) will be described. $R^{S8}$, $R^{S9}$, $R^{S10}$, $R^{S11}$ and $R^{S12}$ have the same definitions as those in the general formula (Sc-1), and their preferred ranges are also the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted aryl group having 6 to 30 carbon atoms, and still more preferably a phenyl group.

Specific examples of the compounds represented by the general formulae (Sa-1), (Sb-1), and (Sc-1) include the following ones. However, the present invention is not limited to the following specific examples.

[Chem. 25]

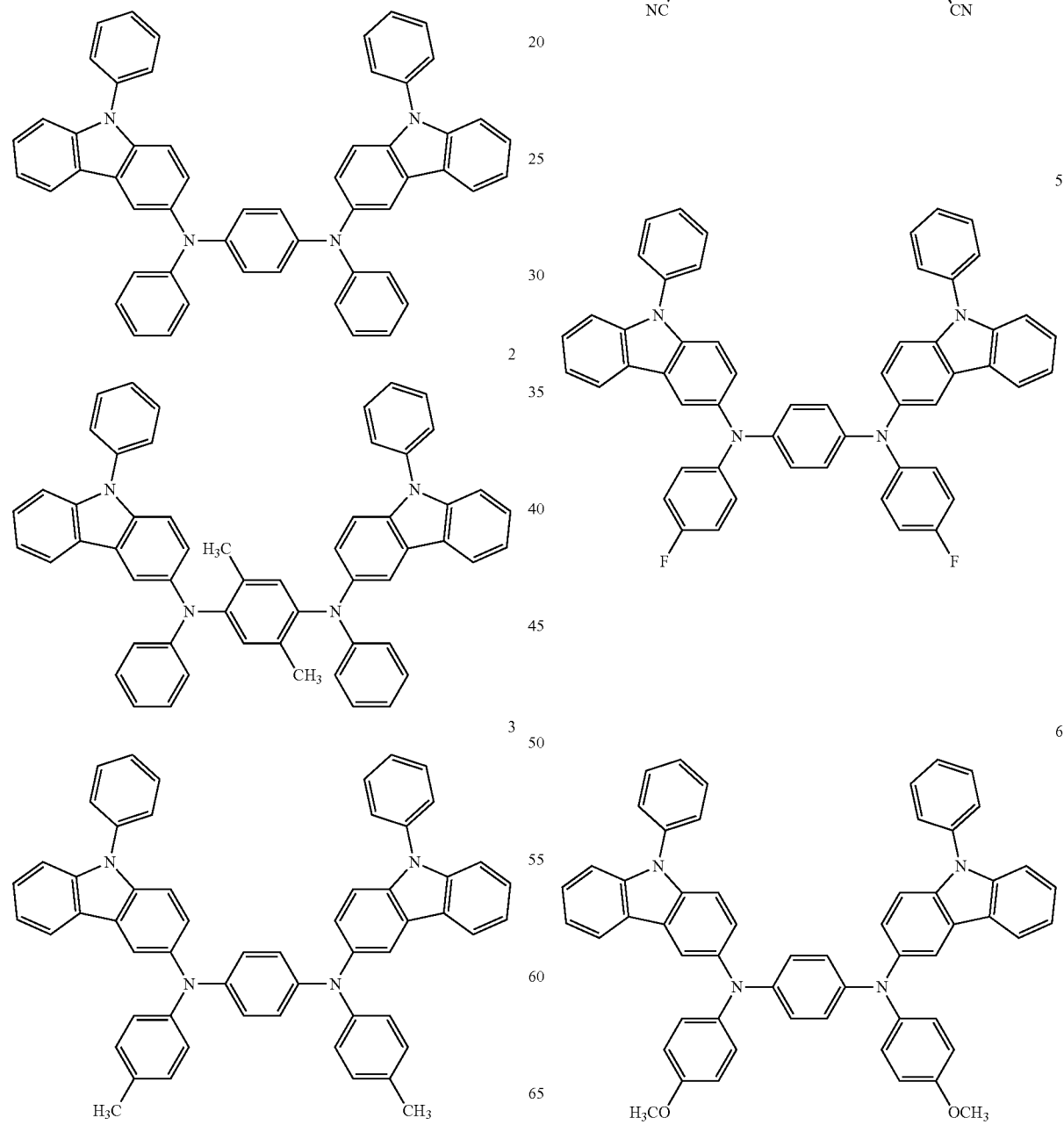

-continued
7
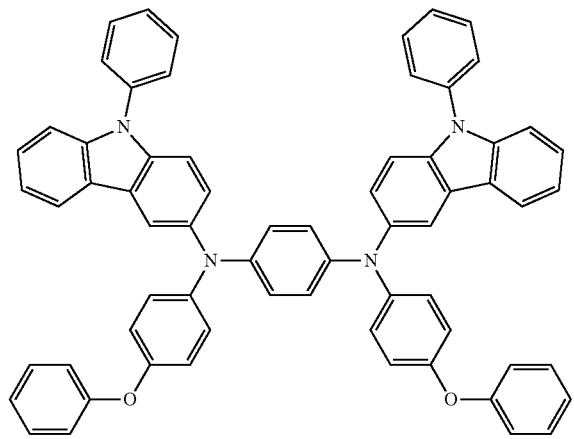
8
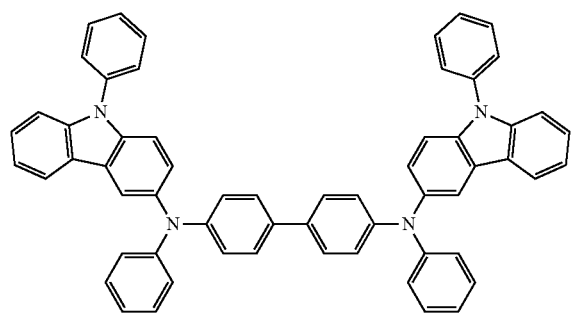
[Chem. 26]
9
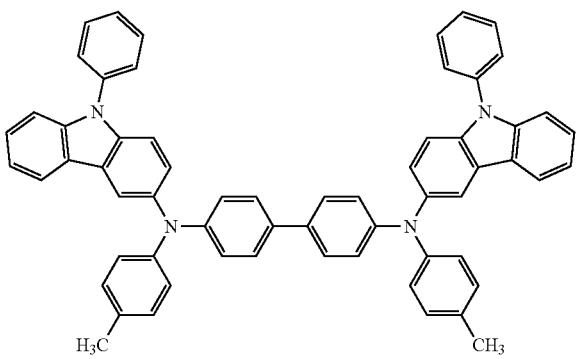
10
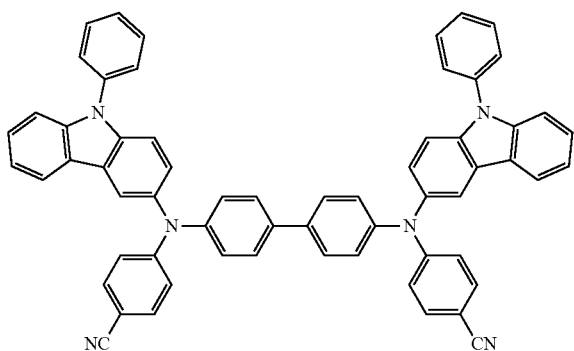
-continued
11
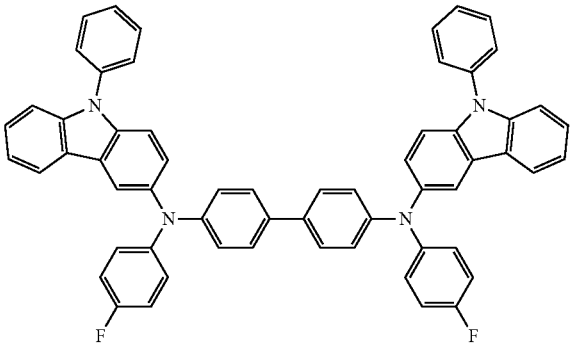
12
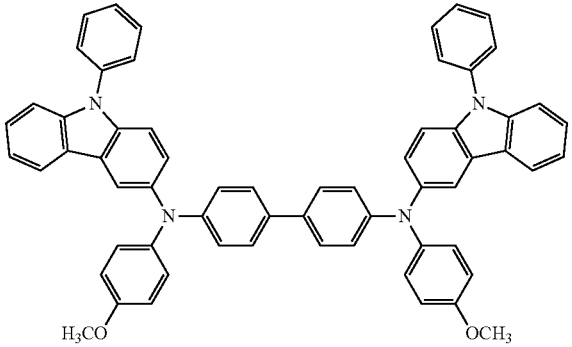
13
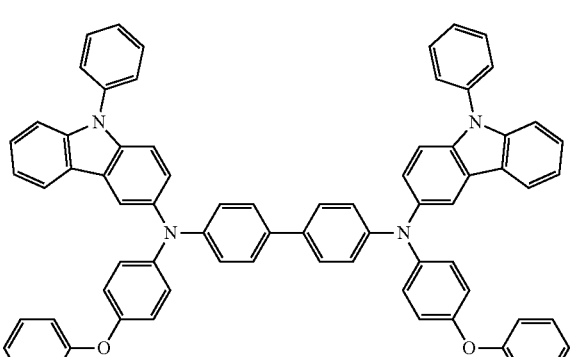
14
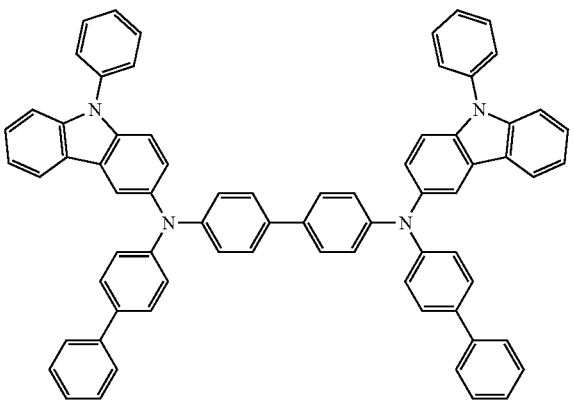

15
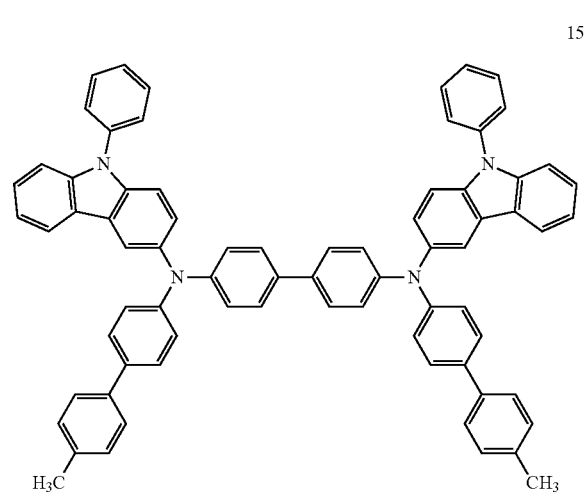
16
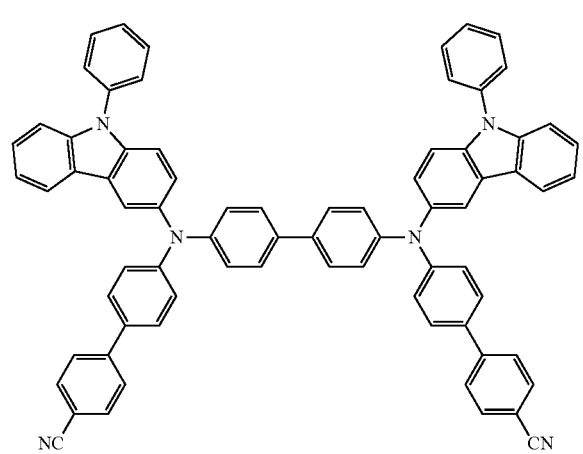
17
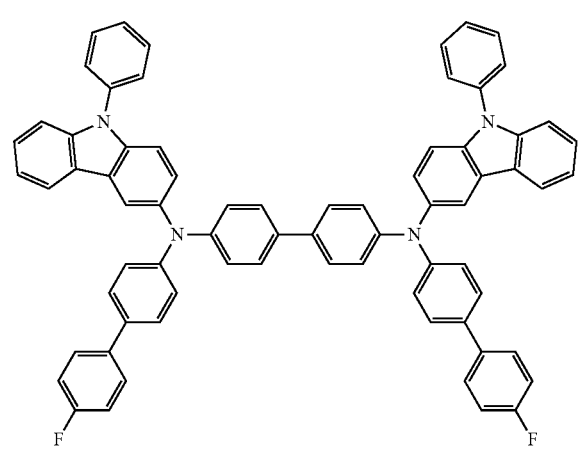
18
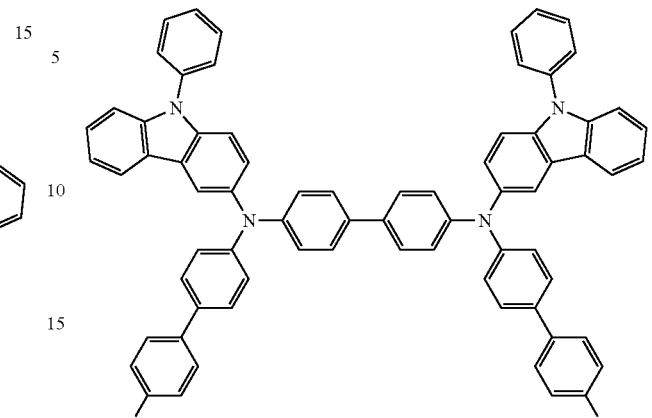
19
20

[Chem. 28]
21
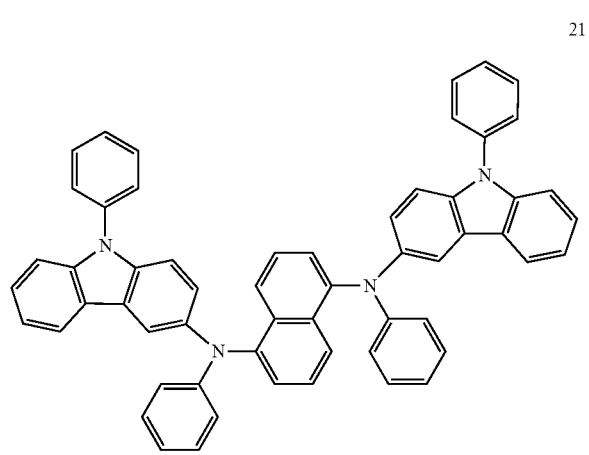
24
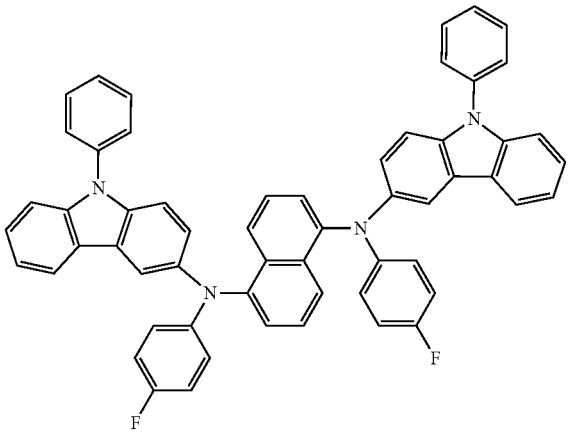
22
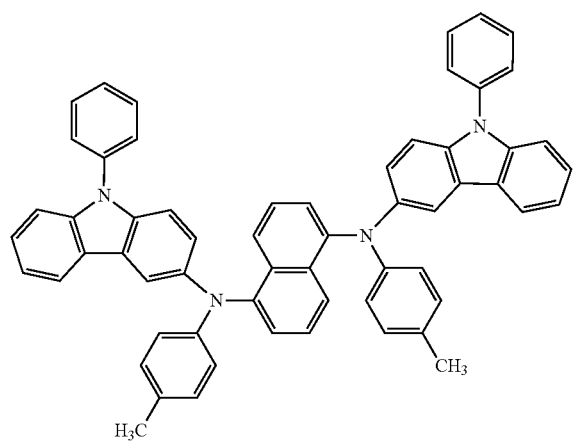
25
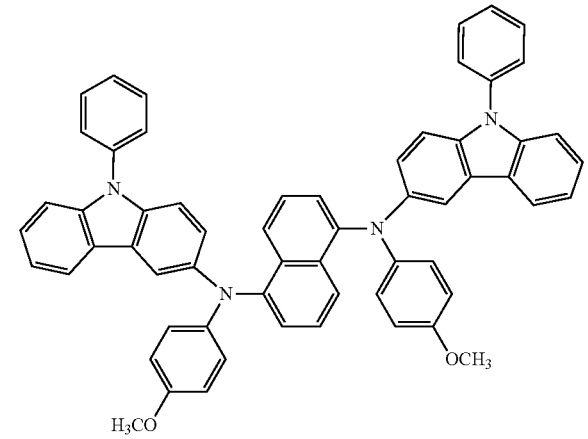
23
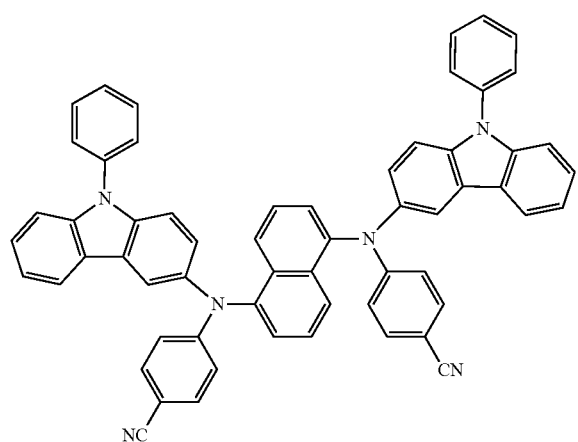
26
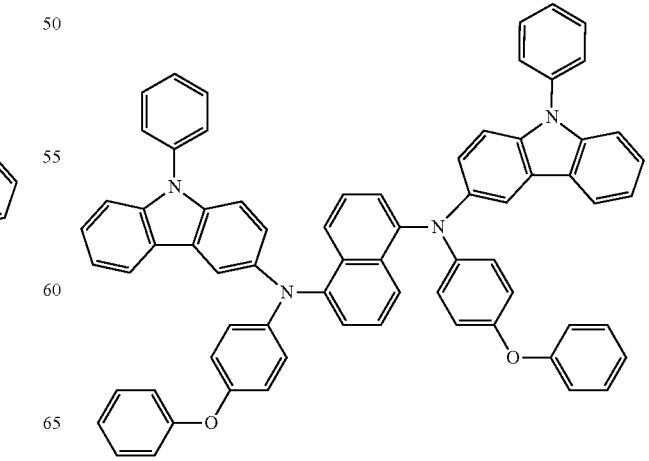

[Chem. 29]
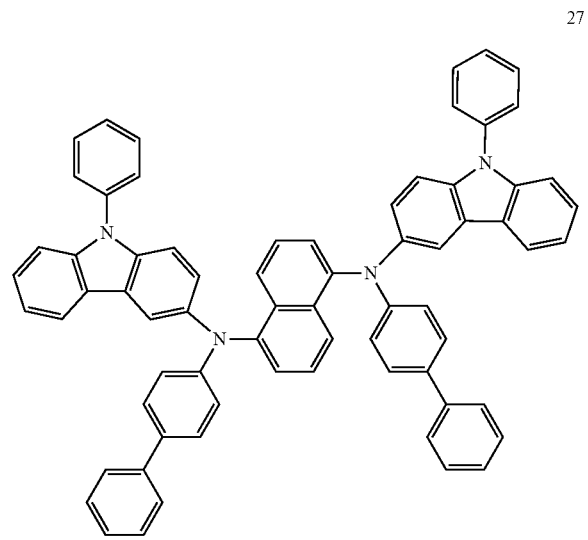
27
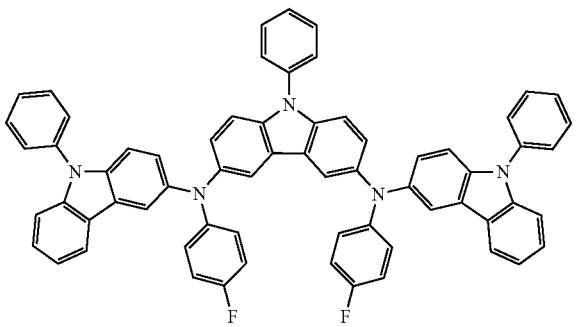
31
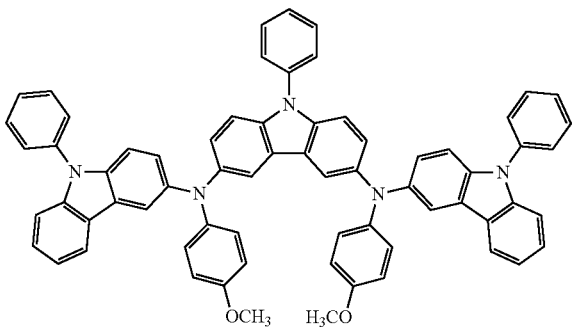
32
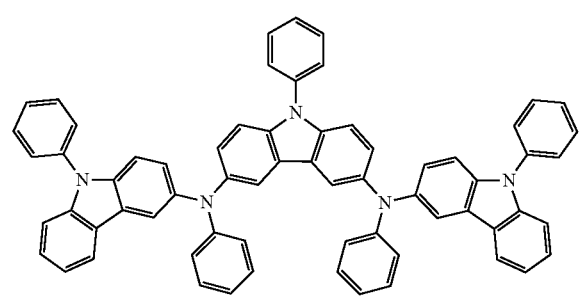
28
[Chem. 30]
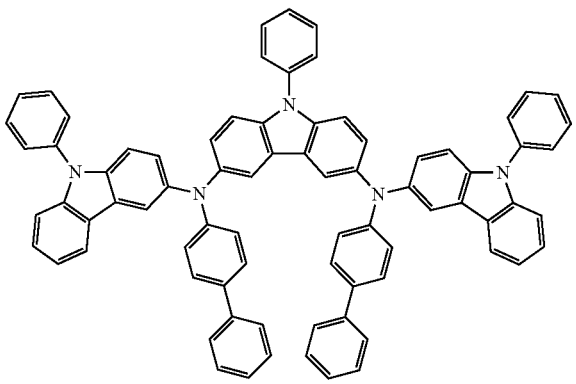
33
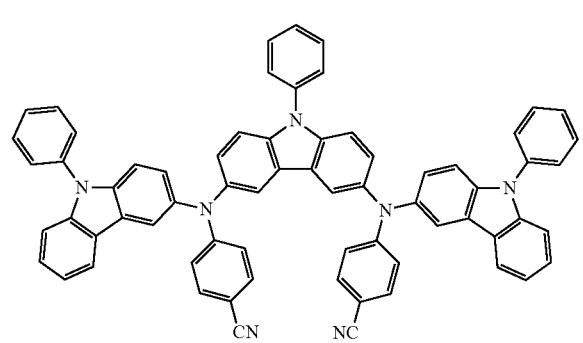
29
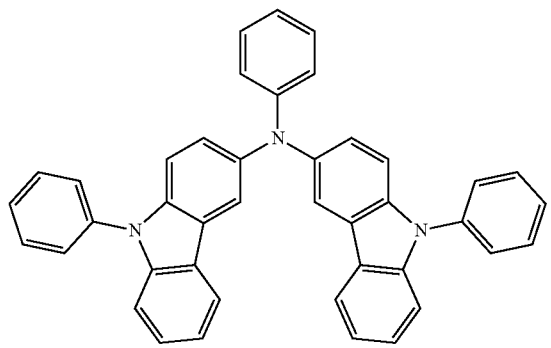
34
30

35
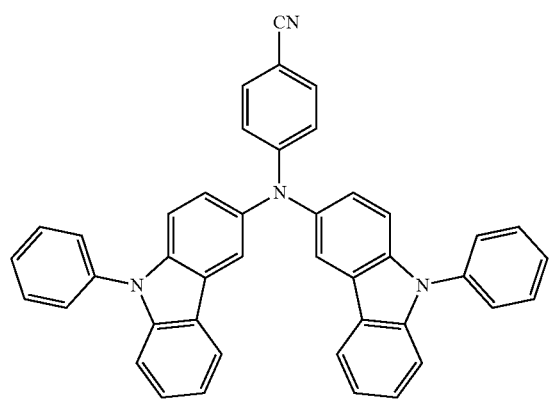
38
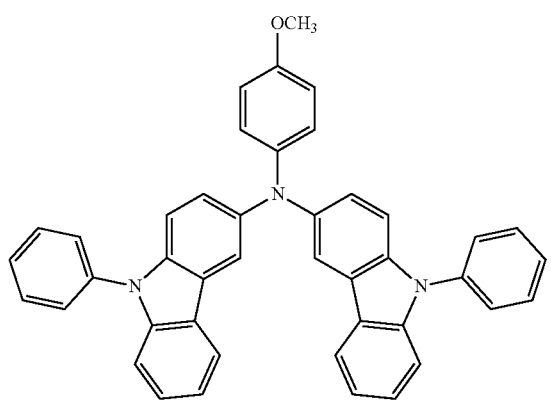
[Chem. 31]
36
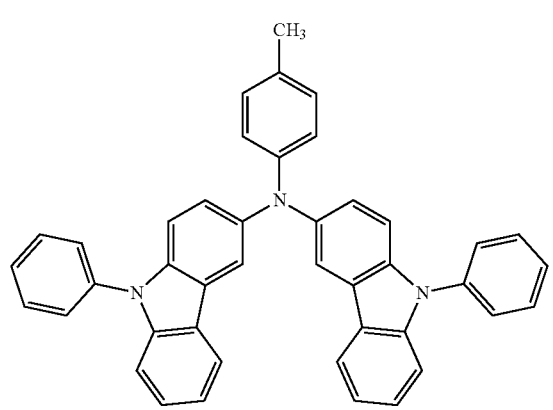
39
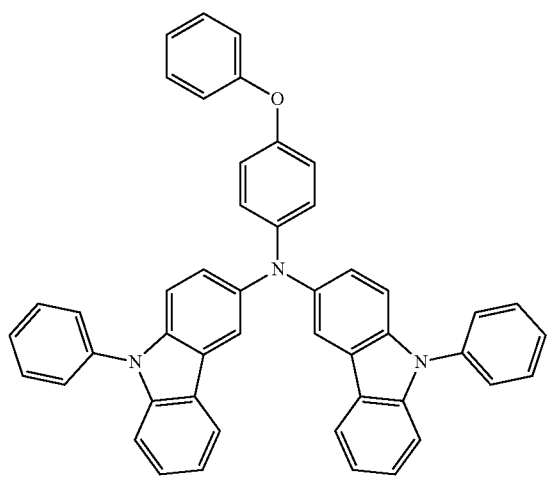
37
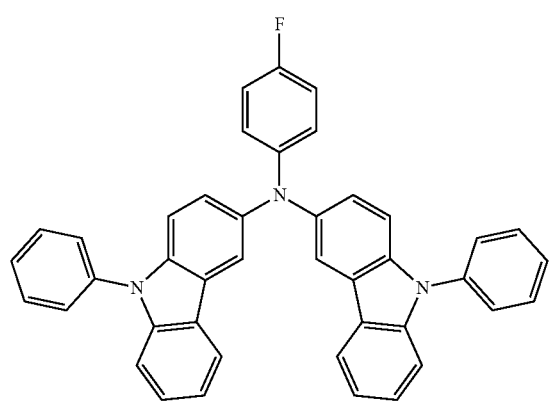
40
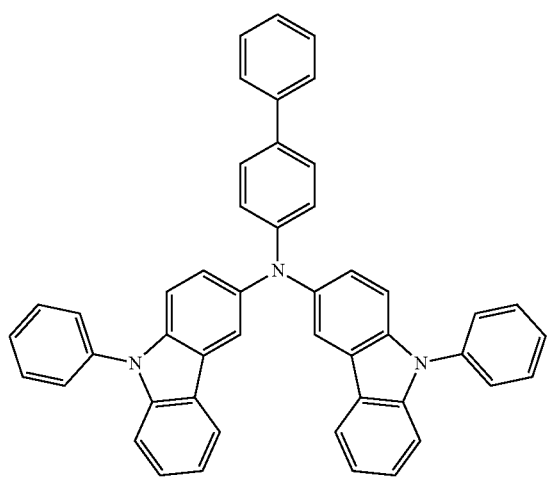

41
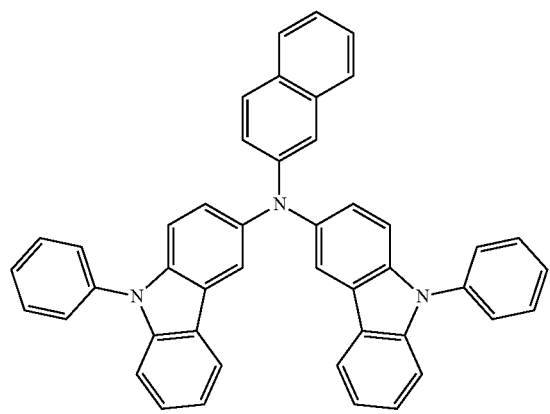
42
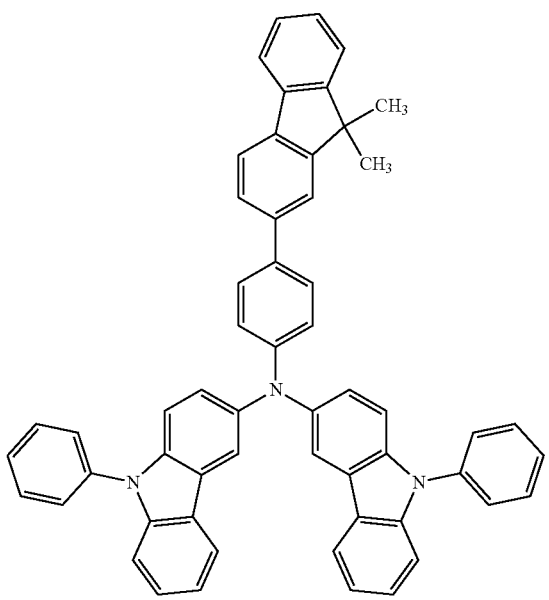
[Chem. 32]
43
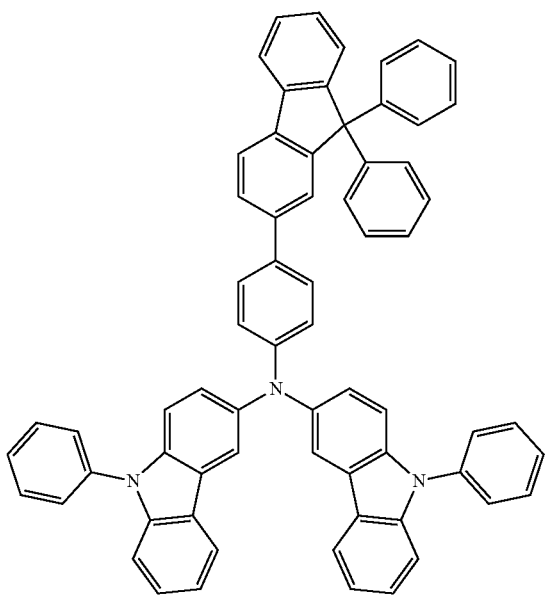
44
46
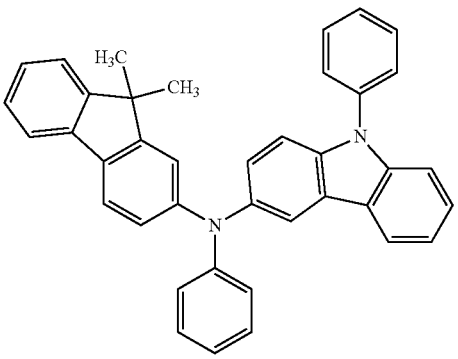

[Chem. 33]
47
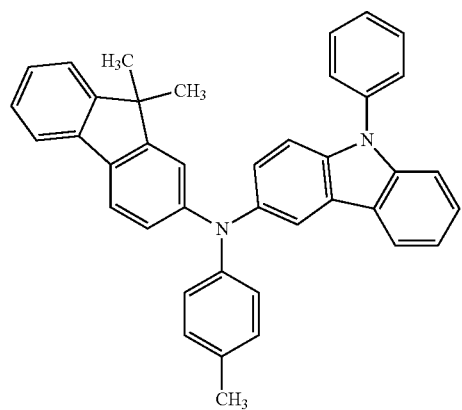
50
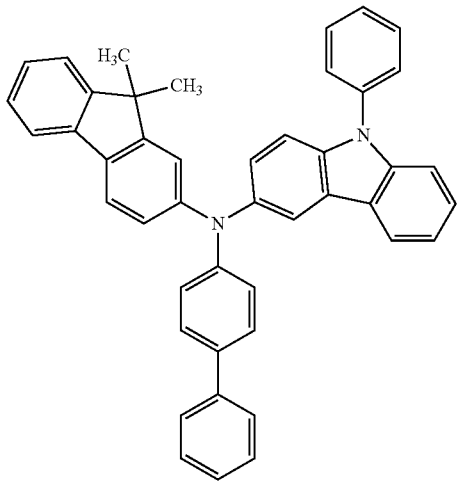
48
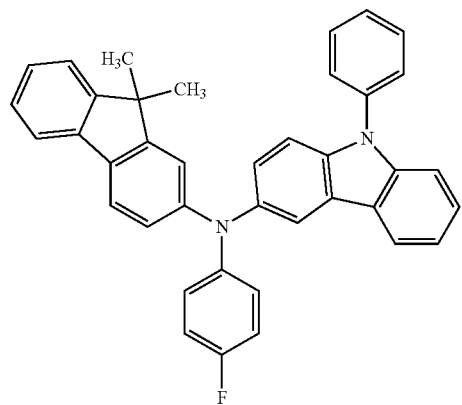
51
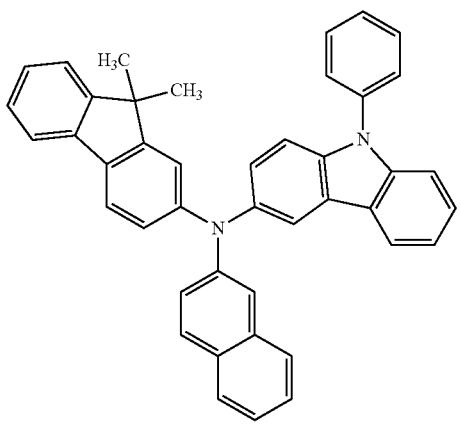
49
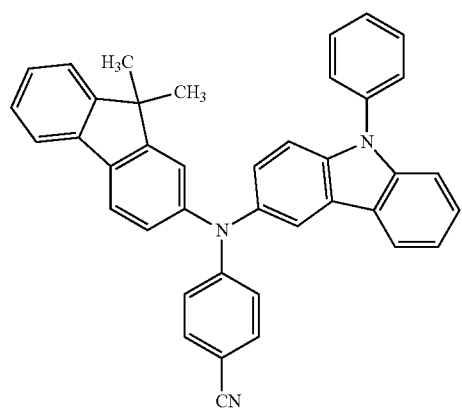
52
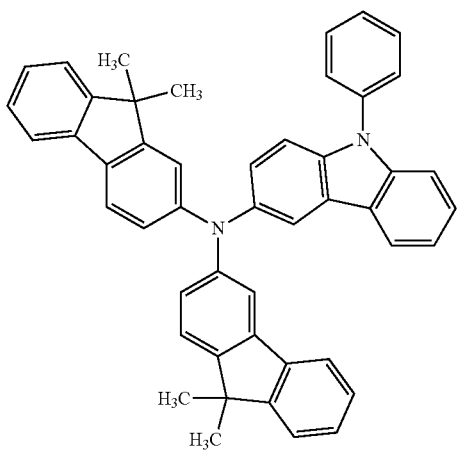

53
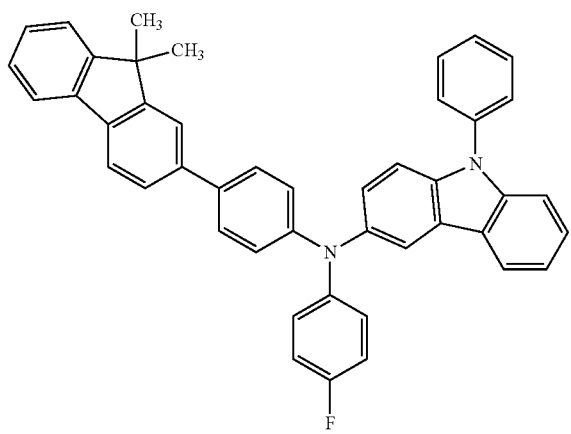
54
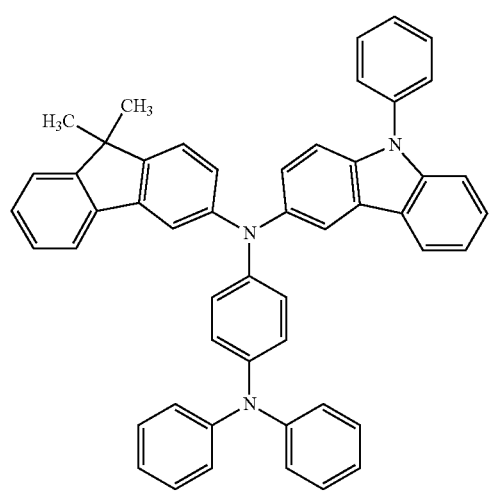
55
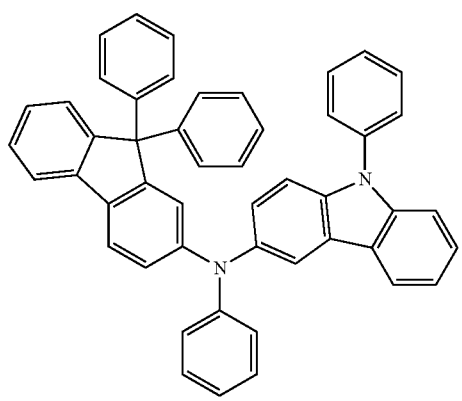
[Chem. 34]
56
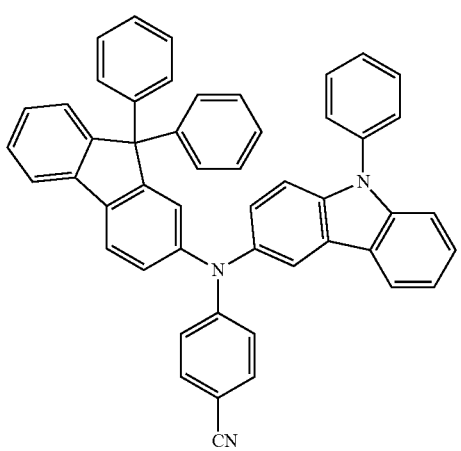
57
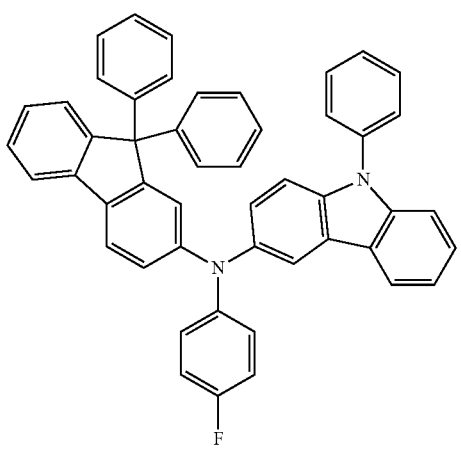
58
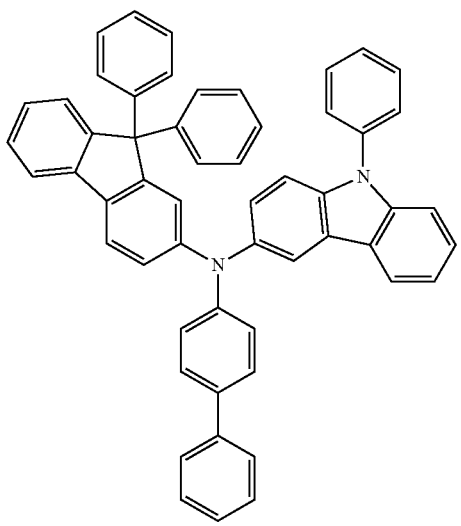

59

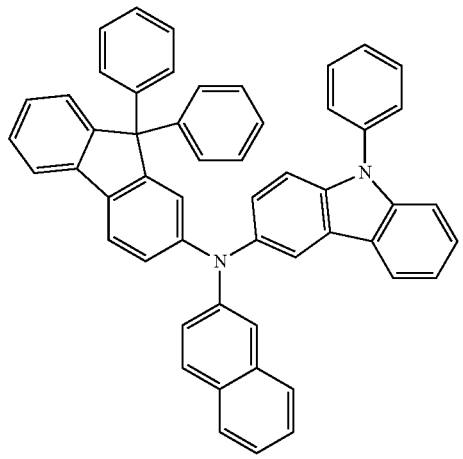

60

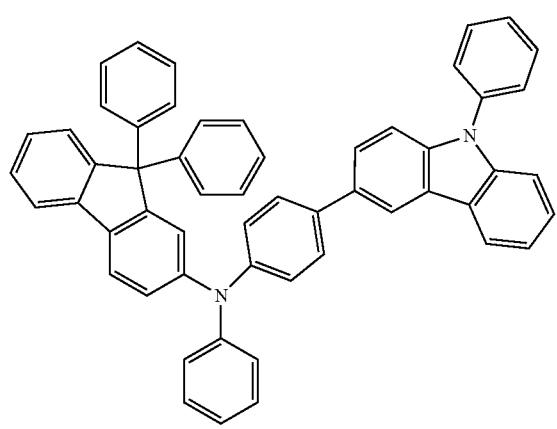

61

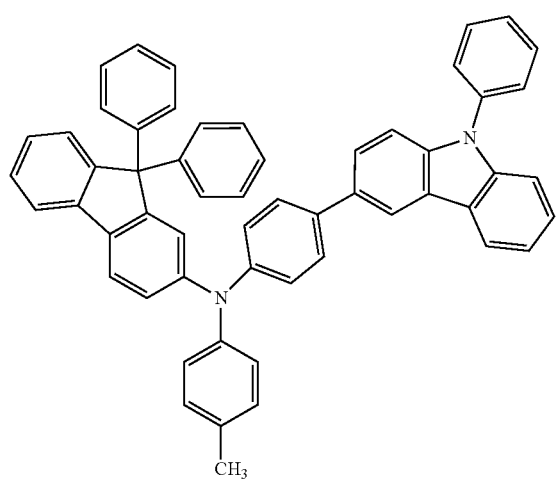

62

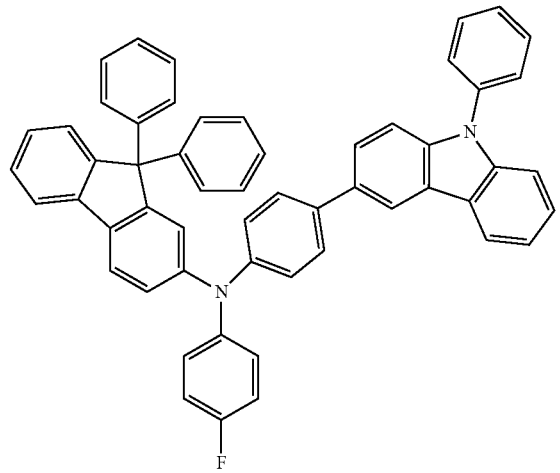

63

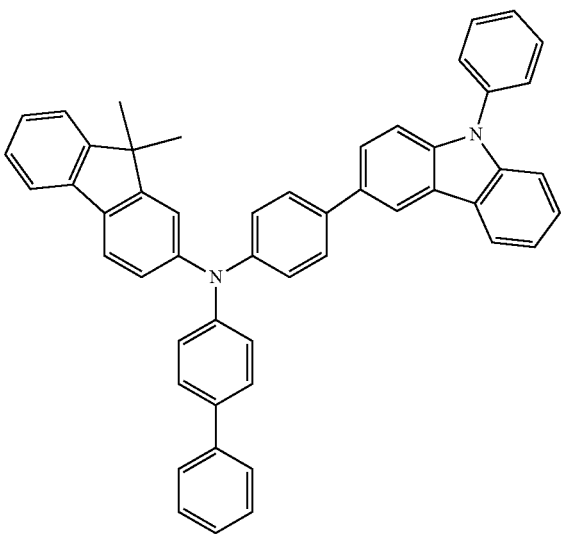

The compound represented by the general formula (Sa-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (Sa-1), (Sb-1), or (Sc-1) is preferably included in the organic layer between the light emitting layer and the anode, and above all, it is more preferably included in the layer on the anode side adjacent to the light emitting layer, and it is particularly preferably a hole transporting material included in the hole transporting layer.

The compound represented by the general formula (Sa-1), (Sb-1), or (Sc-1) is preferably contained in the amount of 70% by mass to 100% by mass, and more preferably 85% by mass to 100% by mass, with respect to the total mass of the organic layer added.

In addition, with respect to the hole injecting layer and the hole transporting layer, the detailed descriptions in paragraph Nos. [0165] to [0167] of JP-A-2008-270736 can be applied to the present invention.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include TCNQ compounds such as tetracyanoquinodimethane (TCNQ), tetrafluorotetracyanoquinodimethane ($F_4$-TCNQ), hexaazatriphenylene compounds such as hexacyanohexaazatriphenylene (HAT-CN), and molybdenum oxide.

The electron receptive dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer (A-2) Electron Blocking Layer The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or two or more kinds of materials selected from the above-exemplified materials or a multilayer structure composed of a plurality of layers having the same composition or different compositions.

The material used in the electron blocking layer preferably has higher $S_1$ energy than that of the light emitting material from the viewpoints of color purity, luminous efficiency, and driving durability. The $S_1$ in the film state of the material used in the electron blocking layer is preferably higher than the $S_1$ of the light emitting material by 0.1 eV or more, more preferably by 0.2 eV or more, and still more preferably by 0.3 eV or more.

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (I) can be used. As the other electron transporting materials, any one selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole, hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

As an example of the organic compound constituting the hole blocking layer, for example, the compound represented by the general formula (I) can be used.

Examples of the organic compounds constituting the hole blocking layer, other than the compound represented by the general formula (I), include aluminum complexes such as aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or two or more kinds of the above-described materials or a multilayer structure composed of a plurality of layers having the same composition or different compositions.

The material used in the hole blocking layer preferably has higher $S_1$ energy than that of the light emitting material from the viewpoints of color purity, luminous efficiency, and driving durability. The $S_1$ in the film state of the material used in the hole blocking layer is preferably higher than the $S_1$ of the light emitting material by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, examples of the material which is particularly preferably used in the (B) materials for an organic layer, preferably disposed between the cathode and the light emitting layer include the compound represented by the general formula (I), a compound represented by the following general formula (O-1), and a compound represented by the following general formula (P).

Hereinafter, a compound represented by the general formula (O-1) and a compound represented by the general formula (P) will be described.

The organic electroluminescent element of the present invention preferably includes at least one organic layer between the light emitting layer and the cathode, and the organic layer preferably contains at least one of compounds represented by the following general formula (O-1), from the viewpoint of efficiency or driving voltage of an element. Hereinafter, the general formula (O-1) will be described.

[Chem. 35]

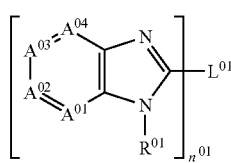

General formula (O-1)

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$'s may be the same as or different from each other. $L^{O1}$ represents any of divalent to hexavalent linking groups with an aryl ring or a heteroaryl ring. $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferably an alkyl group and an aryl group, and still more preferably an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^4$ or a nitrogen atom. It is preferable that 0 to 2 groups out of $A^{O1}$ to $A^{O4}$ be nitrogen atoms; and it is more preferable that 0 or 1 group out of $A^{O1}$ to $A^{O4}$ be nitrogen atoms. It is preferable that all of $A^{O1}$ to $A^{O4}$ be C—$R^4$, or $A^{O1}$ be a nitrogen atom, and $A^{O2}$ to $A^{O4}$ are C—$R^4$; it is more preferable that $A^{O1}$ be a nitrogen atom, and $A^{O2}$ to $A^{O4}$ be C—$R^4$; it is still more preferable that $A^{O1}$ be a nitrogen atom, $A^{O2}$ to $A^{O4}$ be C—$R^4$, and $R^4$'s be all hydrogen atoms.

$R^4$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, a plurality of $R^4$'s may be the same as or different from each other. $R^4$ is preferably a hydrogen atom or an alkyl group, and more preferably a hydrogen atom.

$L^{O1}$ represents any of a divalent to hexavalent linking group including an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

[Chem. 36]

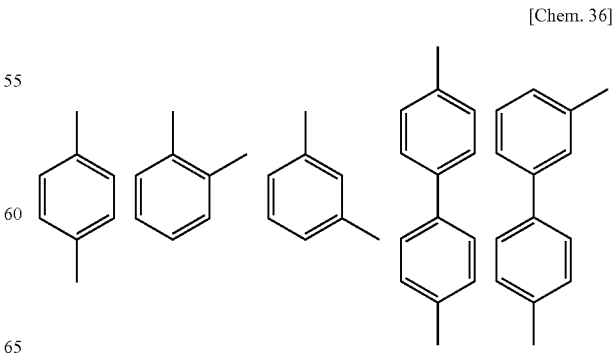

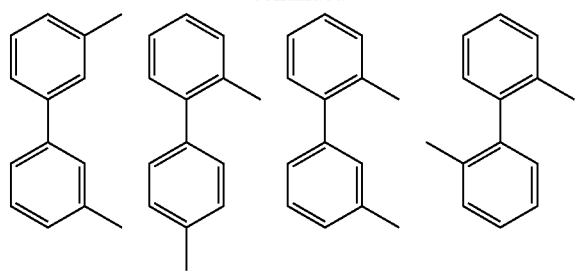
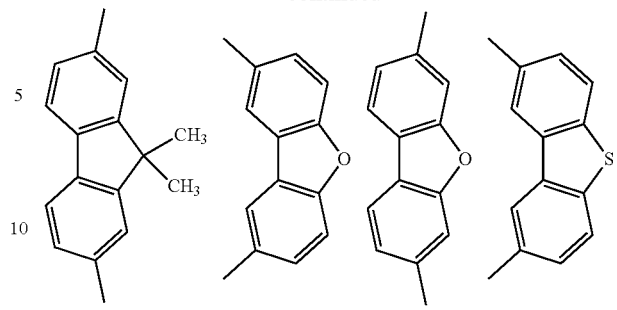
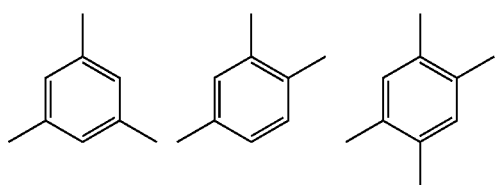
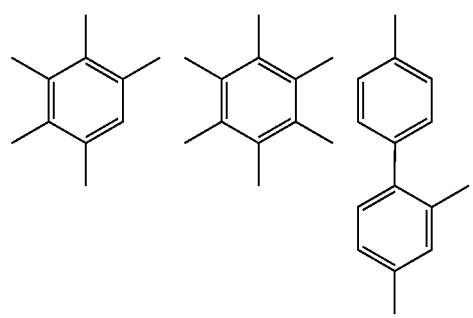
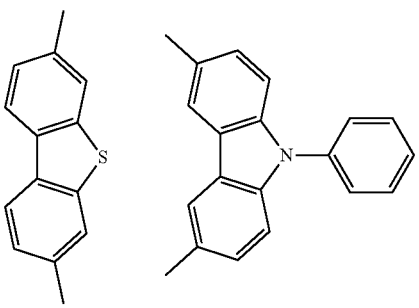
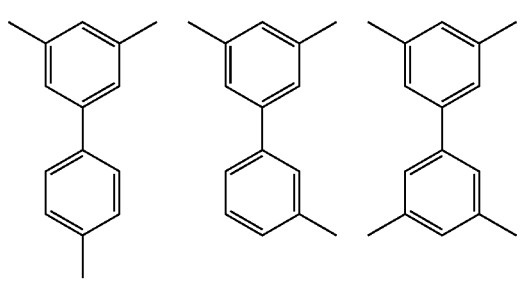
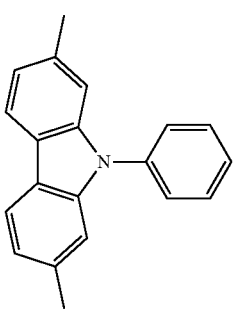
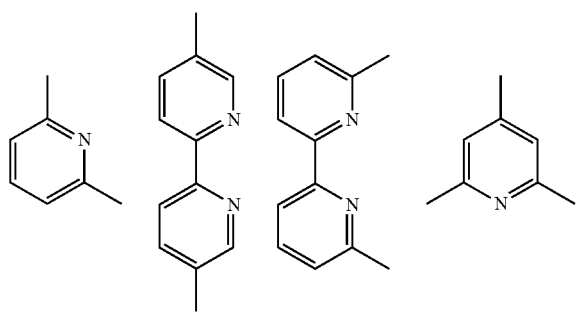
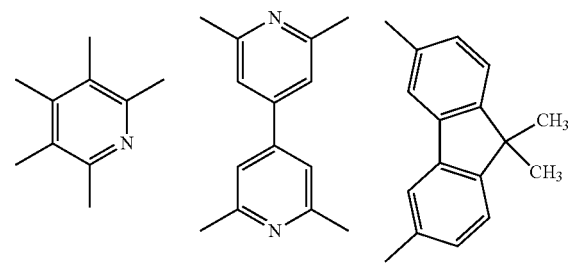

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., still more preferably from 130° C. to 300° C., and even still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but the compound represented by the general formula (O-1), which can be used in the present invention, should not be construed to be limited to the specific examples.

[Chem. 37]
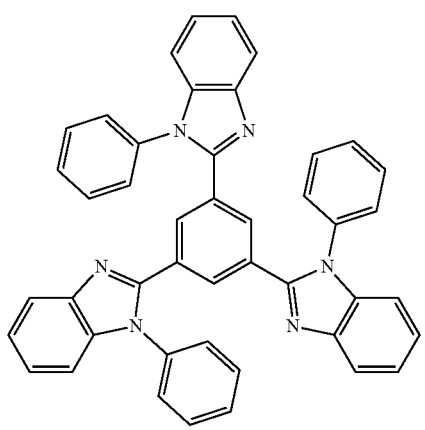
OM-1
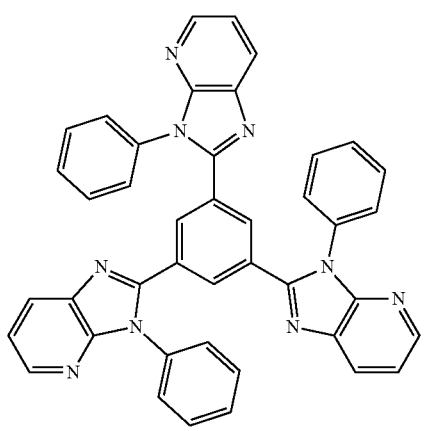
OM-2
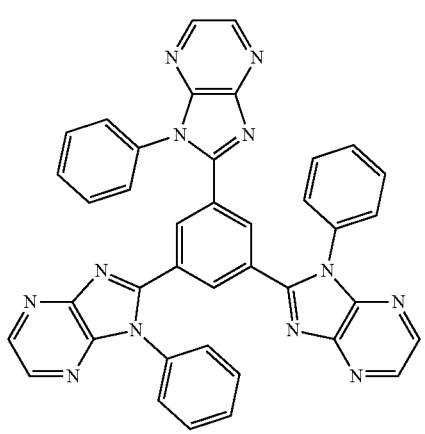
OM-3
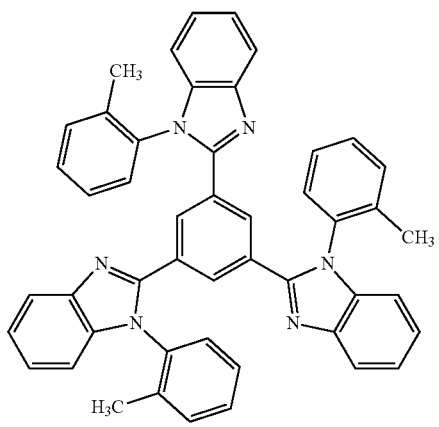
OM-4
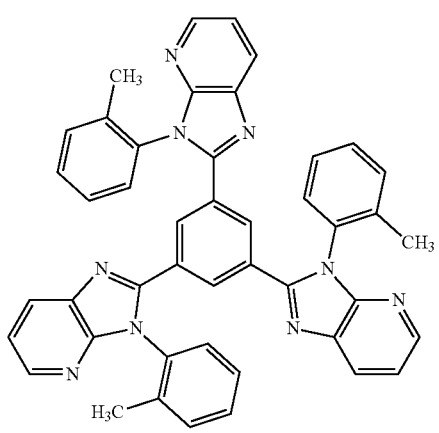
OM-5
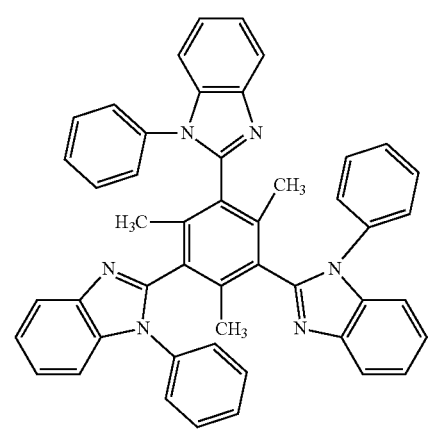
OM-6

OM-7
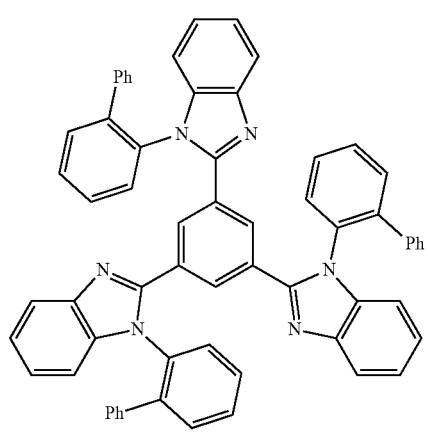
OM-8
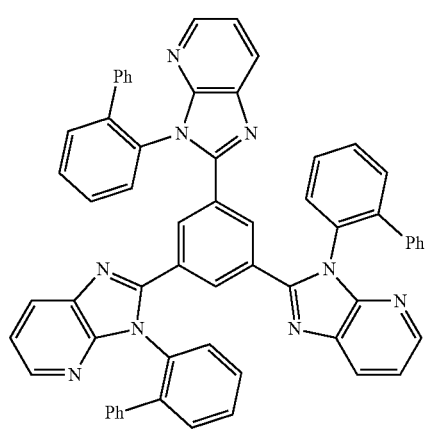
OM-9
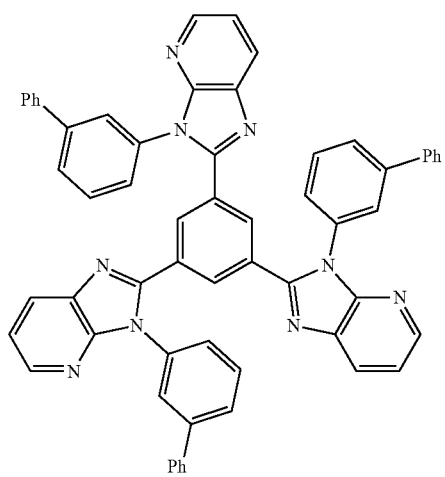
[Chem. 38]
OM-10
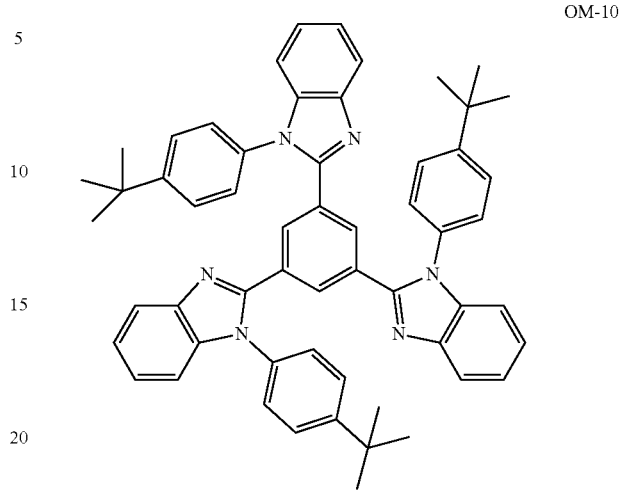
OM-11
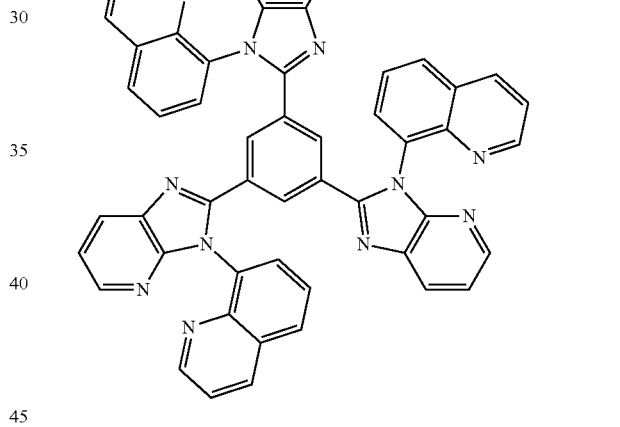
OM-12
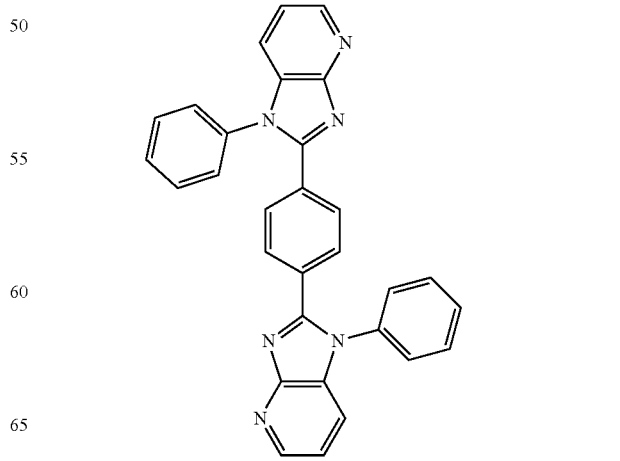

OM-13

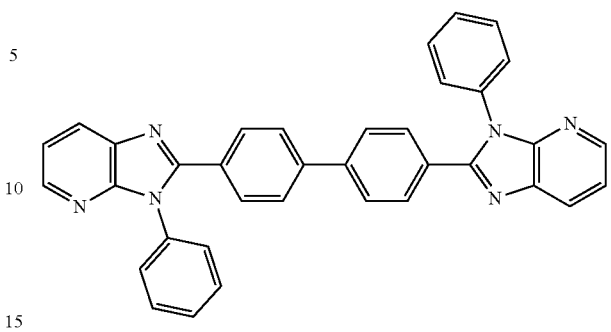

OM-16

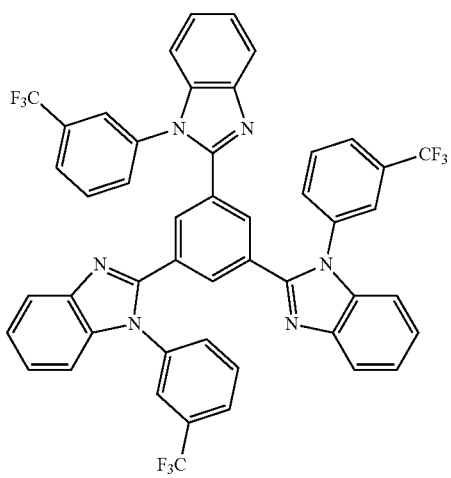

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably included in the organic layer between the light emitting layer and the cathode, however, it is more preferably included in the layer on the cathode side adjacent to the light emitting layer.

The compound represented by the general formula (O-1) is preferably contained in the amount of 70% by mass to 100% by mass, and more preferably 85% by mass to 100% by mass, with respect to the total mass of the organic layer added.

The organic electroluminescent element of the present invention preferably includes at least one layer of organic layers between the light emitting layer and the cathode, and it is preferable that the organic layer contain at least one of compounds represented by the following general formula (P), from the viewpoint of efficiency or the driving voltage of an element. Hereinafter, the general formula (P) will be described.

OM-14

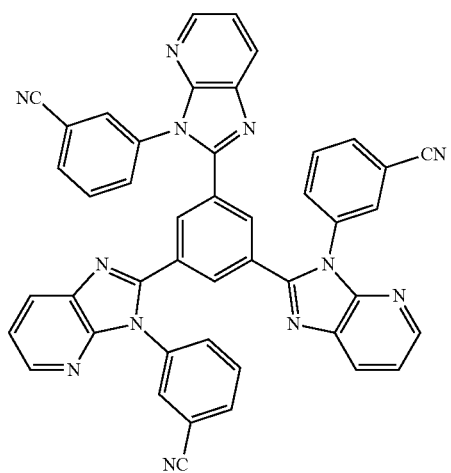

[Chem. 39]

OM-15

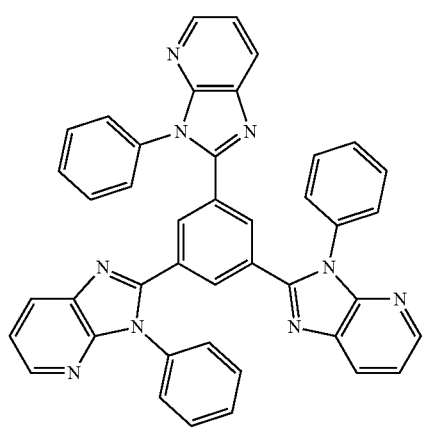

General formula (P)

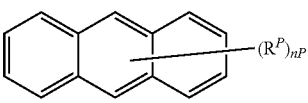

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. nP represents an integer of 1 to 10, and in the case where there are a plurality of $R^P$'s, these may be the same as or different from each other. At least one of $R^P$'s is a substituent represented by the following general formulae (P-1) to (P-3).

[Chem. 40]

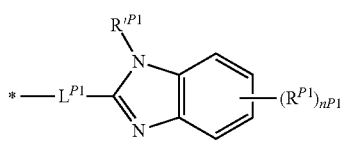
General formula (P-1)

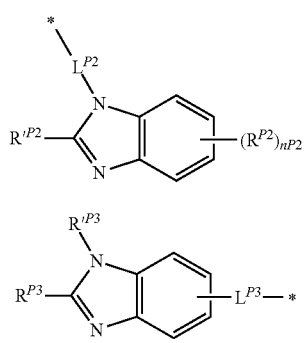
General formula (P-2)

General formula (P-3)
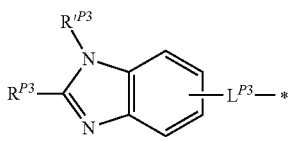

(In the general formulae (P-1) to (P-3), $R^{P1}$ to $R^{P3}$ and $R'^{P1}$ to $R'^{P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $n^{P1}$ and $n^{P2}$ represent an integer of 0 to 4, and in the case where there are a plurality of $R^{P1}$ to $R^{P3}$ and $R'^{P1}$ to $R'^{P3}$, these may be the same as or different from each other. $L^{P1}$ to $L^{P3}$ represent any one of divalent linking groups consisting of a single bond, an aryl ring, or a heteroaryl ring. * represents a binding position with the anthracene ring of the general formula (P)).

A preferred substituent other than the substituents represented by (P-1) to (P-3) as $R^P$ is an aryl group, more preferably any one of a phenyl group, a biphenyl group, a terphenyl group, and a naphthyl group, and still more preferably a naphthyl group.

$R^{P1}$ to $R^{P3}$ and $R'^{P1}$ to $R'^{P3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of divalent linking groups consisting of a single bond and an aryl ring, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the compound represented by the general formula (P) that can be used in the present invention should not be construed to be limited to the specific examples.

[Chem. 41]

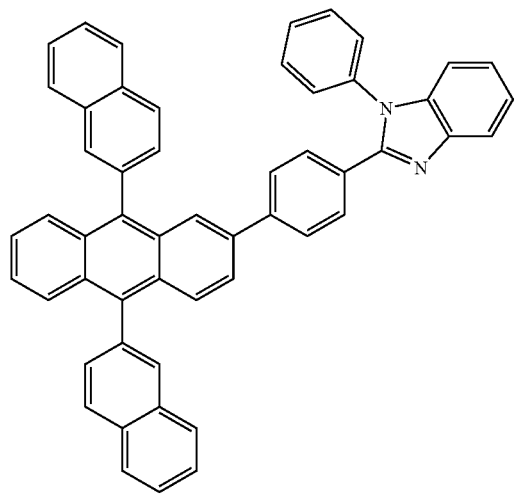

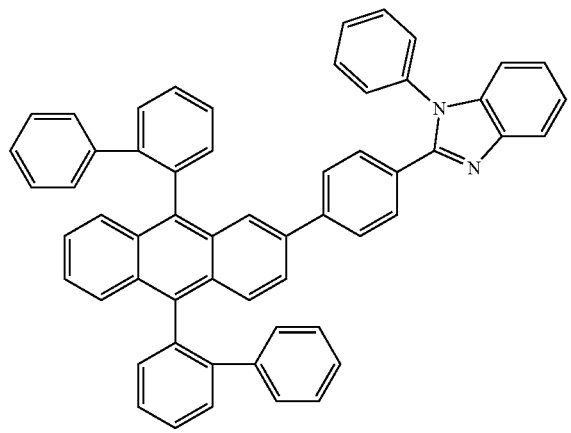

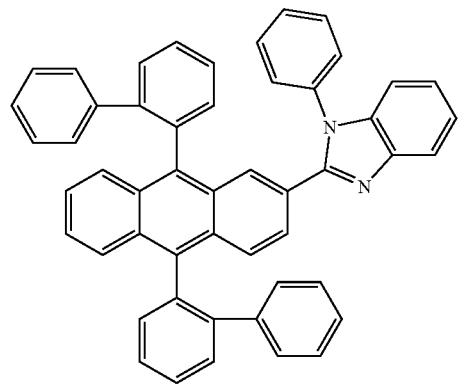

-continued
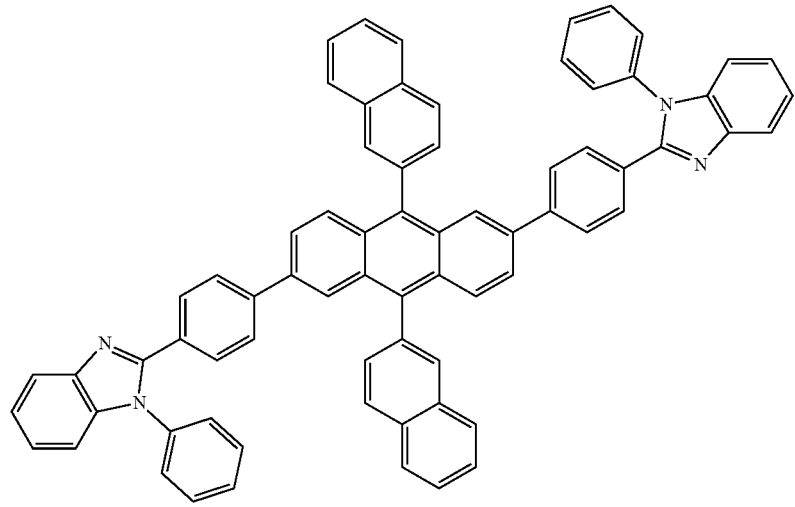
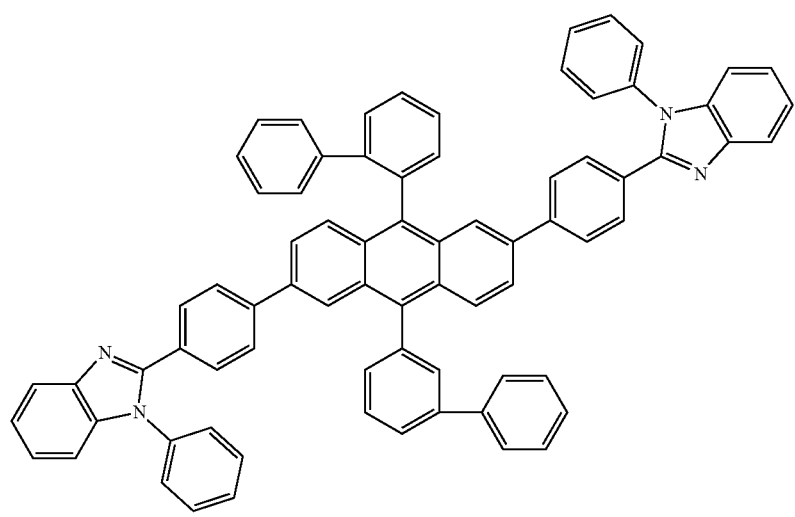
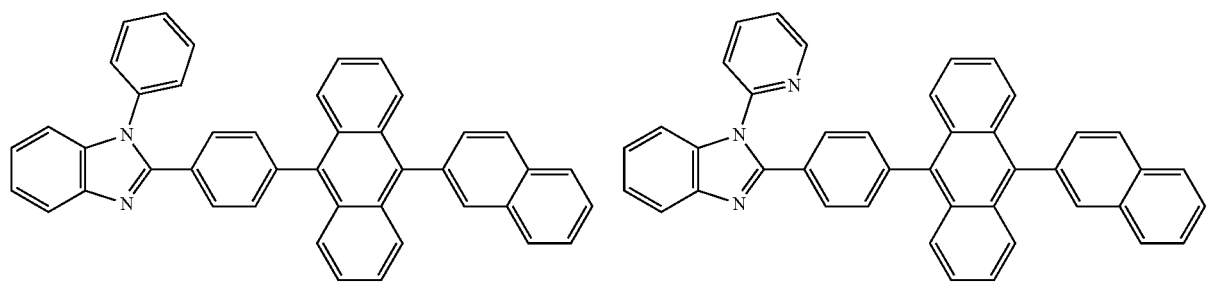
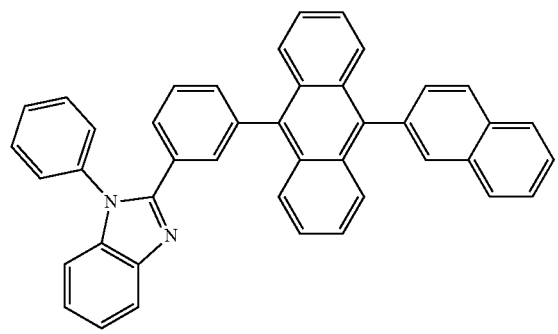

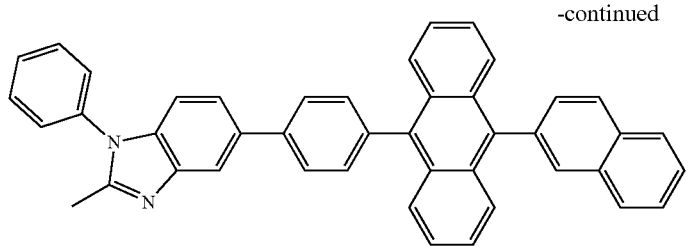

[Chem. 42]

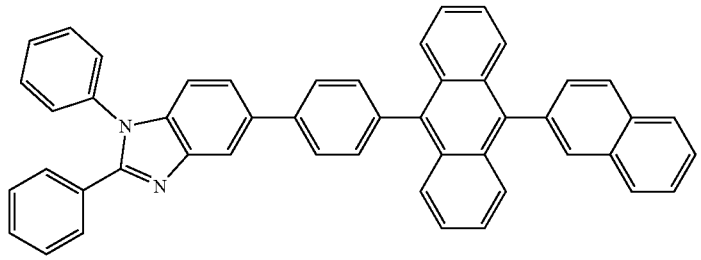

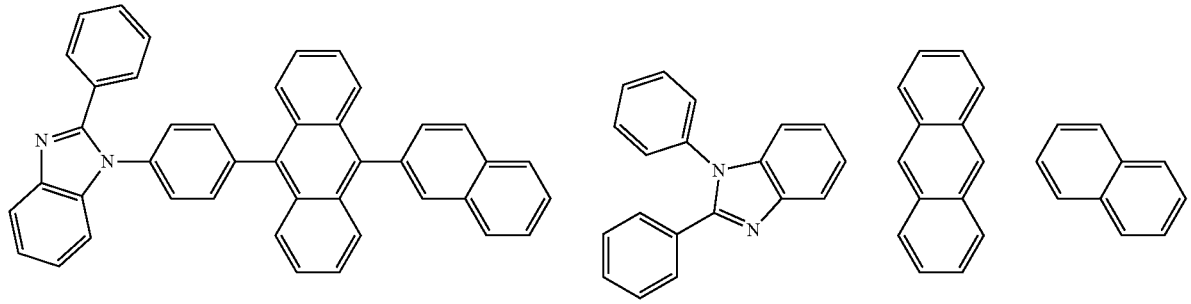

The compound represented by the general formula (P) can be synthesized by the method described in WO 2003/060956 and WO 2004/080975. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably included in the organic layer between the light emitting layer and the cathode, and more preferably in the layer adjacent to the cathode.

The compound represented by the general formula (P) is preferably contained in the amount of 70% by mass to 100% by mass, and more preferably 85% by mass to 100% by mass, based on the total mass of the organic layer added.

<Protective Layer>

In the present invention, the entirety of the organic electroluminescent element may be protected by a protective layer.

For the protective layer, the detailed description in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure. For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and still more preferably 7% or more. As to the numerical value of the external quantum efficiency, a maximum value of the external quantum efficiency obtained when the organic electroluminescent element is driven at 20° C., or a value of the external quantum efficiency in the vicinity of 300 cd/m² to 400 cd/m² obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, its light emitting wavelength is not limited, but is preferably used for blue or white light emission. Above all, in the organic electroluminescent element of the present invention, it is preferable to use the compound represented by the general formula (I) as a light emitting material to emit light, and particularly preferably to emit blue light.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
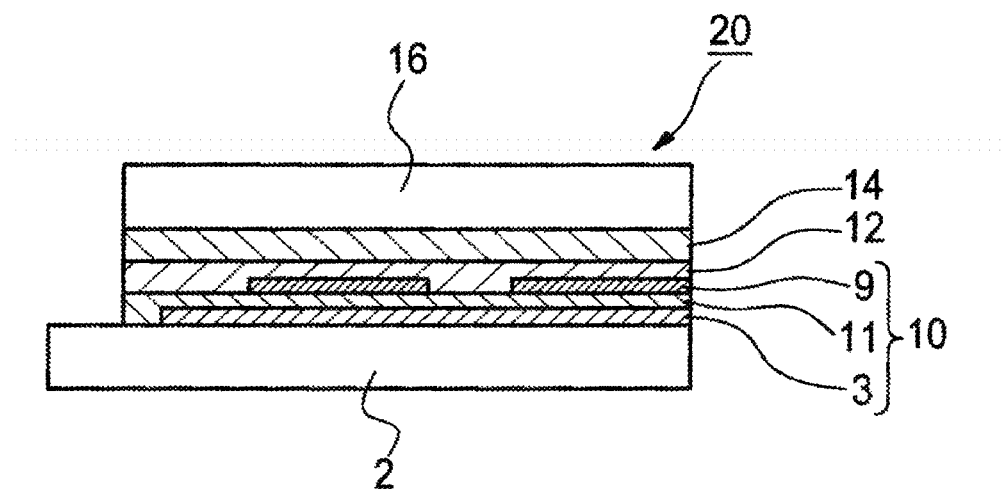
FIG. 2 is a schematic view showing one example of a light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet may also be used as the adhesive layer 14.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
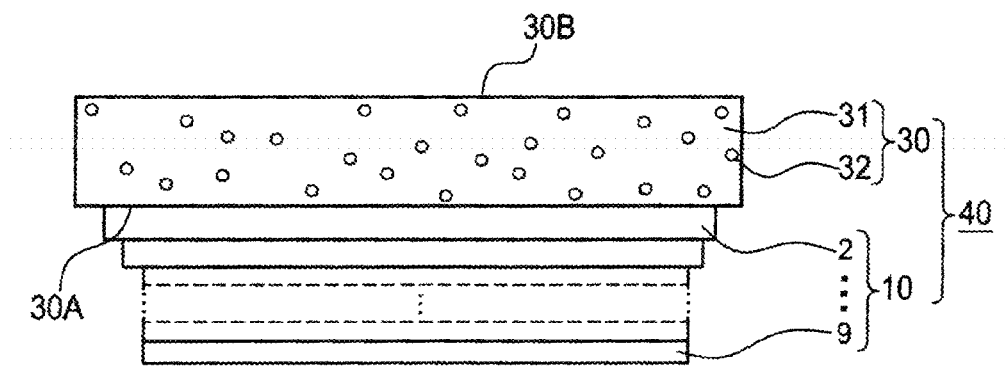
FIG. 3 is a schematic view showing one example of an illumination device according to the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples and Comparative Examples can be appropriately modified so far as the gist of the present invention is not deviated. Accordingly, it should not be construed that the scope of the present invention is limited to the specific examples shown below.

Example 1

(Synthesis)

The compound represented by the general formula (I) can be synthesized by the method described in the present specification or a combination of other known reactions. Representative examples of the specific synthesis procedure of the compound represented by the general formula (I) will be described below.

(Synthesis Example 1) Synthesis of Compound F1

A compound F1 was synthesized according to the following scheme.

[Chem. 43]

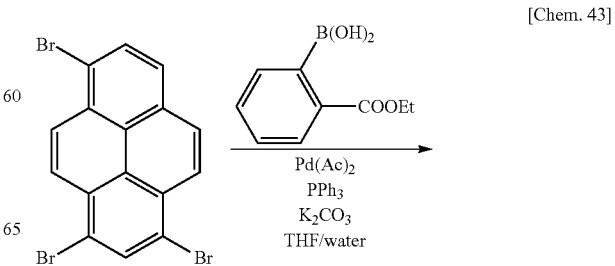

-continued

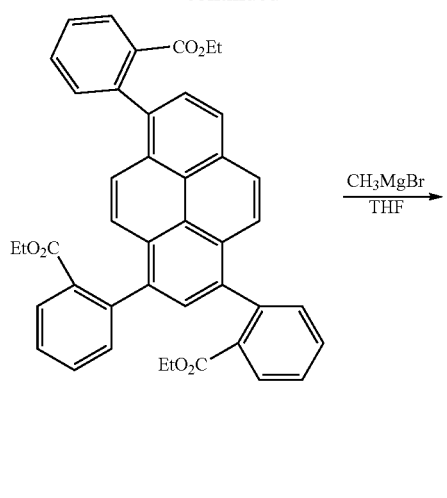

[Chem. 44]

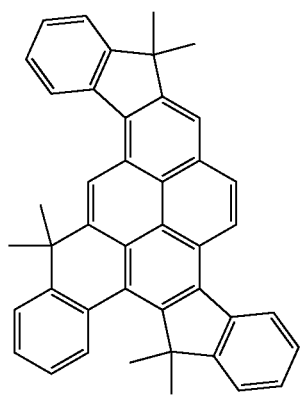
F1

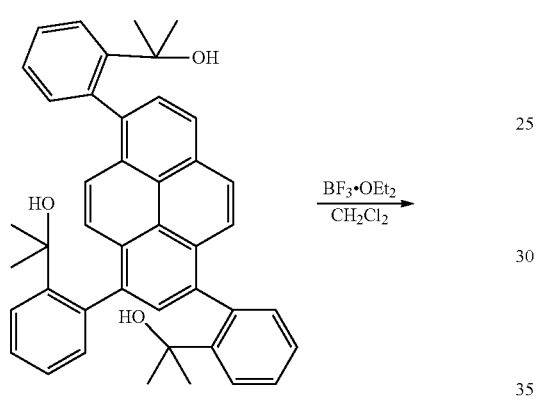

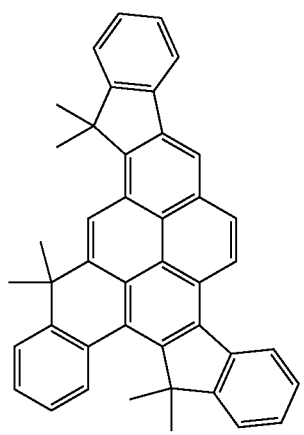
F2

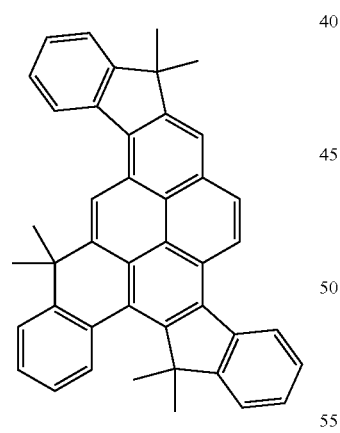

The compounds F1 to F8 used in Examples as well as the compounds other than the compound F1 synthesized above were synthesized by a method similar to that for the compound F1. The comparative compounds D1 to D4 were synthesized with reference to well-known literatures, in which the respective compounds are described.

The structural formulae of the compounds F1 to F8 represented by the general formula (I) used in Examples, and the structural formulae of the compounds D1 to D4 used in Comparative Examples are summarized below.

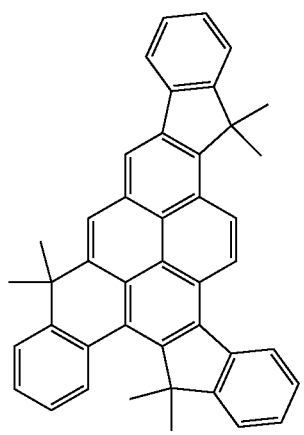
F3

F4
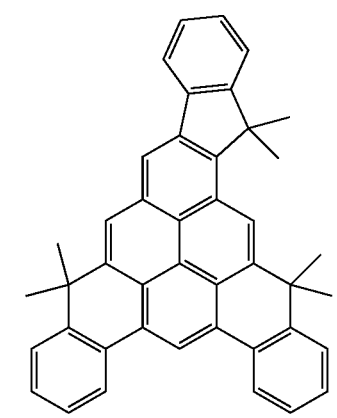
F5
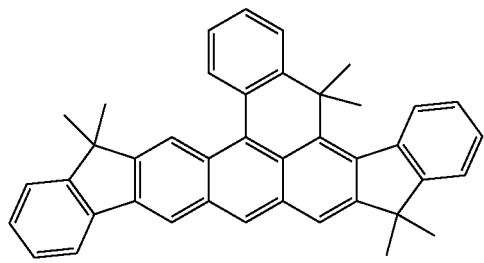
F6
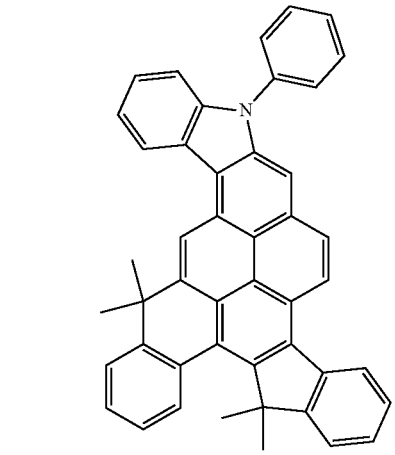
F7
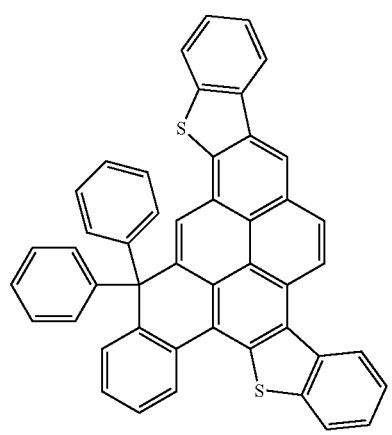
F8
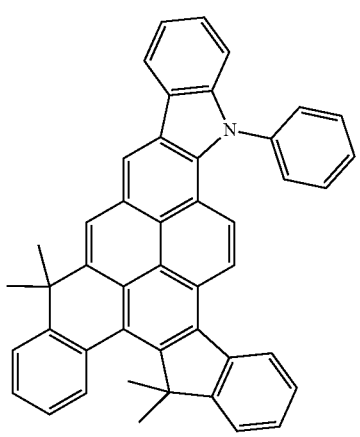
[Chem. 45]
Comparative compound
D1
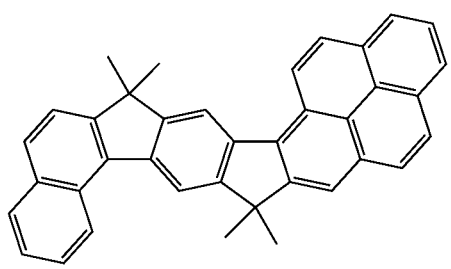
Compound described in
WO2010/012328
D2
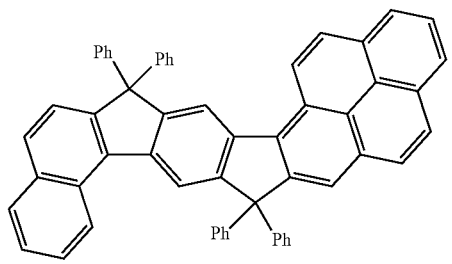
Compound described in
WO2010/012328
D3
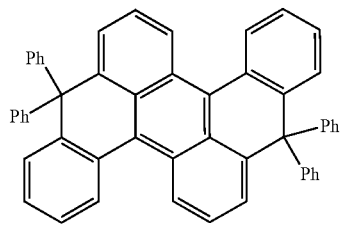
Compound described in
US2008/0100208

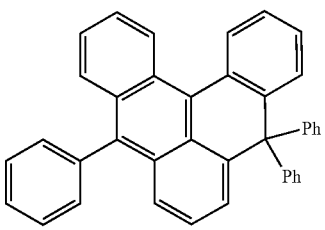

Compound described in
US2008/0100208

The materials other than F1 to F8 and D1 to D4 used in the case of fabrication of organic electroluminescent elements are shown below.

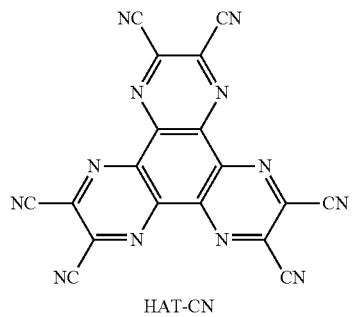

HAT-CN

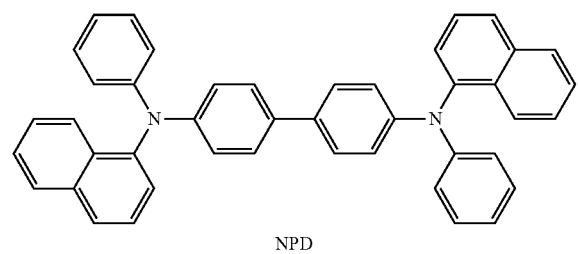

NPD

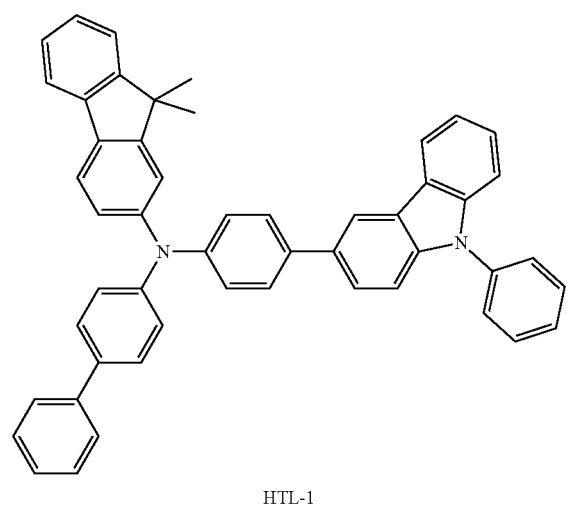

HTL-1

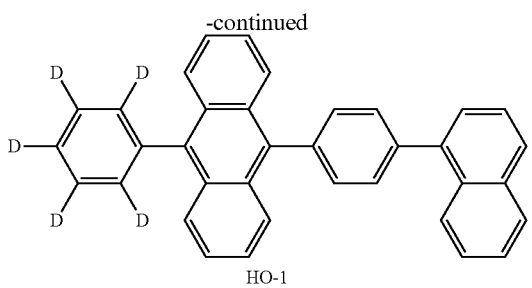

HO-1

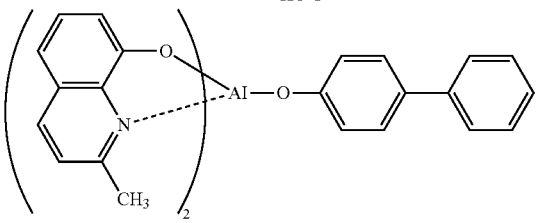

BAlq

Example 2

(Organic Electroluminescent Elements 1-1 to 1-8 of the present invention, and Comparative Elements 1-1 to 1-4)

(1) Purity of Materials Used

The materials used for fabrication of the elements were all subjected to sublimation purification and it was confirmed that the purity (absorption intensity area ratio at 254 nm) was 99.0% or more by using high performance liquid chromatography (TSKgel ODS-100Z, manufactured by Tosoh Corporation).

(2) Fabrication of Elements

A 0.5 mm-thick and 2.5 cm square glass substrate (manufactured by Geomatec Co., Ltd., surface resistance: 10 Ω/□) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method under an environment of a dew point temperature of −20° C.

First layer: HAT-CN: Film thickness 10 nm

Second layer: NPD: Film thickness 30 nm

Third layer: Host material HO-1 and the light emitting material described in Table 1 (mass ratio=95:5): Film thickness 30 nm Fourth layer: BAlq: Film thickness 30 nm 1 nm of lithium fluoride and 100 nm of metallic aluminum were deposited in this order thereon, thereby forming a cathode. Further, a patterned mask (mask having a light emitting area of 2 mm×2 mm) was provided on the layer of lithium fluoride, and metallic aluminum was deposited.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-CHIBA Ltd.), thereby obtaining the organic electroluminescent elements 1-1 to 1-8 of the present invention, and comparative elements 1-1 to 1-4.

(3) Evaluation of Elements

For the organic electroluminescent elements 1-1 to 1-8 of the present invention, and the comparative elements 1-1 to 1-4 obtained above, the following evaluation was carried out. The results are shown in Table 1 below.

(a) Number of Dark Spots after Driving

The organic electroluminescent element (fabricated under an environment of a dew point temperature of −20° C.) was set on a luminous spectrum measurement system (ELS1500) manufactured by Shimadzu Corporation, and a direct current voltage was applied at a constant current intensity (40 mA/cm$^2$) to drive the element for 100 hours. By counting the number of dark spots after driving visually, the magnitude of the dark spots generated during driving was evaluated. A smaller number of dark spots is more preferable.

TABLE 1

|  | Light emitting material | Number of dark spots after driving |
| --- | --- | --- |
| Element 1-1 of the present invention | F1 | 1 |
| Element 1-2 of the present invention | F2 | 0 |
| Element 1-3 of the present invention | F3 | 2 |
| Element 1-4 of the present invention | F4 | 1 |
| Element 1-5 of the present invention | F5 | 0 |
| Element 1-6 of the present invention | F6 | 1 |
| Element 1-7 of the present invention | F7 | 0 |
| Element 1-8 of the present invention | F8 | 0 |
| Comparative element 1-1 | D1 | 11 |
| Comparative element 1-2 | D2 | 14 |
| Comparative element 1-3 | D3 | 21 |
| Comparative element 1-4 | D4 | 24 |

Example 3

(Fabrication of Comparative Element 2-1)

(1) Preparation of Light Emitting Layer-Forming Coating Liquid

The light emitting material D1 (0.1% by mass) and the following host material HO-2 (0.9% by mass) were mixed with methyl ethyl ketone (98.99% by mass) to obtain a light emitting layer-forming coating liquid 1 for Comparative Examples.

[Chem. 47]

HO-2

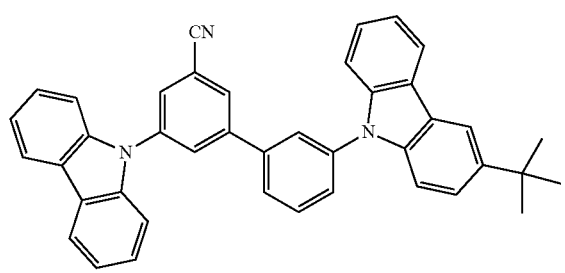

(2) Fabrication of Organic Electroluminescent Element

ITO was deposited on a 25 mm×25 mm×0.7 mm glass substrate to give a thickness of 150 nm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone and spin-coated (2,000 rpm, 20 seconds) to give a thickness of about 40 nm, and then dried at 120° C. for 30 minutes and subjected to an annealing treatment at 160° C. for 10 minutes to form a hole injecting layer.

[Chem. 48]

PTPDES-2

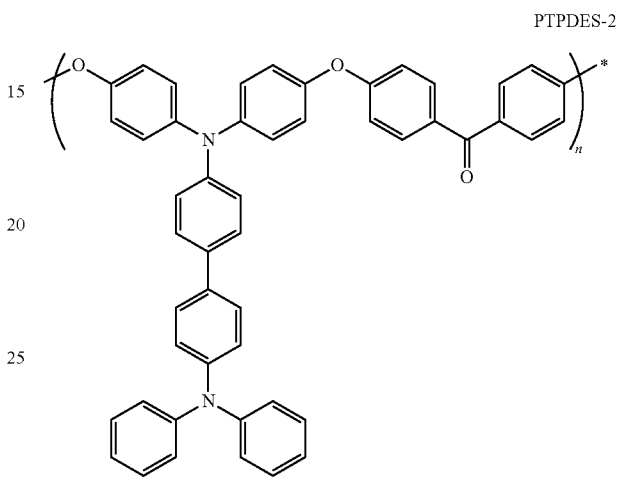

The light emitting layer-forming coating liquid 1 was spin-coated on a hole injecting layer (1,300 rpm, 30 seconds) to give a thickness of about 40 nm, thereby obtaining a light emitting layer.

Subsequently, BAlq (aluminum (III) bis(2-methyl-8-quinolinolato)-4-phenylphenolate) was formed as an electron transporting layer on a light emitting layer to give a thickness of 40 nm by a vacuum deposition method.

Lithium fluoride (LiF) was formed as an electron injecting layer on an electron transporting layer to give a thickness of 1 nm by a vacuum deposition method. Metal aluminum was further deposited to 70 nm thereon to give a cathode.

The laminate thus prepared was put into a glove box purged with an argon gas, and then sealed with a sealing can made of stainless steel and an ultraviolet ray-curable adhesive (XNR5516HV, manufactured by Nagase-CHIBA Ltd.) to fabricate a comparative element 2-1.

(Fabrication of Elements 2-1, 2-2, and 2-3 of the Present Invention)

In the same manner as for the light emitting layer-forming coating liquid 1, except that the light emitting material D1 was changed to the light emitting material described in Table 2 below in the light emitting layer-forming coating liquid 1, light emitting layer-forming coating liquids 2 to 4 for Examples were prepared.

Further, in the same manner as for the comparative element 2-1, except that the light emitting layer-forming coating liquid was changed as shown in Table 2 below, elements 2-1, 2-2 and 2-3 of the present invention were fabricated.

(3) Evaluation of Elements

Evaluation of the number of dark spots after driving was carried out in the same manner as in Example 2. The obtained results are shown in Table 2 below.

TABLE 2

| | Light emitting material | Number of dark spots after driving |
|---|---|---|
| Element 2-1 of the present invention | F1 | 3 |
| Element 2-2 of the present invention | F4 | 4 |
| Element 2-3 of the present invention | F8 | 2 |
| Comparative element 2-1 | D1 | 29 |

From the results in Tables 1 and 2, it could be seen that the organic electroluminescent element of the present invention using the compound represented by the general formula (I) as a light emitting material of a light emitting layer has a smaller number of dark spots after driving, as compared with the respective comparative elements.

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE
10: ORGANIC ELECTROLUMINESCENT ELEMENT
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
31: TRANSPARENT SUBSTRATE
30A: LIGHT INCIDENT SURFACE
30B: LIGHT OUTPUTTING SURFACE
32: FINE PARTICLES
40: ILLUMINATION DEVICE

The invention claimed is:

1. An organic electroluminescent element comprising:
a substrate;
a pair of electrodes including an anode and a cathode, disposed on the substrate; and
at least one organic layer including a light emitting layer, disposed between the electrodes,
wherein the at least organic layer contains at least one compound represented by general formula (I);

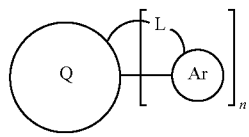

General formula (I)

wherein: Q represents an aromatic fused hydrocarbon ring having 10 to 30 carbon atoms or an aromatic fused heterocycle having 8 to 30 carbon atoms; Ar's each independently represents an arylene group having 6 to 30 carbon atoms or a heteroarylene group having 3 to 30 carbon atoms; each L independently represents $CR^{12}R^{13}$, $NR^{14}$, $SiR^{15}R^{16}$, an O atom, or an S atom; $R^{12}$, $R^{13}$, $R^{14}$, $R^{15}$ and $R^{16}$ each independently represent a substituent; and n represents an integer of 3 to 5;

wherein at least one of the following conditions (i) and (ii) are true:

(i) at least one L represents $NR^{14}$, $SiR^{15}R^{16}$, O, or S; wherein $R^{14}$, $R^{15}$ and $R^{16}$ each independently represents a fluorine atom, an alkyl group, an aryl group, or a heteroaryl group; and (ii) at least one ring comprising L is a six-membered ring.

2. The organic electroluminescent element according to claim 1, wherein in the general formula (I), L is $CR^{12}R^{13}$, $NR^{14}$, $SiR^{15}R^{16}$, an O atom, or an S atom, wherein $R^{12}$, $R^{13}$, $R^{14}$, $R^{15}$ and $R^{16}$ each independently represents a fluorine atom, an alkyl group, an aryl group, or a heteroaryl group.

3. The organic electroluminescent element according to claim 1, wherein in the general formula (I), Q represents any one of naphthalene, anthracene, phenanthrene, pyrene, chrysene, perylene, and triphenylene.

4. The organic electroluminescent element according to claim 1, wherein in the general formula (I), Ar's each independently represents a substituted or unsubstituted phenylene group.

5. The organic electroluminescent element according to claim 1, wherein in the general formula (I), Q represents pyrene.

6. The organic electroluminescent element according to claim 1, wherein the wherein the compound represented by the general formula (I) is selected from the group consisting of

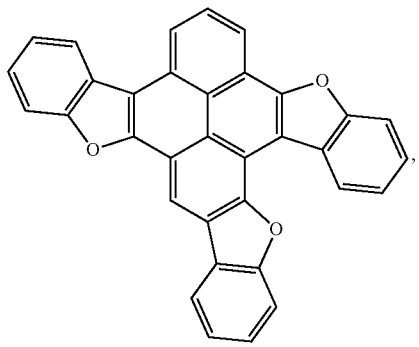

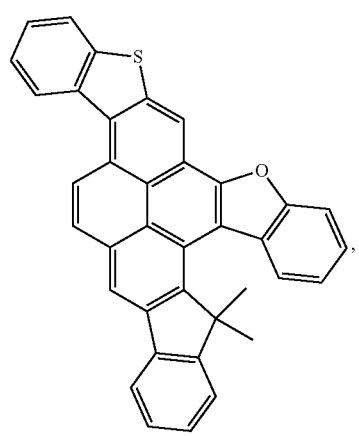

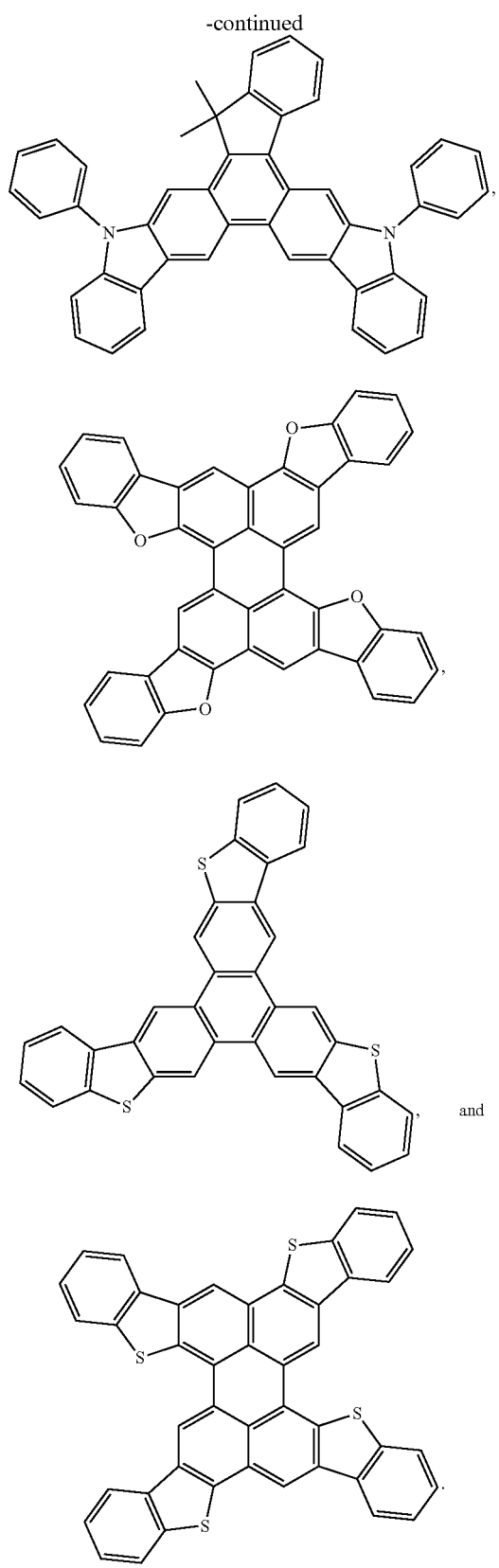
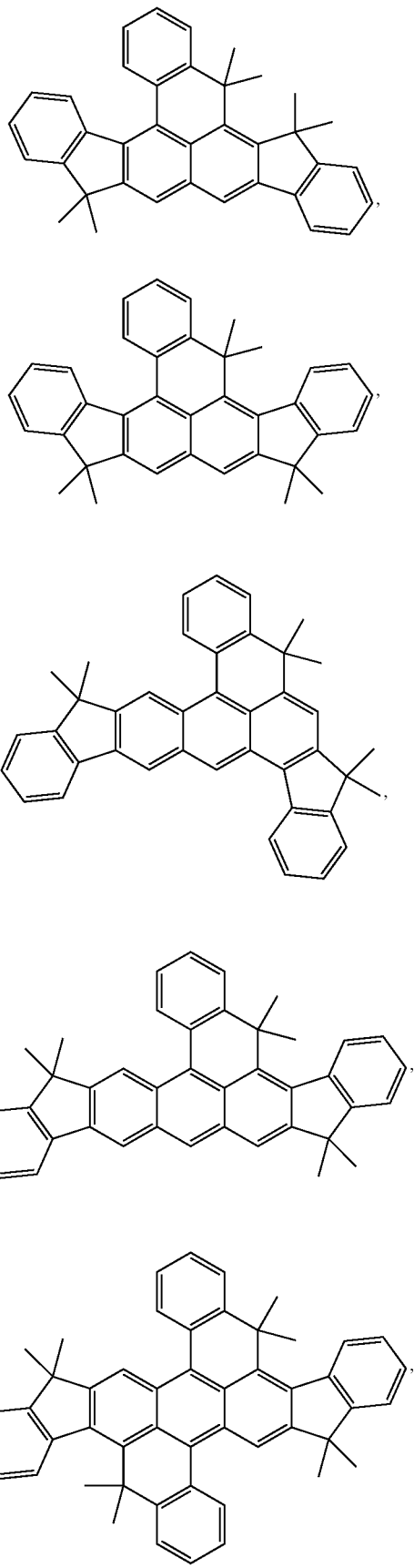
7. The organic electroluminescent element according to claim 1, wherein the compound represented by the general formula (I) is selected from the group consisting of:

95
-continued
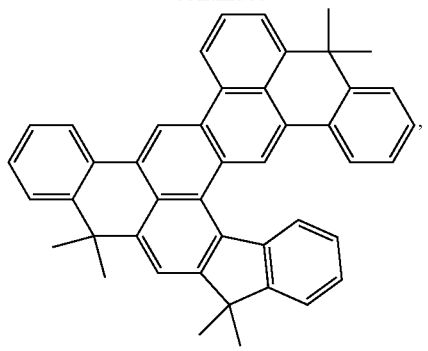
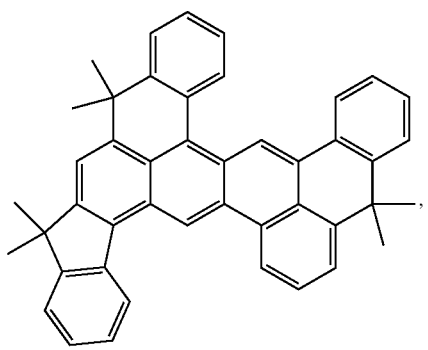
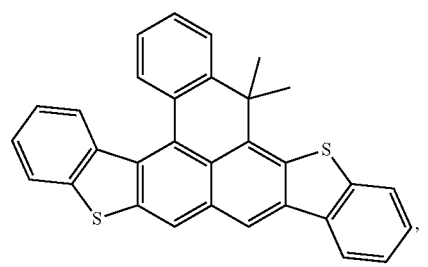
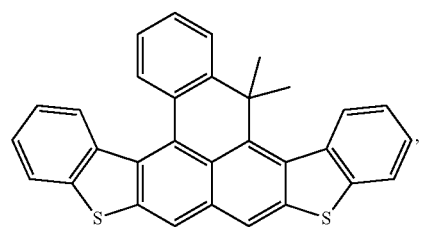
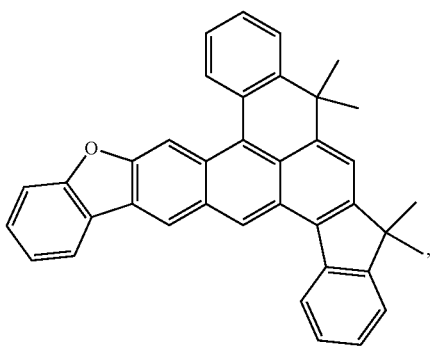
96
-continued
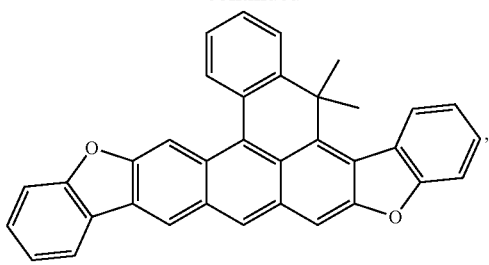
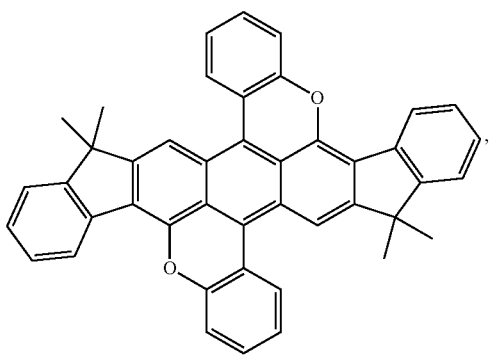
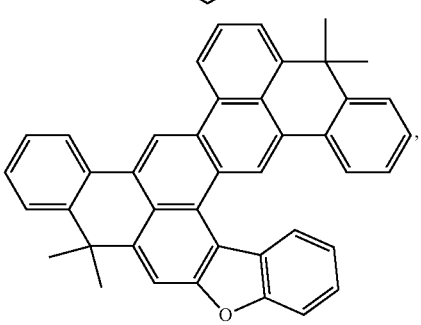
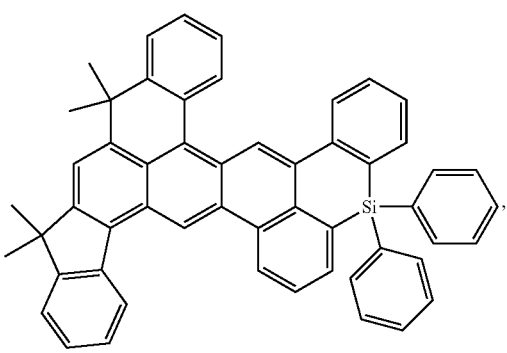, and
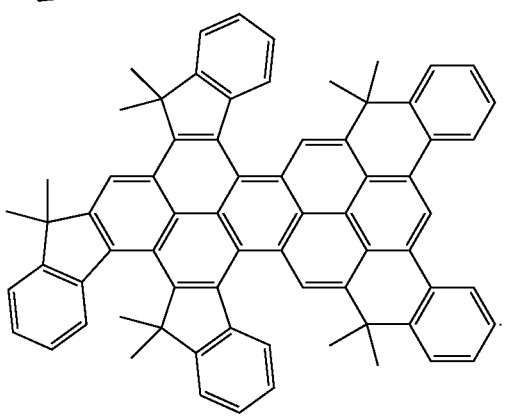

8. The organic electroluminescent element according to claim 1, wherein the compound represented by the general formula (I) is contained in the light emitting layer.

9. The organic electroluminescent element according to claim 1, the compound represented by the general formula (I) is a light emitting material contained in the light emitting layer.

10. The organic electroluminescent element according to claim 9, further comprising a host material in the light emitting layer.

11. The organic electroluminescent element according to claim 10, wherein the host material has an anthracene skeleton.

12. A light emitting device comprising the organic electroluminescent element according to claim 1.

13. A display device comprising the organic electroluminescent element according to claim 1.

14. An illumination device comprising the organic electroluminescent element according to claim 1.

15. A compound represented by the following general formula (I);

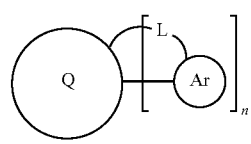

General formula (I)

wherein: Q represents an aromatic fused hydrocarbon ring having 10 to 30 carbon atoms or an aromatic fused heterocycle having 8 to 30 carbon atoms; Ar's each independently represents an arylene group having 6 to 30 carbon atoms or a heteroarylene group having 3 to 30 carbon atoms; each L independently represents $CR^{12}R^{13}$, $NR^{14}$, $SiR^{15}R^{16}$, an O atom, or an S atom; $R^{12}$, $R^{13}$, $R^{14}$, $R^{15}$ and $R^{16}$ each independently represent a substituent; and n represents an integer of 3 to 5;

wherein at least one ring comprising L is a six-membered ring.

16. A compound selected from the group consisting of:

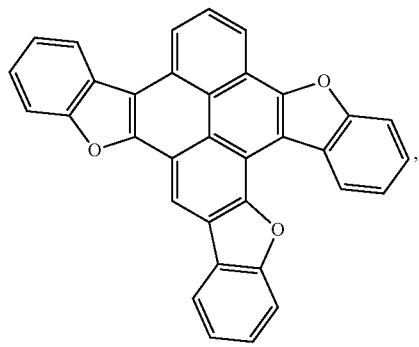

,

-continued

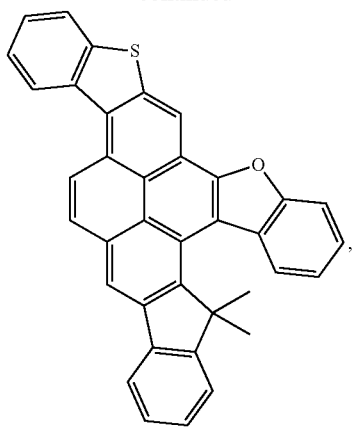

,

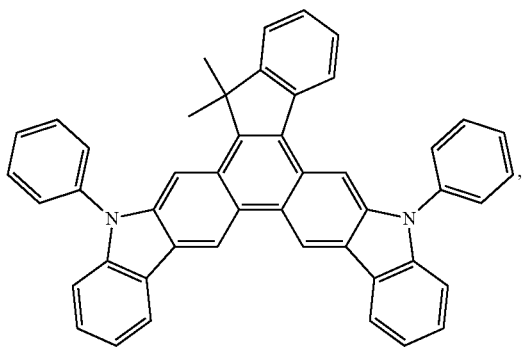

,

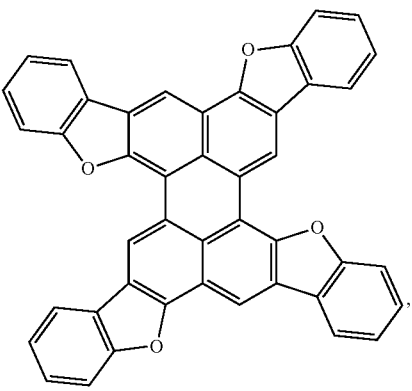

,

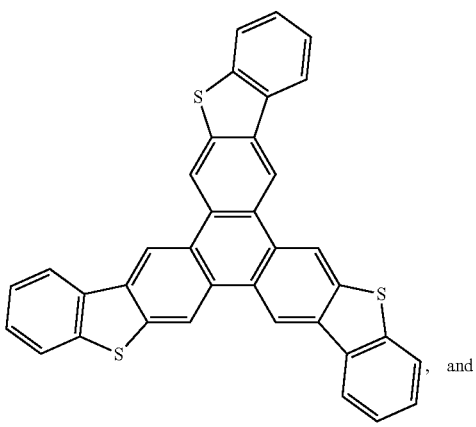

, and

99
-continued
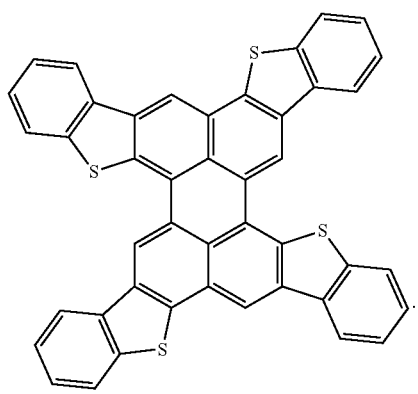
100
-continued
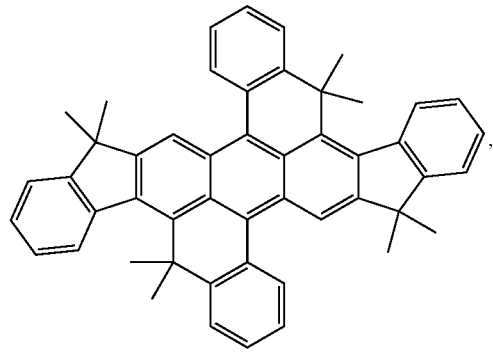
17. The compound of claim 15, wherein the compound represented by general formula (I) is selected from the group consisting of:
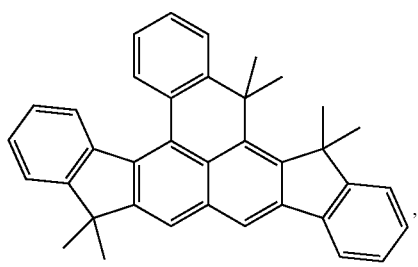
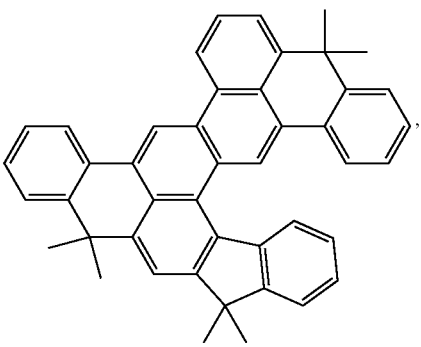
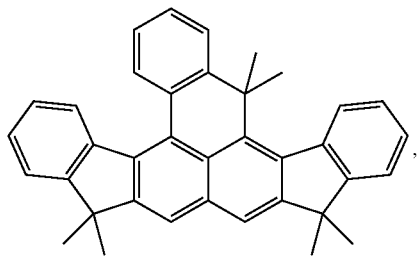
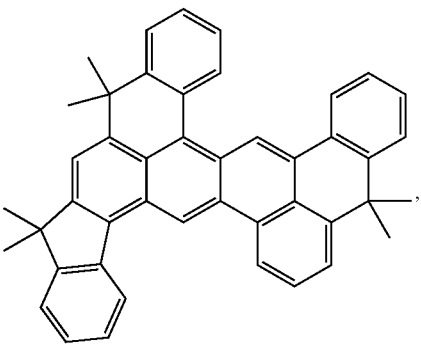
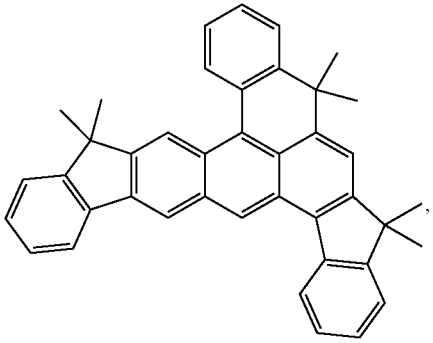
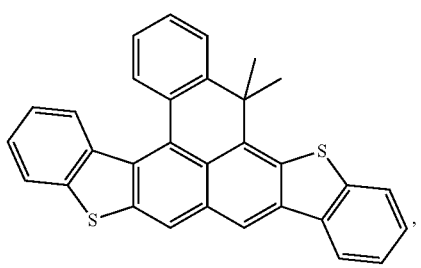
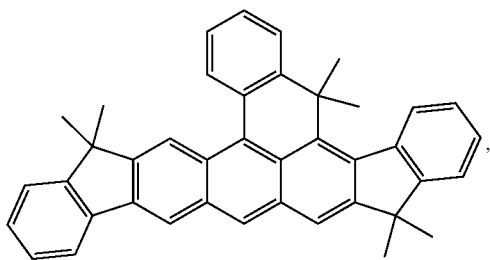
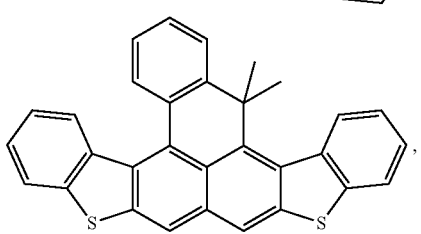

101
-continued
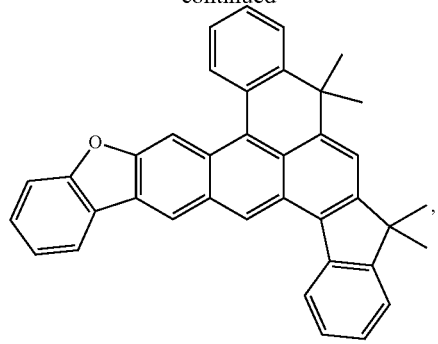
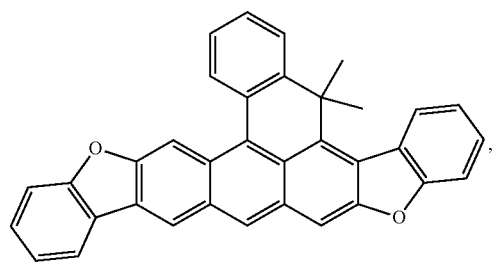
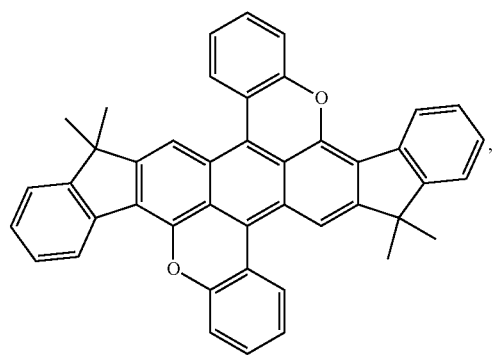
102
-continued
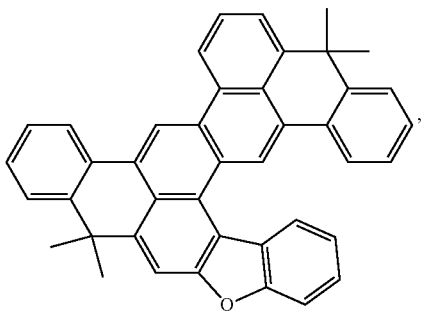
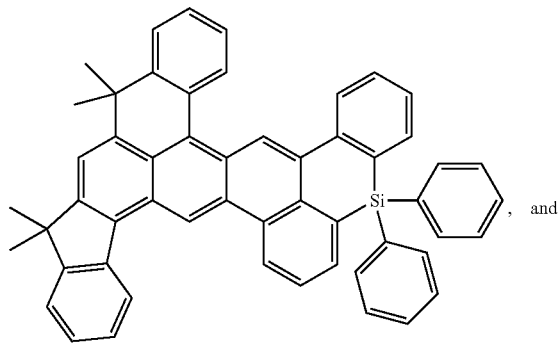, and
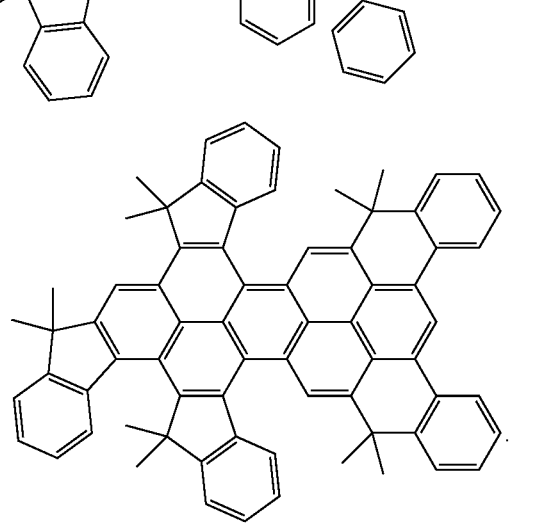
* * * * *